(12) United States Patent
Choi et al.

(10) Patent No.: US 6,913,907 B2
(45) Date of Patent: Jul. 5, 2005

(54) ENTEROCOCCUS FAECALIS POLYNUCLEOTIDES ENCODING EF059

(75) Inventors: Gil H. Choi, Rockville, MD (US); Camella Bailey, Washington, DC (US); Alex Hromockyj, Mountainview, CA (US); Charles A. Kunsch, Norcross, GA (US)

(73) Assignee: Human Genome Sciences, Inc., Rockville, MD (US)

( * ) Notice: Subject to any disclaimer, the term of this patent is extended or adjusted under 35 U.S.C. 154(b) by 246 days.

(21) Appl. No.: 10/206,576

(22) Filed: Jul. 29, 2002

(65) Prior Publication Data

US 2003/0017495 A1 Jan. 23, 2003

Related U.S. Application Data

(62) Division of application No. 09/071,035, filed on May 4, 1998, now Pat. No. 6,448,043.
(60) Provisional application No. 60/066,009, filed on Nov. 14, 1997, provisional application No. 60/046,655, filed on May 16, 1997, and provisional application No. 60/044,031, filed on May 6, 1997.

(51) Int. Cl.[7] .................. C07H 21/04; C12P 21/06; C12N 15/00
(52) U.S. Cl. ................ 435/69.1; 435/320.1; 435/252.3; 536/23.7
(58) Field of Search .................. 435/69.1, 69.7, 435/70.1, 71.1, 91.41, 320.1, 325, 243, 252.3, 254.11, 257.2; 530/350; 536/23.1, 23.7, 24.32; 935/9, 11, 12, 22, 23, 52, 55, 66

(56) References Cited

FOREIGN PATENT DOCUMENTS

WO    WO-00/068242 A1    11/2000

OTHER PUBLICATIONS

Kao et al, J. Bacteriol , 173:7650–7664, 1991.*
Nakayama et al. J. Bacteriol, 174: 7405–7408, 1994.*
Rudinger et al. in "Peptide Hormones", ed. Parsons J.A. University Park Press pp. 1–6, 1976.*
Burgess et al, The Journal of Cell Biology 111:2129–2138, 1990.*
Lazar et al, Molecular and Cellular Biology 8(3): 1247–1252, 1988.*
Jobling et al Mol. Microbiol. 5(7): 1755–67, 1991.*
Herzog et al DNA and Cell Biology 12(6): 465–471, 1993.*
Jazin et al, Regulatory Peptides 47:247–258, 1993.*
Nallapareddy et al. "Diversity of ace, a gene encoding a microbial surface component recognizing adhesive matrix molecules, from different strains of Enterococcus faecalis and evidence for production of ace during human infections", Infection and Immunity 68(9):5210–5217 (2000).
NCBI Accession No. NP813955; "Role of mobile DNA in the evolution of vancomycin–resistant Enterococcus faecalis", Science 299(5615):2071–2074 (2003) (Mar. 31, 2003).
Rich et al. "Ace is a collagen–binding MSCRAMM from Enterococcus faecalis", J. Biol. Chemistry 274(38):26939–26945 (1999).

* cited by examiner

Primary Examiner—Patricia A. Duffy
(74) Attorney, Agent, or Firm—Human Genome Sciences, Inc.

(57) ABSTRACT

The present invention relates to novel genes from E. faecalis and the polypeptides they encode. Also provided as are vectors, host cells, antibodies and methods for producing the same. The invention further relates to screening methods for identifying agonists and antagonists of E. faecalis polypeptide activity. The invention additionally relates to diagnostic methods for detecting Enterococcus nucleic acids, polypeptides and antibodies in a biological sample. The present invention further relates to novel vaccines for the prevention or attenuation of infection by Enterococcus.

38 Claims, No Drawings

ENTEROCOCCUS FAECALIS POLYNUCLEOTIDES ENCODING EF059

CROSS REFERENCE TO RELATED APPLICATIONS

This application is a division of and claims priority under 35 U.S.C. § 120 to U.S. application Ser. No. 09/071,035, filed May 4, 1998, now U.S. Pat. No. 6,448,043. which is a nonprovisional of and claims benefit under 35 U.S.C. § 119(e) of U.S. Provisional Application Nos. 60/046,655, filed May 16, 1997, Ser. No. 60/044,031, filed May 6, 1997, and 60/066,009, filed Nov. 14, 1997. U.S. Provisional Application No. 60/066,009, filed Nov. 14, 1997 is herein incorporated by reference in its entirety.

REFERENCE TO SEQUENCE LISTING AND TABLE 1

This application refers to a "Sequence Listing" and Table 1 listed below, which are provided as electronic documents on two identical compact discs (CD-R), labeled "Copy 1" and "Copy 2." These compact discs each contain the following files, which are hereby incorporated in their entirety herein:

| Document | File Name | Size in bytes | Date of Creation |
|---|---|---|---|
| Sequence Listing | PB369P1D1.seqlist.txt | 1,476,652 | Jul. 29, 2002 |
| Table 1 | PB369P1D1.table1.txt | 476,355 | Jul. 29, 2002 |

FIELD OF THE INVENTION

The present invention relates to novel *Enterococcus faecalis* genes (*E. faecalis*) nucleic acids and polypeptides. Also provided are vectors, host cells and recombinant methods for producing the same. Further provided are diagnostic methods for detecting *Enterococcus faecalis* using probes, primers, and antibodies to the *E. faecalis* nucleic acids and polypeptides of the present invention. The invention further relates to screening methods for identifying agonists and antagonists of *E. faecalis* polypeptide activity and to vaccines using *E. faecalis* nucleic acids and polypeptides.

BACKGROUND OF THE INVENTION

*Enterococci* have been recognized as being pathogenic for humans since the turn of the century when they were first described by Thiercelin in 1988 as microscopic organisms. The genus *Enterococcus* includes the species *Enterococcus faecalis* or *E. faecalis* which is the most common pathogen in the group, accounting for 80–90 percent of all *enterococcal* infections. See Lewis et al. (1990) Eur J. Clin Microbiol Infect Dis.9:111–117.

The incidence of *enterococcal* infections has increased in recent years and *enterococci* are now the second most frequently reported nosocomial pathogens. Enterococcal infection is of particular concern because of its resistance to antibiotics. Recent attention has focused on *enterococci* not only because of their increasing role in nosocomial infections, but also because of their remarkable and increasing resistance to antimicrobial agents. These factors are mutually reinforcing since resistance allows *enterococci* to survive in an environment in which antimicrobial agents are heavily used; the hospital setting provides the antibiotics which eliminate or suppress susceptible bacteria, thereby providing a selective advantage for resistant organisms, and the hospital also provides the potential for dissemination of resistant *enterococci* via the usual routes of hand and environmental contamination.

Antimicrobial resistance can be divided into two general types, inherent or intrinsic property and that which is acquired. The genes for intrinsic resistance, like other species characteristics, appear to reside on the chromosome. Acquired resistance results from either a mutation in the existing DNA or acquisition of new DNA. The various inherent traits expressed by *enterococci* include resistance to semisynthetic penicillinase-resistant penicillins, cephalosporins, low levels of aminoglycosides, and low levels of clindamycin. Examples of acquired resistance include resistance to chloramphenicol, erythromycin, high levels of clindamycin, tetracycline, high levels of aminoglycosides, penicillin by means of penicillinase, fluoroquinolones, and vancomycin. Resistance to high levels of penicillin without penicillinase and resistance to fluoroquinolones are not known to be plasmid or transposon mediated and presumably are due to mutation(s).

Although the main reservoir for *enterococci* in humans is the gastrointestinal tract, the bacteria can also reside in the gallbladder, urethra and vagina.

*E. faecalis* has emerged as an important pathogen in endocarditis, bacteremia, urinary tract infections (UTIs), intraabdominal infections, soft tissue infections, and neonatal sepsis. See Lewis et al. (1990) supra. In the 1970s and 1980s *enterococci* became firmly established as major nosocomial pathogens. They are now the fourth leading cause of hospital-acquired infection and the third leading cause of bacteremia in the United States. Fatality ratios for *enterococcal* bactermia range from 12% to 68%, with death due to *enterococcal* sepsis in 4 to 50% of these cases. See T. G. Emori (1993) Clin. Microbiol. Rev. 6:428–442.

The ability of *enterococci* to colonize the gastrointestinal tract, plus the many intrinsic and acquired resistance traits, means that these organisms, which usually seem to have relatively low intrinsic virulence, are given an excellent opportunity to become secondary invaders. Since nosocomial isolates of *enterococci* have displayed resistance to essentially every useful antimicrobial agent, it will likely become increasingly difficult to successfully treat and control *enterococcal* infections. Particularly when the various resistance genes come together in a single strain, an event almost certain to occur at some time in the future.

The etiology of diseases mediated or exacerbated by *Enterococcus faecalis*, involves the programmed expression of *E. faecalis* genes, and that characterizing these genes and their patterns of expression would dramatically add to our understanding of the organism and its host interactions. Knowledge of the *E. faecalis* gene and genomic organization would improve our understanding of disease etiology and lead to improved and new ways of preventing, treating and diagnosing diseases. Thus, there is a need to characterize the genome of *E. faecalis* and for polynucleotides of this organism.

SUMMARY OF THE INVENTION

The present invention provides for isolated *E. faecalis* polynucleotides and polypeptides shown in Table 1 and SEQ ID NO:1 through SEQ ID NO:496 (polynucleotide sequences having odd SEQ ID NOs and polypeptide sequences having even SEQ ID NOs). One aspect of the invention provides isolated nucleic acid molecules comprising polynucleotides having a nucleotide sequence selected from the group consisting of: (a) a nucleotide sequence shown in Table 1; (b) a nucleotide sequence encoding any of the amino acid sequences of the polypeptides shown in Table 1; and (c) a nucleotide sequence complementary to any of the nucleotide sequences in (a) or (b). The invention further provides for fragments of the nucleic acid molecules of (a), (b) & (c) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b) or (c) above, or a polynucleotide which hybridizes under stringent hybridization conditions to a polynucleotide in (a), (b) or (c) above. Additional nucleic acid embodiments of the invention relate to isolated nucleic acid molecules comprising polynucleotides which encode the amino acid sequences of epitope-bearing portions of a E. faecalis polypeptide having an amino acid sequence in (a) above.

The present invention also relates to recombinant vectors, which include the isolated nucleic acid molecules of the present invention, and to host cells containing the recombinant vectors, as well as to methods of making such vectors and host cells. The present invention further relates to the use of these vectors in the production of E. faecalis polypeptides or peptides by recombinant techniques.

The invention further provides isolated E. faecalis polypeptides having an amino acid sequence selected from the group consisting of an amino acid sequence of any of the polypeptides described in Table 1 or fragments thereof.

The polypeptides of the present invention also include polypeptides having an amino acid sequence with at least 70% similarity, and more preferably at least 75%, 80%, 85%, 90%, 95%, 96%, 97%, 98%, or 99% similarity to those described in Table 1, as well as polypeptides having an amino acid sequence at least 70% identical, more preferably at least 75% identical, and still more preferably 80%, 85%, 90%, 95%, 96%, 97%, 98%, or 99% identical to those above; as well as isolated nucleic acid molecules encoding such polypeptides.

The present invention further provides a single or multi-component vaccine comprising one or more of the E. faecalis polynucleotides or polypeptides described in Table 1, or fragments thereof, together with a pharmaceutically acceptable diluent, carrier, or excipient, wherein the E. faecalis polypeptide(s) are present in an amount effective to elicit an immune response to members of the Enterococcus genus, or at least E. faecalis, in an animal. The E. faecalis polypeptides of the present invention may further be combined with one or more immunogens of one or more other Enterococcal or non-Enterococcal organisms to produce a multi-component vaccine intended to elicit an immunological response against members of the Enterococcus genus and, optionally, one or more non-Enterococcal organisms.

The vaccines of the present invention can be administered in a DNA form, e.g., "naked" DNA, wherein the DNA encodes one or more Enterococcal polypeptides and, optionally, one or more polypeptides of a non-Enterococcal organism. The DNA encoding one or more polypeptides may be constructed such that these polypeptides are expressed as fusion proteins.

The vaccines of the present invention may also be administered as a component of a genetically engineered organism or host cell. Thus, a genetically engineered organism or host cell which expresses one or more E. faecalis polypeptides may be administered to an animal. For example, such a genetically engineered organism or host cell may contain one or more E. faecalis polypeptides of the present invention intracellularly, on its cell surface, or in its periplasmic space. Further, such a genetically engineered organism or host cell may secrete one or more E. faecalis polypeptides. The vaccines of the present invention may also be co-administered to an animal with an immune system modulator (e.g., CD86 and GM-CSF).

The invention also provides a method of inducing an immunological response in an animal to one or more members of the Enterococcus genus, preferably one or more isolates of the E. faecalis species, comprising administering to the animal a vaccine as described above.

The invention further provides a method of inducing a protective immune response in an animal, sufficient to prevent, attenuate, or control an infection by members of the Enterococcus genus, preferably at least E. faecalis species, comprising administering to the animal a composition comprising one or more of the polynucleotides or polypeptides described in Table 1, or fragments thereof. Further, these polypeptides, or fragments thereof, may be conjugated to another immunogen and/or administered in admixture with an adjuvant.

The invention further relates to antibodies elicited in an animal by the administration of one or more E. faecalis polypeptides of the present invention and to methods for producing such antibodies and fragments thereof. The invention further relates to recombinant antibodies and fragments thereof and to methods for producing such antibodies and fragments thereof.

The invention also provides diagnostic methods for detecting the expression of the polynucleotides of Table 1 by members of the Enterococcus genus in an animal. One such method involves assaying for the expression of a polynucleotide encoding E. faecalis polypeptides in a sample from an animal. This expression may be assayed either directly (e.g., by assaying polypeptide levels using antibodies elicited in response to amino acid sequences described in Table 1) or indirectly (e.g., by assaying for antibodies having specificity for amino acid sequences described in Table 1). The expression of polynucleotides can also be assayed by detecting the nucleic acids of Table 1. An example of such a method involves the use of the polymerase chain reaction (PCR) to amplify and detect Enterococcus nucleic acid sequences.

The present invention also relates to nucleic acid probes having all or part of a nucleotide sequence described in Table 1 (odd SEQ ID NOs) which are capable of hybridizing under stringent conditions to Enterococcus nucleic acids. The invention further relates to a method of detecting one or more Enterococcus nucleic acids in a biological sample obtained from an animal, said one or more nucleic acids encoding Enterococcus polypeptides, comprising: (a) contacting the sample with one or more of the above-described nucleic acid probes, under conditions such that hybridization occurs, and (b) detecting hybridization of said one or more probes to the Enterococcus nucleic acid present in the biological sample.

Other uses of the polypeptides of the present invention include: inter alia, to detect E. aurues in immunoassays, as epitope tags, as molecular weight markers on SDS-PAGE gels, as molecular weight markers for molecular sieve gel filtration columns, to generate antibodies that specifically bind E. faecalis polypeotides of the present invention for the detection E. faecalis in immunoassays, to generate an immune response against E. faecalis and other Enterococcus species, and as vaccines against E. faecalis, other Enterococcus species and other bacteria genuses.

Isolated nucleic acid molecules of the present invention, particularly DNA molecules, are useful as probes for gene mapping and for identifying E. faecalis in a biological samples, for instance, by Southern and Northern blot analysis. Polynucleotides of the present invention are also useful in detecting E. faecalis by PCR using primers for a particular E. faecalis polynucleotide. Isolated polynucleotides of the present invention are also useful in making the polypeptides of the present invention.

DETAILED DESCRIPTION

The present invention relates to recombinant E. faecalis nucleic acids and fragments thereof. The present invention further relates to recombinant E. faecalis polypeptides and fragments thereof. The invention also relates to methods for using these polypeptides to produce immunological responses and to confer immunological protection to disease caused by members of the genus Enterococcus, at least isolates of the E. faecalis genus. The invention further relates to nucleic acid sequences which encode antigenic E. faecalis polypeptides and to methods for detecting E. faecalis nucleic acids and polypeptides in biological samples. The invention also relates to antibodies specific for the polypeptides and peptides of the present invention and methods for detecting such antibodies produced in a host animal.

Definitions

The following definitions are provided to clarify the subject matter which the inventors consider to be the present invention.

As used herein, the phrase "pathogenic agent" means an agent which causes a disease state or affliction in an animal. Included within this definition, for examples, are bacteria, protozoans, fungi, viruses and metazoan parasites which either produce a disease state or render an animal infected with such an organism susceptible to a disease state (e.g., a secondary infection). Further included are species and strains of the genus Enterococcus which produce disease states in animals.

As used herein, the term "organism" means any living biological system, including viruses, regardless of whether it is a pathogenic agent.

As used herein, the term "Enterococcus" means any species or strain of bacteria which is members of the genus Enterococcus. Such species and strains are known to those of skill in the art, and include those that are pathogenic and those that are not.

As used herein, the phrase "one or more E. faecalis polypeptides of the present invention" means polypeptides comprising the amino acid sequence of one or more of the E. faecalis polypeptides described in Table 1 (even SEQ ID NOs). These polypeptides may be expressed as fusion proteins wherein the E. faecalis polypeptides of the present invention are linked to additional amino acid sequences which may be of Enterococcal or non-Enterococcal origin. This phrase further includes polypeptide comprising fragments of the E. faecalis polypeptides of the present invention. Additional definitions are provided throughout the specification.

Explanation of Table 1

Table 1, provided on CD-R and incorporated by reference herein, provides information describing genes which encode polypeptides of E. faecalis. The table lists the gene identifier which consists of the letters EF, which denote E. faecalis, followed immediately by a three digit numeric code, which arbitrarily number the E. faecalis genes of the present invention. A number from 1 through 4 follows the three digit number. A number 1 represents the full length open reading frame of the gene specified by the preceeding three digit number. A number 2 represents the full lenght polypeptide encoded by the gene specified the preceeding three digit number. A number 3 represents a polynucleotide fragment, of the gene represented by the preceeding three digit number, used to produce an antigenic polypeptide. A number 4 represents an antigenic polypeptide fragement, of the gene represented by the preceeding three digit number, used in the to stimulate an immune response or as a vaccine. The nucleotide and amino acid sequences of each gene and fragment are also shown in the Sequence Listing under the SEQ ID NO listed in Table 1.

Explanation of Table 2

Table 2 lists accession numbers for the closest matching sequences between the polypeptides of the present invention and those available through GenBank and Derwent databases. These reference numbers are the database entry numbers commonly used by those of skill in the art, who will be familar with their denominations. The descriptions of the numenclature for GenBank are available from the National Center for Biotechnology Information. Column 1 lists the gene or ORF of the present invention. Column 2 lists the accession number of a "match" gene sequence in GenBank or Derwent databases. Column 3 lists the description of the "match" gene sequence. Columns 4 and 5 are the high score and smallest sum probability, respectively, calculated by BLAST. Polypeptides of the present invention that do not share significant identity/similarity with any polypeptide sequences of GenBank and Derwent are not represented in Table 2. Polypeptides of the present invention that share significant identity/similarity with more than one of the polypeptides of GenBank and Derwent are represented more than once.

Explanation of Table 3

The E. faecalis polypeptides of the present invention may include one or more conservative amino acid substitutions from natural mutations or human manipulation as indicated in Table 3. Changes are preferably of a minor nature, such as conservative amino acid substitutions that do not significantly affect the folding or activity of the protein. Residues from the following groups, as indicated in Table 3, may be substituted for one another: Aromatic, Hydrophobic, Polar, Basic, Acidic, and Small, Explanation of Table 4

Table 4 lists residues comprising antigenic epitopes of antigenic epitope-bearing fragments present in each of the full length E. faecalis polypeptides described in Table 1 as predicted by the inventors using the algorithm of Jameson and Wolf, (1988) Comp. Appl. Biosci. 4:181–186. The Jameson-Wolf antigenic analysis was performed using the computer program PROTEAN (Version 3.11 for the Power MacIntosh, DNASTAR, Inc., 1228 South Park Street Madison, Wis.). E. faecalis polypeptide shown in Table 1 may one or more antigenic epitopes comprising residues described in Table 4. It will be appreciated that depending on the analytical criteria used to predict antigenic determinants, the exact address of the determinant may vary slightly. The residues and locations shown described in Table 4 correspond to the amino acid sequences for each full length gene sequence shown in Table 1 and in the Sequence Listing. Polypeptides of the present invention that do not have antigenic epitopes recognized by the Jameson-Wolf algorithm are not represented in Table 2.

Selection of Nucleic Acid Sequences Encoding Antigenic E. faecalis Polypeptides

Sequenced E. faecalis genomic DNA was obtained from the E. faecalis strain V586. The E. faecalis strain V586 was deposited May 2, 1997 at the ATCC, 10801 University Blvd. Manassas, Va. 20110–2209, and given accession number 55969.

Some ORFs contained in the subset of fragments of the *E. faecalis* genome disclosed herein were derived through the use of a number of screening criteria detailed below. The ORFs are bounded at the amino terminus by a methionine or valine residue and usually at the carboxy terminus by a stop codon.

Most of the selected sequences consist of complete ORFs. The polypeptides that do not comprise a complete ORF can be determined by determining whether the corresponding polynucleotide sequence comprises a stop codon after the codon for the last amino acid residue in the polypeptide sequence. It is not always preferred to express a complete ORF in a heterologous system. It may be challenging to express and purify a highly hydrophobic protein by common laboratory methods. Some of the polypeptide vaccine candidates described herein have been modified slightly to simplify the production of recombinant protein. For example, nucleotide sequences which encode highly hydrophobic domains, such as those found at the amino terminal signal sequence, have been excluded from some constructs used for expression of the polypeptides. Furthermore, any highly hydrophobic amino acid sequences occurring at the carboxy terminus have also been excluded from the recombinant expression constructs. Thus, in one embodiment, a polypeptide which represents a truncated or modified ORF may be used as an antigen.

While numerous methods are known in the art for selecting potentially immunogenic polypeptides, many of the ORFs disclosed herein were selected on the basis of screening *Enterococcus faecalis* ORFs for several aspects of potential immunogenicity. One set of selection criteria are as follows:

1. Type I signal sequence: An amino terminal type I signal sequence generally directs a nascent protein across the plasma and outer membranes to the exterior of the bacterial cell. Experimental evidence obtained from studies with *Escherichia coli* suggests that the typical type I signal sequence consists of the following biochemical and physical attributes (Izard, J. W. and Kendall, D. A. *Mol. Microbiol.* 13:765–773 (1994)). The length of the type I signal sequence is approximately 15 to 25 primarily hydrophobic amino acid residues with a net positive charge in the extreme amino terminus. In addition, the central region of the signal sequence adopts an alpha-helical conformation in a hydrophobic environment. Finally, the region surrounding the actual site of cleavage is ideally six residues long, with small side-chain amino acids in the −1 and −3 positions.

2. Type IV signal sequence: The type IV signal sequence is an example of the several types of functional signal sequences which exist in addition to the type I signal sequence detailed above. Although functionally related, the type IV signal sequence possesses a unique set of biochemical and physical attributes (Strom, M. S. and Lory, S., *J. Bacteriol.* 174:7345–7351 (1992)). These are typically six to eight amino acids with a net basic charge followed by an additional sixteen to thirty primarily hydrophobic residues. The cleavage site of a type IV signal sequence is typically after the initial six to eight amino acids at the extreme amino terminus. In addition, type IV signal sequences generally contain a phenylalanine residue at the +1 site relative to the cleavage site.

3. Lipoprotein: Studies of the cleavage sites of twenty-six bacterial lipoprotein precursors has allowed the definition of a consensus amino acid sequence for lipoprotein cleavage. Nearly three-fourths of the bacterial lipoprotein precursors examined contained the sequence L-(A,S)-(G,A)-C at positions −3 to +1, relative to the point of cleavage (Hayashi, S. and Wu, H. C., *J. Bioenerg. Biomembr.* 22:451–471 (1990)).

4. LPXTG motif: It has been experimentally determined that most anchored proteins found on the surface of gram-positive bacteria possess a highly conserved carboxy terminal sequence. More than fifty such proteins from organisms such as *S. pyogenes, S. mutans, E. faecalis, S. pneumoniae,* and others, have been identified based on their extracellular location and carboxy terminal amino acid sequence (Fischetti, V. A., *ASM News* 62:405–410 (1996)). The conserved region consists of six charged amino acids at the extreme carboxy terminus coupled to 15–20 hydrophobic amino acids presumed to function as a transmembrane domain. Immediately adjacent to the transmembrane domain is a six amino acid sequence conserved in nearly all proteins examined. The amino acid sequence of this region is L-P-X-T-G-X (SEQ ID NO:497), where X is any amino acid.

An algorithm for selecting antigenic and immunogenic *Enterococcus faecalis* polypeptides including the foregoing criteria was developed. The algorithm is similar to that described in U.S. patent application Ser. No. 08/781,986, filed Jan. 3, 1997, which is fully incorporated by reference herein. Use of the algorithm by the inventors to select immunologically useful *Enterococcus faecalis* polypeptides resulted in the selection of a number of the disclosed ORFs. Polypeptides comprising the polypeptides identified in this group may be produced by techniques standard in the art and as further described herein.

Nucleic Acid Molecules

Sequenced *E. faecalis* genomic DNA was obtained from the *E. faecalis* strainV586. As discussed elsewhere herein, polynucleotides of the present invention readily may be obtained by routine application of well known and standard procedures for cloning and sequencing DNA. Detailed methods for obtaining libraries and for sequencing are provided below, for instance. A wide variety of *Enterococcus faecalis* strains that can be used to prepare *E. faecalis* genomic DNA for cloning and for obtaining polynucleotides and polypeptides of the present invention. A wide variety of *Enterococcus faecalis* strains are available to the public from recognized depository institutions, such as the American Type Culture Collection (ATCC). It is recognized that minor variation is the nucleic acid and amino acid sequence may be expected from *E faecalis* strain to strain. The present invention provides for genes, including both polynucleotides and polypeptides, of the of the present invention from all the *Enterococcus faecalis* strains.

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion. In case of conflict between Table 1 and either the nucleic acid sequence of the clones listed in Table 1 or the amino acid sequence of the protein expressed by the clones listed in Table 1, the clones listed in Table 1 are controlling. By "nucleotide sequence" of a nucleic acid molecule or polynucleotide is intended to mean either a DNA or RNA sequence. Using the information provided herein, such as the nucleotide sequence in Table 1, a nucleic acid molecule of the present invention encoding a E. faecalis polypeptide may be obtained using standard cloning and screening procedures, such as those for cloning DNAs using genomic DNA as starting material. See, e.g., Sambrook et al. MOLECULAR CLONING: A LABORATORY MANUAL (Cold Spring Harbor, N.Y. 2nd ed. 1989); Ausubel et al., CURRENT PROTOCOLS IN MOLECULAR BIOLOGY (John Wiley and Sons, N.Y. 1989). Illustrative of the invention, the nucleic acid molecule described in Table 1 was discovered in a DNA library derived from a E. faecalis genomic DNA.

Nucleic acid molecules of the present invention may be in the form of RNA, such as mRNA, or in the form of DNA, including, for instance, DNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. This includes segments of DNA comprising the E. faecalis polynucleotides of the present invention isolated from the native chromosome. These fragments include both isolated fragments consisting only of E. faecalis DNA and fragments comprising heterologous sequences such as vector sequences or other foreign DNA. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

In addition, isolated nucleic acid molecules of the invention include DNA molecules which comprise a sequence substantially different from those described above but which, due to the degeneracy of the genetic code, still encode a E. faecalis polypeptides and peptides of the present invention (e.g. polypeptides of Table 1). That is, all possible DNA sequences that encode the E. faecalis polypeptides of the present invention. This includes the genetic code and species-specific codon preferences known in the art. Thus, it would be routine for one skilled in the art to generate the degenerate variants described above, for instance, to optimize codon expression for a particular host (e.g., change codons in the bacteria mRNA to those preferred by a mammalian or other bacterial host such as E. coli).

The invention further provides isolated nucleic acid molecules having the nucleotide sequence shown in Table 1 or a nucleic acid molecule having a sequence complementary to one of the above sequences. Such isolated molecules, particularly DNA molecules, are useful as probes for gene mapping and for identifying E. faecalis in a biological sample, for instance, by PCR, Southern blot, Northern blot, or other form of hybridization analysis.

The present invention is further directed to nucleic acid molecules encoding portions or fragments of the nucleotide sequences described herein. Fragments include portions of the nucleotide sequences of Table 1, or the E. faecalis nucleotide sequences contained in the plasmid clones listed in Table 1, at least 10 contiguous nucleotides in length selected from any two integers, one of which representing a 5' nucleotide position and a second of which representing a 3' nucleotide position, where the first nucleotide for each nucleotide sequence in Table 1 is position 1. That is, every combination of a 5' and 3' nucleotide position that a fragment at least 10 contiguous nucleotides in length could occupy is included in the invention. At least means a fragment may be 10 contiguous nucleotide bases in length or any integer between 10 and the length of an entire nucleotide sequence of Table 1 minus 1. Therefore, included in the invention are contiguous fragments specified by any 5' and 3' nucleotide base positions of a nucleotide sequences of Table 1 wherein the contiguous fragment is any integer between 10 and the length of an entire nucleotide sequence minus 1.

Further, the invention includes polynucleotides comprising fragments specified by size, in nucleotides, rather than by nucleotide positions. The invention includes any fragment size, in contiguous nucleotides, selected from integers between 10 and the length of an entire nucleotide sequence minus 1. Preferred sizes of contiguous nucleotide fragments include 20 nucleotides, 30 nucleotides, 40 nucleotides, 50 nucleotides. Other preferred sizes of contiguous nucleotide fragments, which may be useful as diagnostic probes and primers, include fragments 50–300 nucleotides in length which include, as discussed above, fragment sizes representing each integer between 50–300. Larger fragments are also useful according to the present invention corresponding to most, if not all, of the nucleotide sequences shown in Table 1 or of the E. faecalis nucleotide sequences of the plasmid clones listed in Table 1. The preferred sizes are, of course, meant to exemplify not limit the present invention as all size fragments, representing any integer between 10 and the length of an entire nucleotide sequence minus 1, are included in the invention. Additional preferred nucleic acid fragments of the present invention include nucleic acid molecules encoding epitope-bearing portions of E. faecalis polypeptides identified in Table 4.

The present invention also provides for the exclusion of any fragment, specified by 5' and 3' base positions or by size in nucleotide bases as described above for any nucleotide sequence of Table 1 or the plasmid clones listed in Table 1. Any number of fragments of nucleotide sequences in Table 1 or the plasmid clones listed in Table 1, specified by 5' and 3' base positions or by size in nucleotides, as described above, may be excluded from the present invention.

In another aspect, the invention provides an isolated nucleic acid molecule comprising a polynucleotide which hybridizes under stringent hybridization conditions to a portion of a polynucleotide in a nucleic acid molecules of the invention described above, for instance, nucleotide sequences of Table 1 or the E. faecalis sequences of the plasmid clones listed in Table 1. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides bases, and more preferably at least about 20 nucleotides bases, still more preferably at least about 30 nucleotides bases, and even more preferably about 30–70 (e.g., 50) nucleotides bases of the reference polynucleotide. These are useful as diagnostic probes and primers as discussed above. By a portion of a polynucleotide of "at least 20 nucleotides bases in length," for example, is intended 20 or more contiguous nucleotides bases nucleotides from the nucleotide sequence of the reference polynucleotide (e.g., the nucleotide sequence as shown in Table 1). Portions of a polynucleotide which hybridizes to a nucleotide sequence in Table 1, which can be used as probes and primers, may also be precisely specified by 5' and 3' base positions or by size in nucleotide bases as described above or precisely excluded in the same manner.

The nucleic acid molecules of the present invention include those encoding the full length E. faecalis polypeptides of Table 1 and portions of the E. faecalis polypeptides of Table 1. Also included in the present invention are nucleic acids encoding the above full length sequences and further comprise additional sequences, such as those encoding an added secretory leader sequence, such as a pre-, or pro- or prepro- protein sequence. Further included in the present invention are nucleic acids encoding the above full length sequences and portions thereof and further comprise additional heterologous amino acid sequences encoded by nucleic acid sequences from a different source.

Also included in the present invention are nucleic acids encoding the above protein sequences together with additional, non-coding sequences, including for example, but not limited to non-coding 5' and 3' sequences. These sequences include transcribed, non-translated sequences that may play a role in transcription, and mRNA processing, for example, ribosome binding and stability of mRNA. Also included in the present invention are additional coding sequences which provide additional functionalities.

Thus, a nucleotide sequence encoding a polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. For instance, hexa-histidine provides for convenient purification of the fusion protein. See Gentz et al. (1989) Proc. Natl. Acad. Sci. 86:821–24. The "HA" tag is another peptide useful for purification which corresponds to an epitope derived from the influenza hemagglutinin protein. See Wilson et al. (1984) Cell 37:767. As discussed below, other such fusion proteins include the E. faecalis polypeptides of the present invention fused to Fc at the N- or C-terminus.

Variant and Mutant Polynucleotides

The present invention further relates to variants of the nucleic acid molecules which encode portions, analogs or derivatives of a E. faecalis polypeptides of Table 1 and variant polypeptides thereof including portions, analogs, and derivatives of the E. faecalis polypeptides. Variants may occur naturally, such as a natural allelic variant. By an "allelic variant" is intended one of several alternate forms of a gene occupying a given locus on a chromosome of an organism. See, e.g., B. Lewin, Genes IV (1990). Non-naturally occurring variants may be produced using art-known mutagenesis techniques.

Such nucleic acid variants include those produced by nucleotide substitutions, deletions, or additions. The substitutions, deletions, or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of a E. faecalis protein of the present invention or portions thereof. Also especially preferred in this regard are conservative substitutions.

Such polypeptide variants include those produced by amino acid substitutions, deletions or additions. The substitutions, deletions, or additions may involve one or more residues. Alterations may produce conservative or non-conservative amino acid substitutions, deletions, or additions. Especially preferred among these are silent substitutions, additions and deletions, which do not alter the properties and activities of a E. faecalis protein of the present invention or portions thereof. Also especially preferred in this regard are conservative substitutions.

The present invention also relates to recombinant vectors, which include the isolated nucleic acid molecules of the present invention, and to host cells containing the recombinant vectors, as well as to methods of making such vectors and host cells and for using them for production of E. faecalis polypeptides or peptides by recombinant techniques.

The present application is directed to nucleic acid molecules at least 90%, 95%, 96%, 97%, 98% or 99% identical to a nucleic acid sequence shown in Table 1. The above nucleic acid sequences are included irrespective of whether they encode a polypeptide having E. faecalis activity. This is because even where a particular nucleic acid molecule does not encode a polypeptide having E. faecalis activity, one of skill in the art would still know how to use the nucleic acid molecule, for instance, as a hybridization probe. Uses of the nucleic acid molecules of the present invention that do not encode a polypeptide having E. faecalis activity include, inter alia, isolating an E. faecalis gene or allelic variants thereof from a DNA library, and detecting E. faecalis mRNA expression samples, environmental samples, suspected of containing E. faecalis by Northern Blot analysis.

Preferred, are nucleic acid molecules having sequences at least 90%, 95%, 96%, 97%, 98% or 99% identical to the nucleic acid sequence shown in Table 1, which do, in fact, encode a polypeptide having E. faecalis protein activity By "a polypeptide having E. faecalis activity" is intended polypeptides exhibiting activity similar, but not necessarily identical, to an activity of the E. faecalis protein of the invention, as measured in a particular biological assay suitable for measuring activity of the specified protein.

Due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequences shown in Table 1 will encode a polypeptide having E. faecalis protein activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having *E. faecalis* protein activity. This is because the skilled artisan is fully aware of amino acid substitutions that are either less likely or not likely to significantly effect protein function (e.g., replacing one aliphatic amino acid with a second aliphatic amino acid), as further described below.

The biological activity or function of the polypeptides of the present invention are expected to be similar or identical to polypeptides from other bacteria that share a high degree of structural identity/similarity. Tables 2 lists accession numbers and descriptions for the closest matching sequences of polypeptides available through Genbank and Derwent databases. It is therefore expected that the biological activity or function of the polypeptides of the present invention will be similar or identical to those polypeptides from other bacterial genuses, species, or strains listed in Table 2.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the *E. faecalis* polypeptide. In other words, to obtain a polynucleotide having a nucleotide sequence at least 95% identical to a reference nucleotide sequence, up to 5% of the nucleotides in the reference sequence may be deleted, inserted, or substituted with another nucleotide. The query sequence may be an entire sequence shown in Table 1, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. See Brutlag et al. (1990) Comp. App. Biosci. 6:237–245. In a sequence alignment the query and subject sequences are both DNA sequences. An RNA sequence can be compared by first converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only nucleotides outside the 5' and 3' nucleotides of the subject sequence, as displayed by the FASTDB alignment, which are not matched/aligned with the query sequence, are calculated for the purposes of manually adjusting the percent identity score.

For example, a 90 nucleotide subject sequence is aligned to a 100 nucleotide query sequence to determine percent identity. The deletions occur at the 5' end of the subject sequence and therefore, the FASTDB alignment does not show a matched/alignment of the first 10 nucleotides at 5' end. The 10 unpaired nucleotides represent 10% of the sequence (number of nucleotides at the 5' and 3' ends not matched/total number of nucleotides in the query sequence) so 10% is subtracted from the percent identity score calculated by the FASTDB program. If the remaining 90 nucleotides were perfectly matched the final percent identity would be 90%. In another example, a 90 nucleotide subject sequence is compared with a 100 nucleotide query sequence. This time the deletions are internal deletions so that there are no nucleotides on the 5' or 3' of the subject sequence which are not matched/aligned with the query. In this case the percent identity calculated by FASTDB is not manually corrected. Once again, only nucleotides 5' and 3' of the subject sequence which are not matched/aligned with the query sequence are manually corrected for. No other manual corrections are to made for the purposes of the present invention.

Vectors and Host Cell

The present invention also relates to vectors which include the isolated DNA molecules of the present invention, host cells comprising the recombinant vectors, and the production of *E. faecalis* polypeptides and peptides of the present invention expressed by the host cells.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating site at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline, kanamycin, or ampicillin resistance genes for culturing in *E. coli* and other bacteria. Representative examples of appropriate hosts include, but are not limited to, bacterial cells, such as *E. coli*, *Streptomyces* and *Salmonella typhimurium* cells; fungal cells, such as yeast cells; insect cells such as *Drosophila* S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE9, pQE10available from Qiagen; pBS vectors, Phagescript vectors, Bluescript vectors, pNH8A, pNH16a, pNH18A, pNH46A available from Stratagene; pET series of vectors available from Novagen; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lac and lacZ promoters, the T3, T5 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals (for example, Davis, et al., *Basic Methods In Molecular Biology* (1986)).

Transcription of DNA encoding the polypeptides of the present invention by higher eukaryotes may be increased by inserting an enhancer sequence into the vector. Enhancers are cis-acting elements of DNA, usually about from 10 to 300 nucleotides that act to increase transcriptional activity of a promoter in a given host cell-type. Examples of enhancers include the SV40 enhancer, which is located on the late side of the replication origin at nucleotides 100 to 270, the cytomegalovirus early promoter enhancer, the polyoma enhancer on the late side of the replication origin, and adenovirus enhancers.

For secretion of the translated polypeptide into the lumen of the endoplasmic reticulum, into the periplasmic space or into the extracellular environment, appropriate secretion signals may be incorporated into the expressed polypeptide, for example, the amino acid sequence KDEL. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See Bennett, D. et al. (1995) J. Molec. Recogn. 8:52–58 and Johanson, K. et al. (1995) J. Biol. Chem. 270 (16): 9459–9471.

The *E. faecalis* polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography and high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells.

Polypeptides and Fragments

The invention further provides an isolated *E. faecalis* polypeptide having an amino acid sequence in Table 1, or a peptide or polypeptide comprising a portion of the above polypeptides.

Variant and Mutant Polypeptides

To improve or alter the characteristics of *E. faecalis* polypeptides of the present invention, protein engineering may be employed. Recombinant DNA technology known to those skilled in the art can be used to create novel mutant proteins or muteins including single or multiple amino acid substitutions, deletions, additions, or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

It is known in the art that one or more amino acids may be deleted from the N-terminus or C-terminus without substantial loss of biological function. For instance, Ron et al. *J. Biol. Chem.*, 268:2984–2988 (1993), reported modified KGF proteins that had heparin binding activity even if 3, 8, or 27 N-terminal amino acid residues were missing. Accordingly, the present invention provides polypeptides having one or more residues deleted from the amino terminus of the amino acid sequence of the *E. faecalis* polypeptides shown in Table 1, and polynucleotides encoding such polypeptides.

Similarly, many examples of biologically functional C-terminal deletion muteins are known. For instance, Interferon gamma shows up to ten times higher activities by deleting 8–10 amino acid residues from the carboxy terminus of the protein See, e.g., Dobeli, et al. (1988) *J. Biotechnology* 7:199–216. Accordingly, the present invention provides polypeptides having one or more residues from the carboxy terminus of the amino acid sequence of the *E. faecalis* polypeptides shown in Table 1. The invention also provides polypeptides having one or more amino acids deleted from both the amino and the carboxyl termini as described below.

The present invention is further directed to polynucleotide encoding portions or fragments of the amino acid sequences described herein as well as to portions or fragments of the isolated amino acid sequences described herein. Fragments include portions of the amino acid sequences of Table 1, are at least 5 contiguous amino acid in length, are selected from any two integers, one of which representing a N-terminal position. The initiation codon of the polypeptides of the present inventions position 1. Every combination of a N-terminal and C-terminal position that a fragment at least 5 contiguous amino acid residues in length could occupy, on any given amino acid sequence of Table 1 is included in the invention. At least means a fragment may be 5 contiguous amino acid residues in length or any integer between 5 and the number of residues in a full length amino acid sequence minus 1. Therefore, included in the invention are contiguous fragments specified by any N-terminal and C-terminal positions of amino acid sequence set forth in Table 1 wherein the contiguous fragment is any integer between 5 and the number of residues in a full length sequence minus 1.

Further, the invention includes polypeptides comprising fragments specified by size, in amino acid residues, rather than by N-terminal and C-terminal positions. The invention includes any fragment size, in contiguous amino acid residues, selected from integers between 5 and the number of residues in a full length sequence minus 1. Preferred sizes of contiguous polypeptide fragments include about 5 amino acid residues, about 10 amino acid residues, about 20 amino acid residues, about 30 amino acid residues, about 40 amino acid residues, about 50 amino acid residues, about 100 amino acid residues, about 200 amino acid residues, about 300 amino acid residues, and about 400 amino acid residues. The preferred sizes are, of course, meant to exemplify, not limit, the present invention as all size fragments representing any integer between 5 and the number of residues in a full length sequence minus 1 are included in the invention. The present invention also provides for the exclusion of any fragments specified by N-terminal and C-terminal positions or by size in amino acid residues as described above. Any number of fragments specified by N-terminal and C-terminal positions or by size in amino acid residues as described above may be excluded.

The above fragments need not be active since they would be useful, for example, in immunoassays, in epitope mapping, epitope tagging, to generate antibodies to a particular portion of the protein, as vaccines, and as molecular weight markers.

Other Mutants

In addition to N- and C-terminal deletion forms of the protein discussed above, it also will be recognized by one of ordinary skill in the art that some amino acid sequences of the *E. faecalis* polypeptide can be varied without significant effect of the structure or function of the protein. If such differences in sequence are contemplated, it should be remembered that there will be critical areas on the protein which determine activity.

Thus, the invention further includes variations of the *E. faecalis* polypeptides which show substantial *E. faecalis* polypeptide activity or which include regions of *E. faecalis* protein such as the protein portions discussed below. Such mutants include deletions, insertions, inversions, repeats, and type substitutions selected according to general rules known in the art so as to have little effect on activity. For example, guidance concerning how to make phenotypically silent amino acid substitutions is provided. There are two main approaches for studying the tolerance of an amino acid sequence to change. See, Bowie, J. U. et al. (1990), Science 247:1306–1310. The first method relies on the process of evolution, in which mutations are either accepted or rejected by natural selection. The second approach uses genetic engineering to introduce amino acid changes at specific positions of a cloned gene and selections or screens to identify sequences that maintain functionality.

These studies have revealed that proteins are surprisingly tolerant of amino acid substitutions. The studies indicate which amino acid changes are likely to be permissive at a certain position of the protein. For example, most buried amino acid residues require nonpolar side chains, whereas few features of surface side chains are generally conserved. Other such phenotypically silent substitutions are described by Bowie et al. (supra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative, analog, or homolog of the polypeptide of Table 1, or that encoded by the plasmids listed in Table 1, may be: (i) one in which one or more of the amino acid residues are substituted with a conserved or non-conserved amino acid residue (preferably a conserved amino acid residue) and such substituted amino acid residue may or may not be one encoded by the genetic code: or (ii) one in which one or more of the amino acid residues includes a substituent group: or (iii) one in which the *E. faecalis* polypeptide is fused with another compound, such as a compound to increase the half-life of the polypeptide (for example, polyethylene glycol): or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the *E. faecalis* polypeptides of the present invention may include one or more amino acid substitutions, deletions, or additions, either from natural mutations or human manipulation. As indicated, changes are preferably of a minor nature, such as conservative amino acid substitutions that do not significantly affect the folding or activity of the protein (see Table 3).

Amino acids in the *E. faecalis* proteins of the present invention that are essential for function can be identified by methods known in the art, such as site-directed mutagenesis or alanine-scanning mutagenesis. See, e.g., Cunningham et al. (1989) Science 244:1081–1085. The latter procedure introduces single alanine mutations at every residue in the molecule. The resulting mutant molecules are then tested for biological activity using assays appropriate for measuring the function of the particular protein.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic. See, e.g., Pinckard et al., (1967) Clin. Exp. Immunol. 2:331–340; Robbins, et al., (1987) Diabetes 36:838–845; Cleland, et al., (1993) Crit. Rev. Therapeutic Drug Carrier Systems 10:307–377.

The polypeptides of the present invention are preferably provided in an isolated form, and preferably are substantially purified. A recombinantly produced version of the *E. faecalis* polypeptide can be substantially purified by the one-step method described by Smith et al. (1988) Gene 67:31–40. Polypeptides of the invention also can be purified from natural or recombinant sources using antibodies directed against the polypeptides of the invention in methods which are well known in the art of protein purification.

The invention further provides for isolated *E. faecalis* polypeptides comprising an amino acid sequence selected from the group consisting of: (a) the amino acid sequence of a full-length *E. faecalis* polypeptide having the complete amino acid sequence shown in Table 1; (b) the amino acid sequence of a full-length *E. faecalis* polypeptide having the complete amino acid sequence shown in Table 1 excepting the N-terminal methionine; (c) the complete amino acid sequence encoded by the plasmids listed in Table 1; and (d) the complete amino acid sequence excepting the N-terminal methionine encoded by the plasmids listed in Table 1. The polypeptides of the present invention also include polypeptides having an amino acid sequence at least 80% identical, more preferably at least 90% identical, and still more preferably 95%, 96%, 97%, 98% or 99% identical to those described in (a), (b), (c), and (d) above.

Further polypeptides of the present invention include polypeptides which have at least 90% similarity, more preferably at least 95% similarity, and still more preferably at least 96%, 97%, 98% or 99% similarity to those described above.

A further embodiment of the invention relates to a polypeptide which comprises the amino acid sequence of a *E. faecalis* polypeptide having an amino acid sequence which contains at least one conservative amino acid substitution, but not more than 50 conservative amino acid substitutions, not more than 40 conservative amino acid substitutions, not more than 30 conservative amino acid substitutions, and not more than 20 conservative amino acid substitutions. Also provided are polypeptides which comprise the amino acid sequence of a *E. faecalis* polypeptide, having at least one, but not more than 10, 9, 8, 7, 6, 5, 4, 3, 2 or 1 conservative amino acid substitutions.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by the plasmids listed in Table 1 can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., (1990) Comp. App. Biosci. 6:237–245. In a sequence alignment the query and subject sequences are both amino acid sequences. The result of said global sequence alignment is in percent identity. Preferred parameters used in a FASTDB amino acid alignment are: Matrix= PAM 0, k-tuple=2, Mismatch Penalty=1, Joining Penalty= 20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, the results, in percent identity, must be manually corrected. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not match/align with the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other manual corrections are to made for the purposes of the present invention.

The above polypeptide sequences are included irrespective of whether they have their normal biological activity. This is because even where a particular polypeptide molecule does not have biological activity, one of skill in the art would still know how to use the polypeptide, for instance, as a vaccine or to generate antibodies. Other uses of the polypeptides of the present invention that do not have *E. faecalis* activity include, inter alia, as epitope tags, in epitope mapping, and as molecular weight markers on SDS-PAGE gels or on molecular sieve gel filtration columns using methods known to those of skill in the art.

As described below, the polypeptides of the present invention can also be used to raise polyclonal and monoclonal antibodies, which are useful in assays for detecting *E. faecalis* protein expression or as agonists and antagonists capable of enhancing or inhibiting *E. faecalis* protein function. Further, such polypeptides can be used in the yeast two-hybrid system to "capture" *E. faecalis* protein binding proteins which are also candidate agonists and antagonists according to the present invention. See, e.g., Fields et al. (1989) Nature 340:245–246.

Epitope-Bearing Portions

In another aspect, the invention provides peptides and polypeptides comprising epitope-bearing portions of the *E. faecalis* polypeptides of the present invention. These epitopes are immunogenic or antigenic epitopes of the polypeptides of the present invention. An "immunogenic epitope" is defined as a part of a protein that elicits an antibody response when the whole protein or polypeptide is the immunogen. These immunogenic epitopes are believed to be confined to a few loci on the molecule. On the other hand, a region of a protein molecule to which an antibody can bind is defined as an "antigenic determinant" or "antigenic epitope." The number of immunogenic epitopes of a protein generally is less than the number of antigenic epitopes. See, e.g., Geysen, et al. (1983) Proc. Natl. Acad. Sci. USA 81:3998–4002. Predicted antigenic epitopes are shown in Table 4, below. It is pointed out that Table 4 only lists amino acid residues comprising epitopes predicted to have the highest degree of antigenicity. The polypeptides not listed in Table 4 and portions of polypeptides not listed in Table 4 are not considered non-antigenic. This is because they may still be antigenic in vivo but merely not recognized as such by the particular algorithm used. Thus, Table 4 lists the amino acid residues comprising preferred antigenic epitopes but not a complete list. Amino acid residues comprising other antigenic epitopes may be determined by algorithms similar to the Jameson-Wolf analysis or by in vivo testing for an antigenic response using the methods described herein or those known in the art.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, e.g., Sutcliffe, et al., (1983) Science 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. See, Sutcliffe, et al., supra, p. 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. See Sutcliffe, et al., supra, p. 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, e.g., Wilson, et al., (1984) Cell 37:767–778. The anti-peptide antibodies of the invention also are useful for purification of the mimicked protein, for instance, by adsorption chromatography using methods known in the art.

Antigenic epitope-bearing peptides and polypeptides of the invention designed according to the above guidelines preferably contain a sequence of at least seven, more preferably at least nine and most preferably between about 10 to about 50 amino acids (i.e. any integer between 7 and 50) contained within the amino acid sequence of a polypeptide of the invention. However, peptides or polypeptides comprising a larger portion of an amino acid sequence of a polypeptide of the invention, containing about 50 to about 100 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate an *enterococcal*-specific immune response or antibodies include portions of the amino acid sequences identified in Table 1. More specifically, Table 4 discloses a list of non-limiting residues that are involved in the antigenicity of the epitope-bearing fragments of the present invention. Therefore, the present inventions provides for isolated and purified antigenic epitope-bearing fragments of the polypeptides of the present invention comprising a peptide sequences of Table 4. The antigenic epitope-bearing fragments comprising a peptide sequence of Table 4 preferably contain a sequence of at least seven, more preferably at least nine and most preferably between about 10 to about 50 amino acids (i.e. any integer between 7 and 50) of a polypeptide of the present invention. That is, included in the present invention are antigenic polypeptides between the integers of 7 and 50 amino acid in length comprising one or more of the sequences of Table 4. Therefore, in most cases, the polypeptides of Table 4 make up only a portion of the antigenic polypeptide. All combinations of sequences between the integers of 7 and 50 amino acid in length comprising one or more of the sequences of Table 4 are included. The antigenic epitope-bearing fragments may be specified by either the number of contiguous amino acid residues or by specific N-terminal and C-terminal positions as described above for the polypeptide fragments of the present invention, wherein the initiation codon is residue 1. Any number of the described antigenic epitope-bearing fragments of the present invention may also be excluded from the present invention in the same manner.

The epitope-bearing peptides and polypeptides of the invention may be produced by any conventional means for making peptides or polypeptides including recombinant means using nucleic acid molecules of the invention. For instance, an epitope-bearing amino acid sequence of the present invention may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks (Houghten, R. A. Proc. Natl. Acad. Sci. USA 82:5131–5135 (1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously (Houghten et al. (1985) Proc. Natl. Acad. Sci. 82:5131–5135 at 5134.

Epitope-bearing peptides and polypeptides of the invention are used to induce antibodies according to methods well known in the art. See, e.g., Sutcliffe, et al., supra; Wilson, et al., supra; and Bittle, et al. (1985) J. Gen. Virol. 66:2347–2354. Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-malcimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 $\mu$g peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen, et al., supra, discloses a procedure for rapid concurrent synthesis on solid supports of hundreds of peptides of sufficient purity to react in an ELISA. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. supra with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392, to Geysen (1990), describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092, also to Geysen (1989), describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods. The entire disclosure of each document cited in this section on "Polypeptides and Fragments" is hereby incorporated herein by reference.

As one of skill in the art will appreciate, the polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins. (EPA 0,394,827; Traunecker et al. (1988) Nature 331:84–86. Fusion proteins that have a disulfide-linked dimeric structure due to the IgG part can also be more efficient in binding and neutralizing other molecules than a monomeric *E. faecalis* polypeptide or fragment thereof alone. See Fountoulakis et al. (1995) J. Biochem. 270:3958–3964. Nucleic acids encoding the above epitopes of *E. faecalis* polypeptides can also be recombined with a gene of interest as an epitope tag to aid in detection and purification of the expressed polypeptide.

Antibodies

*E. faecalis* protein-specific antibodies for use in the present invention can be raised against the intact *E. faecalis* protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules, single chain whole antibodies, and antibody fragments. Antibody fragments of the present invention include Fab and F(ab')2 and other fragments including single-chain Fvs (scFv) and disulfide-linked Fvs (sdFv). Also included in the present invention are chimeric and humanized monoclonal antibodies and polyclonal antibodies specific for the polypeptides of the present invention. The antibodies of the present invention may be prepared by any of a variety of methods. For example, cells expressing a polypeptide of the present invention or an antigenic fragment thereof can be administered to an animal in order to induce the production of sera containing polyclonal antibodies. For example, a preparation of *E. faecalis* polypeptide or fragment thereof is prepared and purified to render it substantially free of natural contaminants. Such a preparation is then introduced into an animal in order to produce polyclonal antisera of greater specific activity.

In a preferred method, the antibodies of the present invention are monoclonal antibodies or binding fragments thereof. Such monoclonal antibodies can be prepared using hybridoma technology. See, e.g., Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981). Fab and F(ab')2 fragments may be produced by proteolytic cleavage, using enzymes such as papain (to produce Fab fragments) or pepsin (to produce F(ab')$_2$ fragments). Alternatively, *E. faecalis* polypeptide-binding fragments, chimeric, and humanized antibodies can be produced through the application of recombinant DNA technology or through synthetic chemistry using methods known in the art.

Alternatively, additional antibodies capable of binding to the polypeptide antigen of the present invention may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, *E. faecalis* polypeptide-specific antibodies are used to immunize an animal, preferably a mouse. The splenocytes of such an animal are then used to produce hybridoma cells, and the hybridoma cells are screened to identify clones which produce an antibody whose ability to bind to the *E. faecalis* polypeptide-specific antibody can be blocked by the *E. faecalis* polypeptide antigen. Such antibodies comprise anti-idiotypic antibodies to the *E. faecalis* polypeptide-specific antibody and can be used to immunize an animal to induce formation of further *E. faecalis* polypeptide-specific antibodies.

Antibodies and fragments thereof of the present invention may be described by the portion of a polypeptide of the present invention recognized or specifically bound by the antibody. Antibody binding fragments of a polypeptide of the present invention may be described or specified in the same manner as for polypeptide fragments discussed above., i.e, by N-terminal and C-terminal positions or by size in contiguous amino acid residues. Any number of antibody binding fragments, of a polypeptide of the present invention, specified by N-terminal and C-terminal positions or by size in amino acid residues, as described above, may also be excluded from the present invention. Therefore, the present invention includes antibodies the specifically bind a particularly described fragment of a polypeptide of the present invention and allows for the exclusion of the same.

Antibodies and fragments thereof of the present invention may also be described or specified in terms of their cross-reactivity. Antibodies and fragments that do not bind polypeptides of any other species of *Enterococcus* other than *E. faecalis* are included in the present invention. Likewise, antibodies and fragments that bind only species of *Enterococcus*, i.e. antibodies and fragments that do not bind bacteria from any genus other than *Enterococcus*, are included in the present invention.

Diagnostic Assays

The present invention further relates to methods for assaying *enterococcal* infection in an animal by detecting the expression of genes encoding *enterococcal* polypeptides of the present invention. The methods comprise analyzing tissue or body fluid from the animal for *Enterococcus*-specific antibodies, nucleic acids, or proteins. Analysis of nucleic acid specific to *Enterococcus* is assayed by PCR or hybridization techniques using nucleic acid sequences of the present invention as either hybridization probes or primers. See, e.g., Sambrook et al. Molecular cloning: A Laboratory Manual (Cold Spring Harbor Laboratory Press, 2nd ed., 1989, page 54 reference); Eremeeva et al. (1994) J. Clin. Microbiol. 32:803–810 (describing differentiation among spotted fever group Rickettsiae species by analysis of restriction fragment length polymorphism of PCR-amplified DNA) and Chen et al. 1994 J. Clin. Microbiol. 32:589–595 (detecting *B. burgdorferi* nucleic acids via PCR).

Where diagnosis of a disease state related to infection with *Enterococcus* has already been made, the present invention is useful for monitoring progression or regression of the disease state whereby patients exhibiting enhanced *Enterococcus* gene expression will experience a worse clinical outcome relative to patients expressing these gene(s) at a lower level.

By "biological sample" is intended any biological sample obtained from an animal, cell line, tissue culture, or other source which contains *Enterococcus* polypeptide, mRNA, or DNA. Biological samples include body fluids (such as saliva, blood, plasma, urine, mucus, synovial fluid, etc.) tissues (such as muscle, skin, and cartilage) and any other biological source suspected of containing *Enterococcus* polypeptides or nucleic acids. Methods for obtaining biological samples such as tissue are well known in the art.

The present invention is useful for detecting diseases related to *Enterococcus* infections in animals. Preferred animals include monkeys, apes, cats, dogs, birds, cows, pigs, mice, horses, rabbits and humans. Particularly preferred are humans.

Total RNA can be isolated from a biological sample using any suitable technique such as the single-step guanidinium-thiocyanate-phenol-chloroform method described in Chomczynski et al. (1987) Anal. Biochem. 162:156–159. mRNA encoding *Enterococcus* polypeptides having sufficient homology to the nucleic acid sequences identified in Table 1 to allow for hybridization between complementary sequences are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al. (1990) Cell 63:303–312. Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. A *E. faecalis* polynucleotide sequence shown in Table 1 labeled according to any appropriate method (such as the $^{32}$P-multiprimed DNA labeling system (Amersham)) is used as probe. After hybridization overnight, the filter is washed and exposed to x-ray film. DNA for use as probe according to the present invention is described in the sections above and will preferably at least 15 nucleotides in length.

S1 mapping can be performed as described in Fujita et al. (1987) Cell 49:357–367. To prepare probe DNA for use in S1 mapping, the sense strand of an above-described *E. faecalis* DNA sequence of the present invention is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding *Enterococcus* polypeptides).

Levels of mRNA encoding *Enterococcus* polypeptides are assayed, for e.g., using the RT-PCR method described in Makino et al. (1990) Technique 2:295–301. By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the *Enterococcus* polypeptides of the present invention) are quantified using an imaging analyzer. RT and PCR reaction ingredients and conditions, reagent and gel concentrations, and labeling methods are well known in the art. Variations on the RT-PCR method will be apparent to the skilled artisan. Other PCR methods that can detect the nucleic acid of the present invention can be found in PCR PRIMER: A LABORATORY MANUAL (C. W. Dieffenbach et al. eds., Cold Spring Harbor Lab Press, 1995).

The polynucleotides of the present invention, including both DNA and RNA, may be used to detect polynucleotides of the present invention or *Enterococcal* species including *E. faecalis* using bio chip technology. The present invention includes both high density chip arrays (>1000 oligonucleotides per cm$^2$) and low density chip arrays (<1000 oligonucleotides per Cm$^2$). Bio chips comprising arrays of polynucleotides of the present invention may be used to detect *Enterococcal* species, including *E. faecalis*, in biological and environmental samples and to diagnose an animal, including humans, with an *E. faecalis* or other *Enterococcal* infection. The bio chips of the present invention may comprise polynucleotide sequences of other pathogens including bacteria, viral, parasitic, and fungal polynucleotide sequences, in addition to the polynucleotide sequences of the present invention, for use in rapid differential pathogenic detection and diagnosis. The bio chips can also be used to monitor an *E. faecalis* or other *Enterococcal* infections and to monitor the genetic changes (deletions, insertions, mismatches, etc.) in response to drug therapy in the clinic and drug development in the laboratory. The bio chip technology comprising arrays of polynucleotides of the present invention may also be used to simultaneously monitor the expression of a multiplicity of genes, including those of the present invention. The polynucleotides used to comprise a selected array may be specified in the same manner as for the fragments, i.e, by their 5' and 3' positions or length in contiguous base pairs and include from. Methods and particular uses of the polynucleotides of the present invention to detect *Enterococcal* species, including *E. faecalis*, using bio chip technology include those known in the art and those of: U.S. Pat. Nos. 5,510,270, 5,545,531, 5445934, 5677195, 5532128, 5556752, 5527681, 5451683, 5424186, 5607646, 5658732 and World Patent Nos. WO/9710365, WO/9511995, WO/9743447, WO/9535505, each incorporated herein in their entireties.

Biosensors using the polynucleotides of the present invention may also be used to detect, diagnose, and monitor *E. faecalis* or other *Enterococcal* species and infections thereof. Biosensors using the polynucleotides of the present invention may also be used to detect particular polynucleotides of the present invention. Biosensors using the polynucleotides of the present invention may also be used to monitor the genetic changes (deletions, insertions, mismatches, etc.) in response to drug therapy in the clinic and drug development in the laboratory. Methods and particular uses of the polynucleotides of the present invention to detect *Enterococcal* species, including *E. faecalis*, using biosensors include those known in the art and those of: U.S. Pat. Nos. 5,721,102, 5,658,732, 5631170, and World Patent Nos. WO97/3501 1, WO/9720203, each incorporated herein in their entireties.

Thus, the present invention includes both bio chips and biosensors comprising polynucleotides of the present invention and methods of their use.

Assaying *Enterococcus* polypeptide levels in a biological sample can occur using any art-known method, such as antibody-based techniques. For example, *Enterococcus* polypeptide expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of *Enterococcus* polypeptides for Western-blot or dot/slot assay. See, e.g., Jalkanen, M. et al. (1985) J. Cell. Biol. 101:976–985; Jalkanen, M. et al. (1987) J. Cell . Biol. 105:3087–3096. In this technique, which is based on the use of cationic solid phases, quantitation of a *Enterococcus* polypeptide can be accomplished using an isolated *Enterococcus* polypeptide as a standard. This technique can also be applied to body fluids.

Other antibody-based methods useful for detecting *Enterococcus* polypeptide gene expression include immunoassays, such as the ELISA and the radioimmunoassay (RIA). For example, a *Enterococcus* polypeptide-specific monoclonal antibodies can be used both as an immunoabsorbent and as an enzyme-labeled probe to detect and quantify a *Enterococcus* polypeptide. The amount of a *Enterococcus* polypeptide present in the sample can be calculated by reference to the amount present in a standard preparation using a linear regression computer algorithm. Such an ELISA is described in Iacobelli et al. (1988) Breast Cancer Research and Treatment 11:19–30. In another ELISA assay, two distinct specific monoclonal antibodies can be used to detect *Enterococcus* polypeptides in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting the *Enterococcus* polypeptide with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample. Variations of the above and other immunological methods included in the present invention can also be found in Harlow et al., ANTIBODIES: A LABORATORY MANUAL, (Cold Spring Harbor Laboratory Press, 2nd ed. 1988).

Suitable enzyme labels include, for example, those from the oxidize group, which catalyze the production of hydrogen peroxide by reacting with substrate. Glucose oxidize is particularly preferred as it has good stability and its substrate (glucose) is readily available. Activity of an oxidize label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Further suitable labels for the *Enterococcus* polypeptide-specific antibodies of the present invention are provided below. Examples of suitable enzyme labels include malate dehydrogenase, *Enterococcal* nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidize, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging. See, e.g., Perkins et al. (1985) Eur. J. Nucl. Med. 10:296–301; Carasquillo et al. (1987) J. Nucl. Med. 28:281–287. For example, $^{111}$In coupled to monoclonal antibodies with 1-(P-isothiocyanatobenzyl)-DPTA has shown little uptake in non-tumors tissues, particularly the liver, and therefore enhances specificity of tumor localization. See, Esteban et al. (1987) J. Nucl. Med. 28:861–870.

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include, *Pseudomonas* toxin, diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al. (1976) Clin. Chim. Acta 70:1–31, and Schurs et al. (1977) Clin. Chim. Acta 81:1–40. Coupling techniques mentioned in the latter are the glutaraldehyde method, the periodate method, the dimaleimide method, the m-maleimidobenzyl-N-hydroxy-succinimide ester method, all of which methods are incorporated by reference herein.

In a related aspect, the invention includes a diagnostic kit for use in screening serum containing antibodies specific against *E. faecalis* infection. Such a kit may include an isolated *E. faecalis* antigen comprising an epitope which is specifically immunoreactive with at least one anti-*E. faecalis* antibody. Such a kit also includes means for detecting the binding of said antibody to the antigen. In specific embodiments, the kit may include a recombinantly produced or chemically synthesized peptide or polypeptide antigen. The peptide or polypeptide antigen may be attached to a solid support.

In a more specific embodiment, the detecting means of the above-described kit includes a solid support to which said peptide or polypeptide antigen is attached. Such a kit may also include a non-attached reporter-labeled anti-human antibody. In this embodiment, binding of the antibody to the *E. faecalis* antigen can be detected by binding of the reporter labeled antibody to the anti-*E. faecalis* polypeptide antibody.

In a related aspect, the invention includes a method of detecting *E. faecalis* infection in a subject. This detection method includes reacting a body fluid, preferably serum, from the subject with an isolated *E. faecalis* antigen, and examining the antigen for the presence of bound antibody. In a specific embodiment, the method includes a polypeptide antigen attached to a solid support, and serum is reacted with the support. Subsequently, the support is reacted with a reporter-labeled anti-human antibody. The support is then examined for the presence of reporter-labeled antibody.

The solid surface reagent employed in the above assays and kits is prepared by known techniques for attaching protein material to solid support material, such as polymeric beads, dip sticks, 96-well plates or filter material. These attachment methods generally include non-specific adsorption of the protein to the support or covalent attachment of the protein , typically through a free amine group, to a chemically reactive group on the solid support, such as an activated carboxyl, hydroxyl, or aldehyde group. Alternatively, streptavidin coated plates can be used in conjunction with biotinylated antigen(s).

The polypeptides and antibodies of the present invention, including fragments thereof, may be used to detect Enterococcal species including E. faecalis using bio chip and biosensor technology. Bio chip and biosensors of the present invention may comprise the polypeptides of the present invention to detect antibodies, which specifically recognize Enterococcal species, including E. faecalis. Bio chip and biosensors of the present invention may also comprise antibodies which specifically recognize the polypeptides of the present invention to detect Enterococcal species, including E. faecalis or specific polypeptides of the present invention. Bio chips or biosensors comprising polypeptides or antibodies of the present invention may be used to detect Enterococcal species, including E. faecalis, in biological and environmental samples and to diagnose an animal, including humans, with an E. faecalis or other Enterococcal infection. Thus, the present invention includes both bio chips and biosensors comprising polypeptides or antibodies of the present invention and methods of their use.

The bio chips of the present invention may further comprise polypeptide sequences of other pathogens including bacteria, viral, parasitic, and fungal polypeptide sequences, in addition to the polypeptide sequences of the present invention, for use in rapid differential pathogenic detection and diagnosis. The bio chips of the present invention may further comprise antibodies or fragments thereof specific for other pathogens including bacteria, viral, parasitic, and fungal polypeptide sequences, in addition to the antibodies or fragments thereof of the present invention, for use in rapid differential pathogenic detection and diagnosis. The bio chips and biosensors of the present invention may also be used to monitor an E. faecalis or other Enterococcal infection and to monitor the genetic changes (amino acid deletions, insertions, substitutions, etc.) in response to drug therapy in the clinic and drug development in the laboratory. The bio chip and biosensors comprising polypeptides or antibodies of the present invention may also be used to simultaneously monitor the expression of a multiplicity of polypeptides, including those of the present invention. The polypeptides used to comprise a bio chip or biosensor of the present invention may be specified in the same manner as for the fragments, i.e, by their N-terminal and C-terminal positions or length in contiguous amino acid residue. Methods and particular uses of the polypeptides and antibodies of the present invention to detect Enterococcal species, including E. faecalis, or specific polypeptides using bio chip and biosensor technology include those known in the art, those of the U.S. Patent Nos. and World Patent Nos. listed above for bio chips and biosensors using polynucleotides of the present invention, and those of: U.S. Pat. Nos. 5,658,732, 5,135,852, 5567301, 5677196, 5690894 and World Patent Nos. WO9729366, WO9612957, each incorporated herein in their entireties.
Treatment:
Agonists and Antagonists—Assays and Molecules The invention also provides a method of screening compounds to identify those which enhance or block the biological activity of the E. faecalis polypeptides of the present invention. The present invention further provides where the compounds kill or slow the growth of E. faecalis. The ability of E. faecalis antagonists, including E. faecalis ligands, to prophylactically or therapeutically block antibiotic resistance may be easily tested by the skilled artisan. See, e.g., Straden et al. (1997) J Bacteriol. 179(1):9–16.

An agonist is a compound which increases the natural biological function or which functions in a manner similar to the polypeptides of the present invention, while antagonists decrease or eliminate such functions. Potential antagonists include small organic molecules, peptides, polypeptides, and antibodies that bind to a polypeptide of the invention and thereby inhibit or extinguish its activity.

The antagonists may be employed for instance to inhibit peptidoglycan cross bridge formation. Antibodies against E. faecalis may be employed to bind to and inhibit E. faecalis activity to treat antibiotic resistance. Any of the above antagonists may be employed in a composition with a pharmaceutically acceptable carrier.
Vaccines The present invention also provides vaccines comprising one or more polypeptides of the present invention. Heterogeneity in the composition of a vaccine may be provided by combining E. faecalis polypeptides of the present invention. Multi-component vaccines of this type are desirable because they are likely to be more effective in eliciting protective immune responses against multiple species and strains of the Enterococcus genus than single polypeptide vaccines.

Multi-component vaccines are known in the art to elicit antibody production to numerous immunogenic components. See, e.g., Decker et al. (1996) J. Infect. Dis. 174:S270–275. In addition, a hepatitis B, diphtheria, tetanus, pertussis tetravalent vaccine has recently been demonstrated to elicit protective levels of antibodies in human infants against all four pathogenic agents. See, e.g., Aristegui, J. et al. (1997) Vaccine 15:7–9.

The present invention in addition to single-component vaccines includes multi-component vaccines. These vaccines comprise more than one polypeptide, immunogen or antigen. Thus, a multi-component vaccine would be a vaccine comprising more than one of the E. faecalis polypeptides of the present invention.

Further within the scope of the invention are whole cell and whole viral vaccines. Such vaccines may be produced recombinantly and involve the expression of one or more of the E. faecalis polypeptides described in Table 1. For example, the E. faecalis polypeptides of the present invention may be either secreted or localized intracellular, on the cell surface, or in the periplasmic space. Further, when a recombinant virus is used, the E. faecalis polypeptides of the present invention may, for example, be localized in the viral envelope, on the surface of the capsid, or internally within the capsid. Whole cells vaccines which employ cells expressing heterologous proteins are known in the art. See, e.g., Robinson, K. et al. (1997) Nature Biotech. 15:653–657; Sirard, J. et al. (1997) Infect. Immun. 65:2029–2033; Chabalgoity, J. et al. (1997) Infect. Immun. 65:2402-2412. These cells may be administered live or may be killed prior to administration. Chabalgoity, J. et al., supra, for example, report the successful use in mice of a live attenuated Salmonella vaccine strain which expresses a portion of a platyhelminth fatty acid-binding protein as a fusion protein on its cells surface.

A multi-component vaccine can also be prepared using techniques known in the art by combining one or more E. faecalis polypeptides of the present invention, or fragments thereof, with additional non-Enterococcal components (e.g., diphtheria toxin or tetanus toxin, and/or other compounds known to elicit an immune response). Such vaccines are useful for eliciting protective immune responses to both members of the *Enterococcus* genus and non-*Enterococcal* pathogenic agents.

The-vaccines of the present invention also include DNA vaccines. DNA vaccines are currently being developed for a number of infectious diseases. See, et al., Boyer, et al. (1997) Nat. Med. 3:526–532; reviewed in Spier, R. (1996) Vaccine 14:1285–1288. Such DNA vaccines contain a nucleotide sequence encoding one or more *E. faecalis* polypeptides of the present invention oriented in a manner that allows for expression of the subject polypeptide. For example, the direct administration of plasmid DNA encoding *B. burgdorgeri* OspA has been shown to elicit protective immunity in mice against borrelial challenge. See, Luke et al. (1997) J. Infect. Dis. 175:91–97.

The present invention also relates to the administration of a vaccine which is co-administered with a molecule capable of modulating immune responses. Kim et al. (1997) Nature Biotech. 15:641–646, for example, report the enhancement of immune responses produced by DNA immunizations when DNA sequences encoding molecules which stimulate the immune response are co-administered. In a similar fashion, the vaccines of the present invention may be co-administered with either nucleic acids encoding immune modulators or the immune modulators themselves. These immune modulators include granulocyte macrophage colony stimulating factor (GM-CSF) and CD86.

The vaccines of the present invention may be used to confer resistance to *Enterococcal* infection by either passive or active immunization. When the vaccines of the present invention are used to confer resistance to *Enterococcal* infection through active immunization, a vaccine of the present invention is administered to an animal to elicit a protective immune response which either prevents or attenuates a *Enterococcal* infection. When the vaccines of the present invention are used to confer resistance to *Enterococcal* infection through passive immunization, the vaccine is provided to a host animal (e.g., human, dog, or mouse), and the antisera elicited by this antisera is recovered and directly provided to a recipient suspected of having an infection caused by a member of the *Enterococcus* genus.

The ability to label antibodies, or fragments of antibodies, with toxin molecules provides an additional method for treating *Enterococcal* infections when passive immunization is conducted. In this embodiment, antibodies, or fragments of antibodies, capable of recognizing the *E. faecalis* polypeptides disclosed herein, or fragments thereof, as well as other *Enterococcus* proteins, are labeled with toxin molecules prior to their administration to the patient. When such toxin derivatized antibodies bind to *Enterococcus* cells, toxin moieties will be localized to these cells and will cause their death.

The present invention thus concerns and provides a means for preventing or attenuating a *Enterococcal* infection resulting from organisms which have antigens that are recognized and bound by antisera produced in response to the polypeptides of the present invention. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylactic" or "therapeutic" purpose. When provided prophylactically, the compound(s) are provided in advance of any symptoms of *Enterococcal* infection. The prophylactic administration of the compound (s) serves to prevent or attenuate any subsequent infection. When provided therapeutically, the compound(s) is provided upon or after the detection of symptoms which indicate that an animal may be infected with a member of the *Enterococcus* genus. The therapeutic administration of the compound(s) serves to attenuate any actual infection. Thus, the *E. faecalis* polypeptides, and fragments thereof, of the present invention may be provided either prior to the onset of infection (so as to prevent or attenuate an anticipated infection) or after the initiation of an actual infection.

The polypeptides of the invention, whether encoding a portion of a native protein or a functional derivative thereof, may be administered in pure form or may be coupled to a macromolecular carrier. Example of such carriers are proteins and carbohydrates. Suitable proteins which may act as macromolecular carrier for enhancing the immunogenicity of the polypeptides of the present invention include keyhole limpet hemacyanin (KLH) tetanus toxoid, pertussis toxin, bovine serum albumin, and ovalbumin. Methods for coupling the polypeptides of the present invention to such macromolecular carriers are disclosed in Harlow et al., ANTIBODIES: A LABORATORY MANUAL, (Cold Spring Harbor Laboratory Press, 2nd ed. 1988).

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

While in all instances the vaccine of the present invention is administered as a pharmacologically acceptable compound, one skilled in the art would recognize that the composition of a pharmacologically acceptable compound varies with the animal to which it is administered. For example, a vaccine intended for human use will generally not be co-administered with Freund's adjuvant. Further, the level of purity of the *E. faecalis* polypeptides of the present invention will normally be higher when administered to a human than when administered to a non-human animal.

As would be understood by one of ordinary skill in the art, when the vaccine of the present invention is provided to an animal, it may be in a composition which may contain salts, buffers, adjuvants, or other substances which are desirable for improving the efficacy of the composition. Adjuvants are substances that can be used to specifically augment a specific immune response. These substances generally perform two functions: (1) they protect the antigen(s) from being rapidly catabolized after administration and (2) they non-specifically stimulate immune responses.

Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4(SO_4)$, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus Brucella. Other substances useful as adjuvants are the saponins such as, for example, Quil A. (Superfos A/S, Denmark). Preferred adjuvants for use in the present invention include aluminum salts, such as $AlK(SO_4)_2$, $AlNa(SO_4)_2$, and $AlNH_4(SO_4)$. Examples of materials suitable for use in vaccine compositions are provided in REMINGTON'S PHARMACEUTICAL SCIENCES 1324–1341 (A. Osol, ed, Mack Publishing Co, Easton, Pa., (1980) (incorporated herein by reference).

The therapeutic compositions of the present invention can be administered parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

Therapeutic compositions of the present invention can also be administered in encapsulated form. For example, intranasal immunization using vaccines encapsulated in biodegradable microsphere composed of poly(DL-lactide-co-glycolide). See, Shahin, R. et al. (1995) Infect. Immun. 63:1195–1200. Similarly, orally administered encapsulated Salmonella typhimurium antigens can also be used. Allaoui-Attarki, K. et al. (1997) Infect. Immun. 65:853–857. Encapsulated vaccines of the present invention can be administered by a variety of routes including those involving contacting the vaccine with mucous membranes (e.g., intranasally, intracolonicly, intraduodenally).

Many different techniques exist for the timing of the immunizations when a multiple administration regimen is utilized. It is possible to use the compositions of the invention more than once to increase the levels and diversities of expression of the immunoglobulin repertoire expressed by the immunized animal. Typically, if multiple immunizations are given, they will be given one to two months apart.

According to the present invention, an "effective amount" of a therapeutic composition is one which is sufficient to achieve a desired biological effect. Generally, the dosage needed to provide an effective amount of the composition will vary depending upon such factors as the animal's or human's age, condition, sex, and extent of disease, if any, and other variables which can be adjusted by one of ordinary skill in the art.

The antigenic preparations of the invention can be administered by either single or multiple dosages of an effective amount. Effective amounts of the compositions of the invention can vary from 0.01–1,000 µg/ml per dose, more preferably 0.1–500 µg/ml per dose, and most preferably 10–300 µg/ml per dose.

EXAMPLES

Example 1

Isolation of a Selected DNA Clone from the Deposited Sample of E. faecalis

Three approaches can be used to isolate a E. faecalis clone comprising a polynucleotide of the present invention from any E. faecalis genomic DNA library. The E. faecalis strain V586 has been deposited as a convienent source for obtaining a E. faecalis strain although a wide varity of strains E. faecalis strains can be used which are known in the art.

E. faecalis genomic DNA is prepared using the following method. A 20 ml overnight bacterial culture grown in a rich medium (e.g., Trypticase Soy Broth, Brain Heart Infusion broth or Super broth), pelleted, washed two times with TES (30 mM Tris-pH 8.0, 25 mM EDTA, 50 mM NaCl), and resuspended in 5 ml high salt TES (2.5M NaCl). Lysostaphin is added to final concentration of approx 50 ug/ml and the mixture is rotated slowly 1 hour at 37C to make protoplast cells. The solution is then placed in incubator (or place in a shaking water bath) and warmed to 55C. Five hundred micro liter of 20% sarcosyl in TES (final concentration 2%) is then added to lyse the cells. Next, guanidine HCl is added to a final concentration of 7M (3.69 g in 5.5 ml). The mixture is swirled slowly at 55C for 60–90 min (solution should clear). A CsCl gradient is then set up in SW41 ultra clear tubes using 2.0 ml 5.7M CsCl and overlaying with 2.85M CsCl. The gradient is carefully overlayed with the DNA-containing GuHCl solution. The gradient is spun at 30,000 rpm, 20C for 24 hr and the lower DNA band is collected. The volume is increased to 5 ml with TE buffer. The DNA is then treated with protease K (10 ug/ml) overnight at 37 C, and precipitated with ethanol. The precipitated DNA is resuspended in a desired buffer.

In the first method, a plasmid is directly isolated by screening a plasmid E. faecalis genomic DNA library using a polynucleotide probe corresponding to a polynucleotide of the present invention. Particularly, a specific polynucleotide with 30–40 nucleotides is synthesized using an Applied Biosystems DNA synthesizer according to the sequence reported. The oligonucleotide is labeled, for instance, with $^{32}P$-γ-ATP using T4 polynucleotide kinase and purified according to routine methods. (See, e.g., Maniatis et al., Molecular Cloning: A Laboratory Manual, Cold Spring Harbor Press, Cold Spring, N.Y. (1982).) The library is transformed into a suitable host, as indicated above (such as XL-1 Blue (Stratagene)) using techniques known to those of skill in the art. See, e.g., Sambrook et al. MOLECULAR CLONING: A LABORATORY MANUAL (Cold Spring Harbor, N.Y. 2nd ed. 1989); Ausubel et al., CURRENT PROTOCALS IN MOLECULAR BIOLOGY (John Wiley and Sons, N.Y. 1989). The transformants are plated on 1.5% agar plates (containing the appropriate selection agent, e.g., ampicillin) to a density of about 150 transformants (colonies) per plate. These plates are screened using Nylon membranes according to routine methods for bacterial colony screening. See, e.g., Sambrook et al. MOLECULAR CLONING: A LABORATORY MANUAL (Cold Spring Harbor, N.Y. 2nd ed. 1989); Ausubel et al., CURRENT PROTOCALS IN MOLECULAR BIOLOGY (John Wiley and Sons, N.Y. 1989) or other techniques known to those of skill in the art.

Alternatively, two primers of 15–25 nucleotides derived from the 5' and 3' ends of a polynucleotide of Table 1 are synthesized and used to amplify the desired DNA by PCR using a E. faecalis genomic DNA prep as a template. PCR is carried out under routine conditions, for instance, in 25 µl of reaction mixture with 0.5 ug of the above DNA template. A convenient reaction mixture is 1.5–5 mM $MgCl_2$, 0.01% (w/v) gelatin, 20 µM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Finally, overlapping oligos of the DNA sequences of Table 1 can be chemically synthesized and used to generate a nucleotide sequence of desired length using PCR methods known in the art.

Example 2(a):

Expression and Purification *Enterococcal* polypeptides in *E. coli*

The bacterial expression vector pQE60 was used for bacterial expression of some of the polypeptide fragments used in the soft tissue and systemic infection models discussed below. (QIAGEN, Inc., 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin (QIAGEN, Inc., supra) and suitable single restriction enzyme cleavage sites. These elements are arranged such that an inserted DNA fragment encoding a polypeptide expresses that polypeptide with the six His residues (i.e., a "6×His tag") covalently linked to the carboxyl terminus of that polypeptide.

The DNA sequence encoding the desired portion of a *E. faecalis* protein of the present invention was amplified from *E. faecalis* genomic DNA using PCR oligonucleotide primers which anneal to the 5' and 3' sequences coding for the portions of the *E. faecalis* polynucleotide shown in Table 1. Additional nucleotides containing restriction sites to facilitate cloning in the pQE60 vector are added to the 5' and 3' sequences, respectively.

For cloning the mature protein, the 5' primer has a sequence containing an appropriate restriction site followed by nucleotides of the amino terminal coding sequence of the desired *E. faecalis* polynucleotide sequence in Table 1. One of ordinary skill in the art would appreciate that the point in the protein coding sequence where the 5' and 3' primers begin may be varied to amplify a DNA segment encoding any desired portion of the complete protein shorter or longer than the mature form. The 3' primer has a sequence containing an appropriate restriction site followed by nucleotides complementary to the 3' end of the polypeptide coding sequence of Table 1, excluding a stop codon, with the coding sequence aligned with the restriction site so as to maintain its reading frame with that of the six His codons in the pQE60 vector.

The amplified *E. faecalis* DNA fragment and the vector pQE60 were digested with restriction enzymes which recognize the sites in the primers and the digested DNAs were then ligated together. The *E. faecalis* DNA was inserted into the restricted pQE60 vector in a manner which places the *E. faecalis* protein coding region downstream from the IPTG-inducible promoter and in-frame with an initiating AUG and the six histidine codons.

The ligation mixture was transformed into competent *E. coli* cells using standard procedures such as those described by Sambrook et al., supra. *E. coli* strain M15/rep4, containing multiple copies of the plasmid pREP4, which expresses the lac repressor and confers kanamycin resistance ("Kanr"), was used in carrying out the illustrative example described herein. This strain, which was only one of many that are suitable for expressing a *E. faecalis* polypeptide, is available commercially (QIAGEN, Inc., supra). Transformants were identified by their ability to grow on LB agar plates in the presence of ampicillin and kanamycin. Plasmid DNA was isolated from resistant colonies and the identity of the cloned DNA confirmed by restriction analysis, PCR and DNA sequencing.

Clones containing the desired constructs were grown overnight ("O/N") in liquid culture in LB media supplemented with both ampicillin (100 µg/ml) and kanamycin (25 µg/ml). The O/N culture was used to inoculate a large culture, at a dilution of approximately 1:25 to 1:250. The cells were grown to an optical density at 600 nm ("OD600") of between 0.4 and 0.6. Isopropyl-β-D-thiogalactopyranoside ("IPTG") was then added to a final concentration of 1 mM to induce transcription from the lac repressor sensitive promoter, by inactivating the lacI repressor. Cells subsequently were incubated further for 3 to 4 hours. Cells then were harvested by centrifugation.

The cells were then stirred for 3–4 hours at 4° C. in 6M guanidine-HCl, pH 8. The cell debris was removed by centrifugation, and the supernatant containing the *E. faecalis* polypeptide was loaded onto a nickel-nitrilo-tri-acetic acid ("Ni-NTA") affinity resin column (QIAGEN, Inc., supra). Proteins with a 6×His tag bind to the Ni-NTA resin with high affinity were purified in a simple one-step procedure (for details see: The QIAexpressionist, 1995, QIAGEN, Inc., supra). Briefly the supernatant was loaded onto the column in 6 M guanidine-HCl, pH 8, the column was first washed with 10 volumes of 6 M guanidine-HCl, pH 8, then washed with 10 volumes of 6 M guanidine-HCl pH 6, and finally the *E. faecalis* polypeptide was eluted with 6 M guanidine-HCl, pH 5.

The purified protein was then renatured by dialyzing it against phosphate-buffered saline (PBS) or 50 mM Na-acetate, pH 6 buffer plus 200 mM NaCl. Alternatively, the protein could be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM imidazole. Imidazole was removed by a final dialyzing step against PBS or 50 mM sodium acetate pH 6 buffer plus 200 mM NaCl. The purified protein was stored at 4° C. or frozen at −80° C.

Some of the polypeptide of the present invention were prepared using a non-denaturing protein purification method. For these polypeptides, the cell pellet from each liter of culture was resuspended in 25 mls of Lysis Buffer A at 4° C. (Lysis Buffer A=50 mM Na-phosphate, 300 mM NaCl, 10 mM 2-mercaptoethanol, 10% Glycerol, pH 7.5 with 1 tablet of Complete EDTA-free protease inhibitor cocktail (Boehringer Mannheim #1873580) per 50 ml of buffer). Absorbance at 550 nm was approximately 10–20 O.D./ml. The suspension was then put through three freeze/thaw cycles from −70° C. (using a ethanol-dry ice bath) up to room temperature. The cells were lysed via sonication in short 10 sec bursts over 3 minutes at approximately 80W while kept on ice. The sonicated sample was then centrifuged at 15,000 RPM for 30 minutes at 4° C. The supernatant was passed through a column containing 1.0 ml of CL-4B resin to pre-clear the sample of any proteins that may bind to agarose non-specifically, and the flow-through fraction was collected.

The pre-cleared flow-through was applied to a nickel-nitrilo-tri-acetic acid ("Ni-NTA") affinity resin column (Qiagen, Inc., supra). Proteins with a 6× His tag bind to the Ni-NTA resin with high affinity and can be purified in a simple one-step procedure. Briefly, the supernatant was loaded onto the column in Lysis Buffer A at 4° C., the column was first washed with 10 volumes of Lysis Buffer A until the A280 of the eluate returns to the baseline. Then, the column was washed with 5 volumes of 40 mM Imidazole (92% Lysis Buffer A/8% Buffer B) (Buffer B=50 mM Na-Phosphate, 300 mM NaCl, 10% Glycerol, 10 mM 2-mercaptoethanol, 500 mM Imidazole, pH of the final buffer should be 7.5). The protein was eluted off of the column with a series of increasing Imidazole solutions made by adjusting the ratios of Lysis Buffer A to Buffer B. Three different concentrations were used: 3 volumes of 75 mM Imidazole, 3 volumes of 150 mM Imidazole, 5 volumes of 500 mM Imidazole. The fractions containing the purified protein were analyzed using 8%, 10% or 14% SDS-PAGE depending on the protein size. The purified protein was then dialyzed 2× against phosphate-buffered saline (PBS) in order to place it into an easily workable buffer. The purified protein was stored at 4° C. or frozen at −80°.

The following alternative method may be used to purify E. faecalis expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000–6000 psi. The homogenate is then mixed with NaCl solution to a final concentration of 0.5 M NaCl, followed by centrifugation at 7000× g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000× g centrifugation for 15 min., the pellet is discarded and the E. faecalis polypeptide-containing supernatant is incubated at 4° C. overnight to allow further GuHCl extraction.

Following high speed centrifugation (30,000× g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded E. faecalis polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the E. faecalis polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the E. faecalis polypeptide (determined, for instance, by 16% SDS-PAGE) are then pooled.

The resultant E. faecalis polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

Example 2(b)

Alternative Expression and Purification Enterococcal polypeptides in E. coli

The vector pQE10 was alternatively used to clone and express some of the polypeptides of the present invention for use in the soft tissue and systemic infection models discussed below. The difference being such that an inserted DNA fragment encoding a polypeptide expresses that polypeptide with the six His residues (i.e., a "6×His tag") covalently linked to the amino terminus of that polypeptide. The bacterial expression vector pQE10 (QIAGEN, Inc., 9259 Eton Avenue, Chatsworth, Calif., 91311) was used in this example. The components of the pQE10 plasmid are arranged such that the inserted DNA sequence encoding a polypeptide of the present invention expresses the polypeptide with the six His residues (i.e., a "6×His tag")) covalently linked to the amino terminus.

The DNA sequences encoding the desired portions of a polypeptide of Table 1 were amplified using PCR oligonucleotide primers from genomic E. faecalis DNA. The PCR primers anneal to the nucleotide sequences encoding the desired amino acid sequence of a polypeptide of the present invention. Additional nucleotides containing restriction sites to facilitate cloning in the pQE10 vector were added to the 5' and 3' primer sequences, respectively.

For cloning a polypeptide of the present invention, the 5' and 3' primers were selected to amplify their respective nucleotide coding sequences. One of ordinary skill in the art would appreciate that the point in the protein coding sequence where the 5' and 3' primers begins may be varied to amplify a DNA segment encoding any desired portion of a polypeptide of the present invention. The 5' primer was designed so the coding sequence of the 6× His tag is aligned with the restriction site so as to maintain its reading frame with that of E. faecalis polypeptide. The 3' was designed to include an stop codon. The amplified DNA fragment was then cloned, and the protein expressed, as described above for the pQE60 plasmid.

The DNA sequences encoding the amino acid sequences of Table 1 may also be cloned and expressed as fusion proteins by a protocol similar to that described directly above, wherein the pET-32b(+) vector (Novagen, 601 Science Drive, Madison, Wis. 53711) is preferentially used in place of pQE10.

The above methods are not limited to the polypeptide fragments actually produced. The above method, like the methods below, can be used to produce either fill length polypeptides or desired fragments thereof.

Example 2(c)

Alternative Expression and Purification of Enterococcal Polypeptides in *E. coli*

The bacterial expression vector pQE60 is used for bacterial expression in this example (QIAGEN, Inc., 9259 Eton Avenue, Chatsworth, Calif., 91311). However, in this example, the polypeptide coding sequence is inserted such that translation of the six His codons is prevented and, therefore, the polypeptide is produced with no 6×His tag.

The DNA sequence encoding the desired portion of the *E. faecalis* amino acid sequence is amplified from an *E. faecalis* genomic DNA prep the deposited DNA clones using PCR oligonucleotide primers which anneal to the 5' and 3' nucleotide sequences corresponding to the desired portion of the *E. faecalis* polypeptides. Additional nucleotides containing restriction sites to facilitate cloning in the pQE60 vector are added to the 5' and 3' primer sequences.

For cloning a *E. faecalis* polypeptides of the present invention, 5' and 3' primers are selected to amplify their respective nucleotide coding sequences. One of ordinary skill in the art would appreciate that the point in the protein coding sequence where the 5' and 3' primers begin may be varied to amplify a DNA segment encoding any desired portion of a polypeptide of the present invention. The 3' and 5' primers contain appropriate restriction sites followed by nucleotides complementary to the 5' and 3' ends of the coding sequence respectively. The 3' primer is additionally designed to include an in-frame stop codon.

The amplified *E. faecalis* DNA fragments and the vector pQE60 are digested with restriction enzymes recognizing the sites in the primers and the digested DNAs are then ligated together. Insertion of the *E. faecalis* DNA into the restricted pQE60 vector places the *E. faecalis* protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described by Sambrook et al. *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing *E. faecalis* polypeptide, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

To purify the *E. faecalis* polypeptide, the cells are then stirred for 3–4 hours at 4° C. in 6M guanidine-HCl, pH 8. The cell debris is removed by centrifugation, and the supernatant containing the *E. faecalis* polypeptide is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, containing protease inhibitors. After renaturation the protein can be purified by ion exchange, hydrophobic interaction and size exclusion chromatography. Alternatively, an affinity chromatography step such as an antibody column can be used to obtain pure *E. faecalis* polypeptide. The purified protein is stored at 4° C. or frozen at −80° C.

The following alternative method may be used to purify *E. faecalis* polypeptides expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells were then lysed by passing the solution through a microfluidizer (Microfluidics, Corp. or APV Gaulin, Inc.) twice at 4000–6000 psi. The homogenate is then mixed with NaCl solution to a final concentration of 0.5 M NaCl, followed by centrifugation at 7000× g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000× g centrifugation for 15 min., the pellet is discarded and the *E. faecalis* polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded *E. faecalis* polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perspective Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the *E. faecalis* polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the E. faecalis polypeptide (determined, for instance, by 16% SDS-PAGE) are then pooled.

The resultant E. faecalis polypeptide exhibits greater than 95% purity after the above refolding and purification steps. No major contaminant bands are observed from Commassie blue stained 16% SDS-PAGE gel when 5 µg of purified protein is loaded. The purified protein is also tested for endotoxin/LPS contamination, and typically the LPS content is less than 0.1 ng/ml according to LAL assays.

Example 2(d)

Cloning and Expression of E. faecalis in Other Bacteria

E. faecalis polypeptides can also be produced in: E. faecalis using the methods of S. Skinner et al., (1988) Mol. Microbiol. 2:289–297 or J. I. Moreno (1996) Protein Expr. Purif. 8(3):332–340; Lactobacillus using the methods of C. Rush et al., 1997 Appl. Microbiol. Biotechnol. 47(5): 537–542; or in Bacillus subtilis using the methods Chang et al., U.S. Pat. No. 4,952,508.

Example 3

Cloning and Expression in COS Cells

A E. faecalis expression plasmid is made by cloning a portion of the DNA encoding a E. faecalis polypeptide into the expression vector pDNAI/Amp or pDNAIII (which can be obtained from Invitrogen, Inc.). The expression vector pDNAI/amp contains: (1) an E. coli origin of replication effective for propagation in E. coli and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a DNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al. 1984 Cell 37:767. The fusion of the HA tag to the target protein allows easy detection and recovery of the recombinant protein with an antibody that recognizes the HA epitope. pDNAIII contains, in addition, the selectable neomycin marker.

A DNA fragment encoding a E. faecalis polypeptide is cloned into the polylinker region of the vector so that recombinant protein expression is directed by the CMV promoter. The plasmid construction strategy is as follows. The DNA from a E. faecalis genomic DNA prep is amplified using primers that contain convenient restriction sites, much as described above for construction of vectors for expression of E. faecalis in E. coli. The 5' primer contains a Kozak sequence, an AUG start codon, and nucleotides of the 5' coding region of the E. faecalis polypeptide. The 3' primer, contains nucleotides complementary to the 3' coding sequence of the E. faecalis DNA, a stop codon, and a convenient restriction site.

The PCR amplified DNA fragment and the vector, pDNAI/Amp, are digested with appropriate restriction enzymes and then ligated. The ligation mixture is transformed into an appropriate E. coli strain such as SURE™ (Stratagene Cloning Systems, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the E. faecalis polypeptide For expression of a recombinant E. faecalis polypeptide, COS cells are transfected with an expression vector, as described above, using DEAE-dextran, as described, for instance, by Sambrook et al. (supra). Cells are incubated under conditions for expression of E. faecalis by the vector.

Expression of the E. faecalis-HA fusion protein is detected by radiolabeling and immunoprecipitation, using methods described in, for example Harlow et al., supra. To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. (supra). Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 4

Cloning and Expression in CHO Cells

The vector pC4 is used for the expression of E. faecalis polypeptide in this example. Plasmid pC4 is a derivative of the plasmid pSV2-dhfr (ATCC Accession No. 37146). The plasmid contains the mouse DHFR gene under control of the SV40 early promoter. Chinese hamster ovary cells or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented. See, e.g., Alt et al., 1978, J. Biol. Chem. 253:1357–1370; Hamlin et al., 1990, Biochem. et Biophys. Acta, 1097:107–143; Page et al., 1991, Biotechnology 9:64–68. Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains the strong promoter of the long terminal repeat (LTR) of the Rouse Sarcoma Virus, for expressing a polypeptide of interest, Cullen, et al. (1985) Mol. Cell. Biol. 5:438–447; plus a fragment isolated from the enhancer of the immediate early gene of human cytomegalovirus (CMV), Boshart, et al., 1985, Cell 41:521–530. Downstream of the promoter are the following single restriction enzyme cleavage sites that allow the integration of the genes: Bam HI, Xba I, and Asp 718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the E. faecalis polypeptide in a regulated way in mammalian cells (Gossen et al., 1992, Proc. Natl. Acad. Sci. USA 89:5547–5551. For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes and then dephosphorylated using calf intestinal phosphates by procedures known in the art. The vector is then isolated from a 1% agarose gel. The DNA sequence encoding the E. faecalis polypeptide is amplified using PCR oligonucleotide primers corresponding to the 5' and 3' sequences of the desired portion of the gene. A 5' primer containing a restriction site, a Kozak sequence, an AUG start codon, and nucleotides of the 5' coding region of the E. faecalis polypeptide is synthesized and used. A 3' primer, containing a restriction site, stop codon, and nucleotides complementary to the 3' coding sequence of the E. faecalis polypeptides is synthesized and used. The amplified fragment is digested with the restriction endonucleases and then purified again on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using a lipid-mediated transfection agent such as Lipofectin™ or LipofectAMINE.™ (LifeTechnologies Gaithersburg, Md.). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 5

Quantitative Murine Soft Tissue Infection Model for E. faecalis

Compositions of the present invention, including polypeptides and peptides, are assayed for their ability to function as vaccines or to enhance/stimulate an immune response to a bacterial species (e.g., E. faecalis) using the following quantitative murine soft tissue infection model. Mice (e.g., NIH Swiss female mice, approximately 7 weeks old) are first treated with a biologically protective effective amount, or immune enhancing/stimulating effective amount of a composition of the present invention using methods known in the art, such as those discussed above. See, e.g., Harlow et al., ANTIBODIES: A LABORATORY MANUAL, (Cold Spring Harbor Laboratory Press, 2nd ed. 1988). An example of an appropriate starting dose is 20 μg per animal.

The desired bacterial species used to challenge the mice, such as E. faecalis, is grown as an overnight culture. The culture is diluted to a concentration of $5 \times 10^8$ cfu/ml, in an appropriate media, mixed well, serially diluted, and titered. The desired doses are further diluted 1:2 with sterilized Cytodex 3 microcarrier beads preswollen in sterile PBS (3 g/100 ml). Mice are anesthetize briefly until docile, but still mobile and injected with 0.2 ml of the Cytodex 3 bead/bacterial mixture into each animal subcutaneously in the inguinal region. After four days, counting the day of injection as day one, mice are sacrificed and the contents of the abscess is excised and placed in a 15 ml conical tube containing 1.0 ml of sterile PBS. The contents of the abscess is then enzymatically treated and plated as follows.

The abscess is first disrupted by vortexing with sterilized glass beads placed in the tubes. 3.0 mls of prepared enzyme mixture (1.0 ml Collagenase D (4.0 mg/ml), 1.0 ml Trypsin (6.0 mg/ml) and 8.0 mls PBS) is then added to each tube followed by a 20 min. incubation at 37C. The solution is then centrifuged and the supernatant drawn off. 0.5 ml $dH_2O$ is then added and the tubes are vortexed and then incubated for 10 min. at room temperature. 0.5 ml media is then added and samples are serially diluted and plated onto agar plates, and grown overnight at 37C. Plates with distinct and separate colonies are then counted, compared to positive and negative control samples, and quantified. The method can be used to identify composition and determine appropriate and effective doses for humans and other animals by comparing the effective doses of compositions of the present invention with compositions known in the art to be effective in both mice and humans. Doses for the effective treatment of humans and other animals, using compositions of the present invention, are extrapolated using the data from the above experiments of mice. It is appreciated that further studies in humans and other animals may be needed to determine the most effective doses using methods of clinical practice known in the art.

Example 6

Murine Systemic Neutropenic Model for E. faecalis Infection

Compositions of the present invention, including polypeptides and peptides, are assayed for their ability to function as vaccines or to enhance/stimulate an immune response to a bacterial species (e.g., E. faecalis) using the following qualitative murine systemic neutropenic model. Mice (e.g., NIH Swiss female mice, approximately 7 weeks old) are first treated with a biologically protective effective amount, or immune enhancing/stimulating effective amount of a composition of the present invention using methods known in the art, such as those discussed above. See, e.g., Harlow et al., ANTIBODIES: A LABORATORY MANUAL, (Cold Spring Harbor Laboratory Press, 2nd ed. 1988). An example of an appropriate starting dose is 20 ug per animal.

Mice are then injected with 250–300 mg/kg cyclophosphamide intraperitonially. Counting the day of C.P. injection as day one, the mice are left untreated for 5 days to begin recovery of PMNL'S.

The desired bacterial species used to challenge the mice, such as *E. faecalis*, is grown as an overnight culture. The culture is diluted to a concentration of $5 \times 10^8$ cfu/ml, in an appropriate media, mixed well, serially diluted, and titered. The desired doses are further diluted 1:2 in 4% Brewer's yeast in media.

Mice are injected with the bacteria/brewer's yeast challenge intraperitonially. The Brewer's yeast solution alone is used as a control. The mice are then monitored twice daily for the first week following challenge, and once a day for the next week to ascertain morbidity and mortality. Mice remaining at the end of the experiment are sacrificed. The method can be used to identify compositions and determine appropriate and effective doses for humans and other animals by comparing the effective doses of compositions of the present invention with compositions known in the art to be effective in both mice and humans. Doses for the effective treatment of humans and other animals, using compositions of the present invention, are extrapolated using the data from the above experiments of mice. It is appreciated that further studies in humans and other animals may be needed to determine the most effective doses using methods of clinical practice known in the art.

The disclosure of all publications (including patents, patent applications, journal articles, laboratory manuals, books, or other documents) cited herein are hereby incorporated by reference in their entireties.

The present invention is not to be limited in scope by the specific embodiments described herein, which are intended as single illustrations of individual aspects of the invention. Functionally equivalent methods and components are within the scope of the invention, in addition to those shown and described herein and will become apparent to those skilled in the art from the foregoing description and accompanying drawings. Such modifications are intended to fall within the scope of the appended claims.

TABLE 2

Closest matching sequences between the polypeptides of the present invention and sequences in GenBank and Derwent databases.

| Query | GenBank Access. No. | GenBank Gene Description | BLAST Score | BLAST P-Value |
|---|---|---|---|---|
| EF002-2 | gi\|2338759 | (AF018073) periplasmic sorbitol-binding protein; SmoE [Rhodobacter | 113 | 3.60E-18 |
| EF003-2 | gi\|1552773 | hypothetical [*Escherichia coli*] > gnl\|PID\|d1012634 hypothetical 29.4 | 278 | 1.20E-53 |
| EF003-2 | gi\|2196996 | lipoprotein homolog [*Treponema pallidum*] > gi\|2108234 29K protein | 309 | 3.30E-44 |
| EF003-2 | gi\|146649 | lipoprotein-28 precursor [*Escherichia coli*] > gi\|290510 | 263 | 9.20E-40 |
| EF003-2 | gi\|148838 | 28 3kDa membrane protein [*Haemophilus influenzae*] | 197 | 2.10E-39 |
| EF003-2 | gi\|1573614 | 28 kDa membrane protein (hlpA) [*Haemophilus influenzae*] | 197 | 7.80E-39 |
| EF003-2 | gi\|2314748 | (AE000654) outer membrane protein [*Helicobacter pylori*] | 263 | 4.60E-37 |
| EF003-2 | gi\|349530 | lipoprotein [*Pasteurella haemolytica*] > gi\|150508 lipoprotein | 189 | 4.10E-29 |
| EF003-2 | gnl\|PID\|e118435 | similar to hypothetical proteins [*Bacillus subtilis*] | 158 | 2.70E-26 |
| EF003-2 | gi\|349532 | lipoprotein [*Pasteurella haemolytica*] > pir\|JN0753\|JN0753 outer | 200 | 1.20E-25 |
| EF003-2 | gi\|1336657 | lipoprotein [*Bacillus subtilis*] | 182 | 2.70E-25 |
| EF003-2 | gnl\|PID\|e233873 | hypothetical protein [*Bacillus subtilis*] > gnl\|PID\|e1182900 | 186 | 1.30E-23 |
| EF003-2 | gi\|294071 | lipoprotein 3 [*Pasteurella haemolytica*] | 199 | 6.60E-23 |
| EF003-2 | gi\|349531 | lipoprotein [*Pasteurella haemolytica*] > pir\|JN0752\|JN0752 outer | 198 | 1.30E-20 |
| EF003-2 | gi\|294070 | lipoprotein 2 [*Pasteurella haemolytica*] | 198 | 1.80E-20 |
| EF005-2 | gi\|537235 | Kenn Rudd identifies as gpmB [*Escherichia coli*] > gi\|1790856 | 127 | 6.20E-12 |
| EF006-2 | gi\|1552773 | hypothetical [*Escherichia coli*] > gnl\|PID\|d1012634 hypothetical 29.4 | 255 | 1.40E-60 |
| EF006-2 | gi\|349532 | lipoprotein [*Pasteurella haemolytica*] > pir\|JN0753\|JN0753 outer | 221 | 6.40E-49 |
| EF006-2 | gi\|2314748 | (AE000654) outer membrane protein [*Helicobacter pylori*] | 283 | 2.70E-48 |
| EF006-2 | gi\|2196996 | lipoprotein homolog [*Treponema pallidum*] > gi\|2108234 29K protein | 267 | 4.40E-47 |
| EF006-2 | gnl\|PID\|e118435 | similar to hypothetical proteins [*Bacillus subtilis*] | 359 | 1.80E-44 |
| EF006-2 | gi\|349531 | lipoprotein [*Pasteurella haemolytica*] > pir\|JN0752\|JN0752 outer | 218 | 3.80E-41 |
| EF006-2 | gi\|294071 | lipoprotein 3 [*Pasteurella haemolytica*] | 220 | 2.30E-38 |
| EF006-2 | gi\|146649 | lipoprotein-28 precursor [*Escherichia coli*] > gi\|290510 | 193 | 2.60E-38 |
| EF006-2 | gi\|294070 | lipoprotein 2 [*Pasteurella haemolytica*] | 218 | 1.20E-36 |
| EF006-2 | gi\|148838 | 28 3 kDa membrane protein [*Haemophilus influenzae*] | 112 | 8.50E-34 |
| EF006-2 | gi\|1573614 | 28 kDa membrane protein (hlpA) [*Haemophilus influenzae*] | 112 | 1.50E-33 |
| EF006-2 | gi\|349530 | lipoprotein [*Pasteurella haemolytica*] > gi\|150508 lipoprotein | 114 | 4.30E-29 |
| EF006-2 | gi\|294069 | lipoprotein 1 [*Pasteurella haemolytica*] | 114 | 1.30E-27 |
| EF006-2 | gi\|1336657 | lipoprotein [*Bacillus subtilis*] | 202 | 2.10E-26 |
| EF006-2 | gn1\|PID\|e233873 | hypothetical protein [*Bacillus subtilis*] > gnl\|PID\|e1182900 | 200 | 6.50E-25 |
| EF008-2 | gi\|493017 | endocarditis specific antigen [*Enterococcus faecalis*] | 1590 | 2.70E-211 |
| EF008-2 | gi\|393269 | adhesion protein [*Streptococcus pneumoniae*] | 986 | 1.80E-129 |
| EF008-2 | gi\|153834 | adhesin specific for salivary pellicle of dental surfaces | 973 | 1.00E-127 |
| EF008-2 | gi\|1575030 | surface adhesin A precursor [*Streptococcus pneumoniae*] | 934 | 2.90E-126 |
| EF008-2 | gi\|153826 | adhesin B [*Streptococcus sanguis*] > pir\|A43583\|A43583 adhesin B | 916 | 3.90E-126 |
| EF008-2 | gi\|1184932 | ScbA [*Streptococcus crista*] | 915 | 3.40E-125 |
| EF008-2 | gi\|1117994 | surface antigen A variant precursor [*Streptococcus pneumoniae*] | 917 | 5.60E-124 |
| EF008-2 | gi\|310633 | adhesin [*Streptococcus gordonii*] | 891 | 6.00E-122 |
| EF008-2 | gnl\|PID\|e255529 | lipoprotein [*Staphylococcus epidermidis*] | 476 | 1.20E-99 |
| EF008-2 | gi\|1573330 | adhesin B precursor (fimA) [*Haemophilus influenzae*] | 380 | 1.60E-68 |
| EF008-2 | gi\|1245464 | YfeA [*Yersinia pestis*] > gi\|1245464 YfeA [*Yersinia pestis*] | 355 | 1.20E-64 |

TABLE 2-continued

Closest matching sequences between the polypeptides of the present invention and sequences in GenBank and Derwent databases.

| EF008-2 | gi|755075 | periplasmic-binding protein [Synechocystis sp.] > gnl|PID|d1018652 Mn | 321 | 1.70E-62 |
|---|---|---|---|---|
| EF008-2 | gi|1335912 | EwlA [*Erysipelothrix rhusiopathiae*] | 232 | 4.40E-42 |
| EF008-2 | gnl|PID|e118595 | similar to ABC transporter (membrane protein) [Bacillus | 204 | 4.10E-38 |
| EF008-2 | gi|1777933 | TroA [*Treponema pallidum*] | 181 | 2.40E-35 |
| EF009-2 | gi|349531 | lipoprotein [*Pasteurella haemolytica*] > pir|JN0752|JN0752 outer | 391 | 4.00E-64 |
| EF009-2 | gi|1552773 | hypothetical [*Escherichia coli*] > gnl|PID|d1012634 hypothetical 29.4 | 359 | 1.90E-63 |
| EF009-2 | gi|294070 | lipoprotein 2 [*Pasteurella haemolytica*] | 391 | 6.40E-63 |
| EF009-2 | gi|349532 | lipoprotein [*Pasteurella haemolytica*] > pir|JN0753|JN0753 outer | 386 | 1.10E-61 |
| EF009-2 | gi|148838 | 28 3 kDa membrane protein [*Haemophilus influenzae*] | 286 | 5.60E-60 |
| EF009-2 | gi|1573614 | 28 kDa membrane protein (hlpA) [*Haemophilus influenzae*] | 286 | 7.60E-60 |
| EF009-2 | gi|294069 | lipoprotein 1 [*Pasteurella haemolytica*] | 122 | 4.70E-59 |
| EF009-2 | gi|146649 | lipoprotein-28 precursor [*Escherichia coli*] > gi|290510 | 326 | 2.20E-58 |
| EF009-2 | gi|349530 | lipoprotein [*Pasteurella haemolytica*] > gi|150508 lipoprotein | 239 | 7.80E-57 |
| EF009-2 | gi|294071 | lipoprotein 3 [*Pasteurella haemolytica*] | 344 | 4.90E-56 |
| EF009-2 | gi|2314748 | (AE000654) outer membrane protein [*Helicobacter pylori*] | 319 | 4.20E-53 |
| EF009-2 | gi|2196996 | lipoprotein homolog [*Treponema pallidum*] > gi|2108234 29K protein | 312 | 2.60E-41 |
| EF009-2 | gi|1336657 | lipoprotein [*Bacillus subtilis*] | 234 | 4.00E-32 |
| EF009-2 | gnl|PID|e233873 | hypothetical [*Bacillus subtilis*] > gnl|PID|e1182900 | 242 | 1.40E-31 |
| EF009-2 | gnl|PID|e118435 | similar to hypothetical proteins [*Bacillus subtilis*] | 102 | 6.80E-22 |
| EF011-2 | gnl|PID|d100965 | ferric anguibactin-binding protein precursor FatB of V. | 579 | 3.10E-98 |
| EF011-2 | gnl|PID|d100965 | ferric anguibactin-binding protein precursor FatB of V. | 579 | 3.10E-98 |
| EF011-2 | gnl|PID|e185374 | ceuE gene product [*Campylobacter coli*] | 284 | 1.30E-89 |
| EF011-2 | gnl|PID|e185374 | ceuE gene product [*Campylobacter coli*] | 284 | 1.30E-89 |
| EF011-2 | gi|150756 | 40 kDa protein [Plasmid pJM1] > pir|A29928|A29928 membrane-associated | 222 | 2.80E-52 |
| EF011-2 | gi|150756 | 40 kDa protein [Plasmid pJM1] > pir|A29928|A29928 membrane-associated | 222 | 2.80E-52 |
| EF012-2 | gi|309662 | pheromone binding protein [Plasmid pCF10] > pir|B53309|B53309 | 266 | 8.70E-116 |
| EF012-2 | gi|388269 | traC [Plasmid pAD1] > pir|A53310|A53310 pheromone cAD1 binding | 252 | 1.10E-109 |
| EF012-2 | gnl|PID|d101185 | TRAC [*Enterococcus faecalis*] | 281 | 3.60E-103 |
| EF012-2 | gnl|PID|d100655 | TraC [*Enterococcus faecalis*] | 277 | 2.30E-102 |
| EF012-2 | gi|312940 | threonine kinase [*Streptococcus equisimilis*] > pir|S28153|S28153 | 227 | 1.90E-67 |
| EF012-2 | gi|48808 | dciAE [*Bacillus subtilis*] | 228 | 1.70E-46 |
| EF012-2 | pir|S16651|S166 | dciAE protein - Bacillus subtilis | 228 | 1.00E-45 |
| EF012-2 | gnl|PID|e118149 | (AJ002571) DppE [*Bacillus subtilis*] > gnl|PID|e1183316 | 228 | 3.80E-45 |
| EF012-2 | gi|40005 | OppA gene product [*Bacillus subtilis*] | 281 | 3.90E-44 |
| EF012-2 | gi|143603 | sporulation protein [*Bacillus subtilis*] > gnl|PID|e1183163 | 281 | 7.70E-44 |
| EF012-2 | gnl|PID|d101563 | Periplasmic oligopeptide-binding protein precursor. | 152 | 2.20E-43 |
| EF012-2 | gi|1574679 | oligopeptide binding protein (oppA) [*Haemophilus influenzae*] | 178 | 2.20E-42 |
| EF012-2 | gi|47802 | Opp A (AA1-542) [*Salmonella typhimurium*] > gi|47808 precursor | 128 | 1.00E-37 |
| EF012-2 | gi|882550 | ORF_f535 [*Escherichia coli*] > gi|1789397 (AE000384) f535; This 535 aa | 228 | 5.30E-36 |
| EF014-2 | pir|D70070|D700 | transcriptional regulator homolog ywtF - Bacillus subtilis | 101 | 1.40E-27 |
| EF014-2 | gnl|PID|e116988 | capsular polysaccharide synthesis protein [Streptococcus | 121 | 9.50E-27 |
| EF014-2 | gi|2804769 | (AF030373) putative regulatory protein [*Streptococcus pneumoniae*] | 121 | 9.50E-27 |
| EF014-2 | gnl|PID|e289126 | unknown [*Streptococcus pneumoniae*] | 121 | 1.00E-24 |
| EF014-2 | gi|2267239 | ORF1 [*Staphylococcus epidermidis*] | 234 | 1.50E-24 |
| EF014-2 | gi|485275 | putative regulatory protein [*Streptococcus pneumoniae*] | 121 | 3.90E-24 |
| EF014-2 | gi|2804735 | (AF030367) putative regulatory protein [*Streptococcus pneumoniae*] | 121 | 3.90E-24 |
| EF014-2 | gi|2804747 | (AF030369) putative regulatory protein [*Streptococcus pneumoniae*] | 121 | 3.90E-24 |
| EF014-2 | gi|1762327 | putative transcriptional regulator [*Bacillus subtilis*] | 185 | 2.80E-22 |
| EF014-2 | gi|143156 | membrane bound protein [*Bacillus subtilis*] > gnl|PID|e1184471 | 116 | 1.10E-21 |
| EF014-2 | gnl|PID|d101895 | membrane bound protein LytR [Synechocystis sp.] | 113 | 6.20E-20 |
| EF014-2 | gi|1276874 | EpsA [*Streptococcus thermophilus*] | 103 | 4.00E-17 |
| EF016-2 | gnl|PID|e118566 | similar to amino acid ABC transporter (binding protein) | 194 | 3.70E-35 |
| EF016-2 | gi|40934 | arginine binding protein [*Escherichia coli*] > gi|769794 artJ | 121 | 1.60E-31 |
| EF016-2 | gnl|PID|d101527 | Arginine-binding periplasmic protein 2 precursor [Escherichia | 121 | 4.80E-31 |
| EF016-2 | gi|687652 | FLiY [*Escherichia coli*] > gnl|PID|d1016464 FliY protein precursor. | 160 | 5.70E-31 |
| EF016-2 | gi|2650410 | (AE001090) glutamine ABC transporter, periplasmic glutamine-binding | 122 | 3.30E-29 |
| EF016-2 | gi|1649035 | high-affinity periplasmic glutamine binding protein [Salmonella | 104 | 1.80E-27 |
| EF016-2 | gi|1574634 | glutamine-binding periplasmic protein (glnH) [*Haemophilus* | 174 | 2.50E-27 |
| EF016-2 | gi|41569 | GlnH precursor (AA -22 to 226) [*Escherichia coli*] > gnl|PID|d1015250 | 106 | 4.70E-27 |
| EF016-2 | gnl|PID|d101527 | Arginine-binding periplasmic protein 1 precursor [Escherichia | 109 | 3.70E-26 |
| EF016-2 | gi|769791 | artI [*Escherichia coli*] > gi|769791 artI [*Escherichia coli*] | 127 | 2.30E-25 |
| EF016-2 | gnl|PID|d100892 | homologous to Gln-binding periplasmic proteins [Bacillus | 117 | 8.50E-24 |
| EF016-2 | gi|154125 | J protein [*Salmonella typhimurium*] > gi|47718 reading frame hisJ | 118 | 2.10E-23 |
| EF016-2 | gnl|PID|d101688 | HISTIDINE-BINDING PERIPLASMIC PROTEIN PRECURSOR (HBP). | 117 | 4.50E-23 |
| EF016-2 | gi|1166636 | histidine-binding periplasmic protein HisJ [*Escherichia coli*] | 117 | 6.60E-23 |
| EF017-2 | gi|388269 | traC [Plasmid pAD1] > pir|A53310|A53310 pheromone cAD1 binding | 421 | 4.50E-128 |
| EF017-2 | gnl|PID|d101185 | TRAC [*Enterococcus faecalis*] | 417 | 5.10E-124 |
| EF017-2 | gnl|PID|d100655 | TraC [*Enterococcus faecalis*] | 414 | 4.40E-123 |
| EF017-2 | gi|309662 | pheromone binding protein [Plasmid pCF10] > pir|B53309|B53309 | 415 | 2.40E-119 |
| EF017-2 | gi|40005 | OppA gene product [*Bacillus subtilis*] | 294 | 6.20E-82 |
| EF017-2 | gi|143603 | sporulation protein [*Bacillus subtilis*] > gnl|PID|e1183163 | 290 | 2.80E-79 |
| EF017-2 | gi|312940 | threonine kinase [*Streptococcus equisimilis*] > pir|S28153|S28153 | 241 | 2.40E-71 |
| EF017-2 | gi|48808 | dciAE [*Bacillus subtilis*] | 270 | 1.10E-61 |
| EF017-2 | gnl|PID|e118149 | (AJ002571) DppE [*Bacillus subtilis*] > gnl|PID|e1183316 | 270 | 1.50E-61 |
| EF017-2 | pir|S16651|S166 | dciAE protein - Bacillus subtilis | 270 | 3.10E-60 |
| EF017-2 | gi|304925 | periplasmic oligopeptide binding protein [*Escherichia coli*] | 171 | 2.60E-57 |
| EF017-2 | gi|147014 | oligopeptide binding protein precursor [*Escherichia coli*] | 171 | 8.70E-56 |

TABLE 2-continued

Closest matching sequences between the polypeptides of the present invention and sequences in GenBank and Derwent databases.

| | | | | |
|---|---|---|---|---|
| EF017-2 | gi\|47802 | Opp A (AA1-542) [*Salmonella typhimurium*] > gi\|47808 precursor | 154 | 1.30E-52 |
| EF017-2 | gi\|882550 | ORF f535 [*Escherichia coli*] > gi\|1789397 (AE000384) f535; This 535 aa | 135 | 5.50E-52 |
| EF017-2 | gi\|1574679 | oligopeptide binding protein (oppA) [*Haemophilus influenzae*] | 168 | 2.90E-43 |
| EF019-2 | gi\|438458 | likely N-terminal signal sequence; mature protein probably | 104 | 2.30E-17 |
| EF021-2 | gnl\|PID\|e311492 | unknown [*Bacillus subtilis*] > gnl\|PID\|e1184232 similar to ABC | 317 | 2.50E-103 |
| EF021-2 | bbs\|173803 | CD4+ T cell-stimulating antigen [*Listeria monocytogenes*, 85EO-1167, | 476 | 2.80E-81 |
| EF021-2 | gi\|581809 | tmbC gene product [*Treponema pallidum*] > pir\|A43595\|A43595 membrane | 152 | 3.20E-71 |
| EF021-2 | gi\|2688280 | (AB001143) basic membrane protein C (bmpC) [*Borrelia burgdorferi*] | 101 | 5.50E-27 |
| EF021-2 | gnl\|PID\|e117283 | membrane protein A [*Borrelia garinii*] | 142 | 6.50E-22 |
| EF021-2 | gnl\|PID\|e117283 | membrane protein A [*Borrelia burgdorferi*] | 141 | 9.20E-22 |
| EF021-2 | gnl\|PID\|e117283 | membrane protein A [*Borrelia burgdorferi*] > gi\|516592 membrane | 141 | 9.20E-22 |
| EF021-2 | gnl\|PID\|e117282 | bmpA(p39,ORF1) [*Borrelia burgdorferi*] | 141 | 1.70E-21 |
| EF021-2 | gi\|508421 | antigen P39 [*Borrelia burgdorferi*] > gi\|2688281 (AE001143) basic | 141 | 1.70E-21 |
| EF021-2 | gi\|1753225 | BmpA protein [*Borrelia burgdorferi*] | 141 | 2.70E-20 |
| EF021-2 | gnl\|PID\|e117283 | membrane protein A [*Borrelia afzelii*] | 141 | 8.60E-20 |
| EF021-2 | gnl\|PID\|e117283 | membrane protein A [*Borrelia afzelii*] | 141 | 8.60E-20 |
| EF021-2 | gnl\|PID\|e117283 | membrane protein A [*Borrelia afzelii*] | 141 | 8.60E-20 |
| EF021-2 | gnl\|PID\|e117282 | bmpA(p39, ORF1) [*Borrelia burgdorferi*] | 141 | 1.50E-19 |
| EF022-2 | gi\|312940 | threonine kinase [*Streptococcus equisimilis*] > pir\|S28153\|S28153 | 324 | 5.90E-66 |
| EF022-2 | gi\|309662 | pheromone binding protein [Plasmid pCF10] > pir\|B53309\|B53309 | 307 | 5.60E-60 |
| EF022-2 | gnl\|PID\|d101185 | TRAC [*Enterococcus faecalis*] | 301 | 4.80E-59 |
| EF022-2 | gnl\|PID\|e118149 | (AJ002571) DppE [*Bacillus subtilis*] > gnl\|PID\|e1183316 | 170 | 5.10E-59 |
| EF022-2 | gi\|48808 | dciAE [*Bacillus subtilis*] | 170 | 5.20E-59 |
| EF022-2 | gnl\|PID\|d100655 | TraC [*Enterococcus faecalis*] | 299 | 2.80E-58 |
| EF022-2 | pir\|S16651\|S166 | dciAE protein - *Bacillus subtilis* | 170 | 1.60E-57 |
| EF022-2 | gi\|388269 | traC [Plasmid pAD1] > pir\|1A53310\|A53310 pheromone cAD1 binding | 280 | 2.70E-53 |
| EF022-2 | gi\|40005 | OppA gene product [*Bacillus subtilis*] | 154 | 7.30E-48 |
| EF022-2 | gi\|143603 | sporulation protein [*Bacillus subtilis*] > gnl\|PID\|e1183163 | 154 | 3.10E-47 |
| EF022-2 | gi\|2688227 | (AE001139) oligopeptide ABC transporter, periplasmic | 215 | 1.00E-36 |
| EF022-2 | gi\|2281458 | (AF000366) oligopeptide permease homolog AII [*Borrelia burgdorferi*] | 215 | 1.00E-36 |
| EF022-2 | gi\|304925 | periplasmic oligopeptide binding protein [*Escherichia coli*] | 131 | 1.30E-35 |
| EF022-2 | gi\|147014 | oligopeptide binding protein precursor [*Escherichia coli*] | 131 | 1.80E-34 |
| EF022-2 | gi\|47802 | Opp A (AA1-542) [*Salmonella typhimurium*] > gi\|47808 precursor | 138 | 4.90E-34 |
| EF023-2 | gi\|309662 | pheromone binding protein [Plasmid pCF10] > pir\|B53309\|B53309 | 231 | 4.70E-66 |
| EF023-2 | gi\|388269 | traC [Plasmid pAD1] > pir\|A53310\|A53310 pheromone cAD1 binding | 223 | 4.80E-62 |
| EF023-2 | gnl\|PID\|d101185 | TRAC [*Enterococcus faecalis*] | 226 | 1.00E-58 |
| EF023-2 | gnl\|PID\|d100655 | TraC [*Enterococcus faecalis*] | 226 | 4.40E-58 |
| EF023-2 | gi\|48808 | dciAE [*Bacillus subtilis*] | 157 | 1.20E-57 |
| EF023-2 | gnl\|PID\|e118149 | (AJ002571) DppE [*Bacillus subtilis*] > gnl\|PID\|e1183316 | 157 | 120E-57 |
| EF023-2 | pir\|S16651\|S166 | dciAE protein - [*Bacillus subtilis*] | 157 | 3.80E-56 |
| EF023-2 | gi\|40005 | OppA gene product [*Bacillus subtilis*] | 137 | 2.30E-53 |
| EF023-2 | gi\|143603 | sporulation protein [*Bacillus subtilis*] > gnl\|PID\|e1183163 | 133 | 6.90E-53 |
| EF023-2 | gi\|47802 | Opp A (AA1-542) [*Salmonella typhimurium*] > gi\|47808 precursor | 135 | 2.20E-41 |
| EF023-2 | gi\|2688227 | (AB001139) oligopeptide ABC transporter, periplasmic | 187 | 9.40E-41 |
| EF023-2 | gi\|2281458 | (AF000366) oligopeptide permease homolog AII [*Borrelia burgdorferi*] | 187 | 1.90E-40 |
| EF023-2 | gi\|882550 | ORF_f535 [*Escherichia coli*] > gi\|1789397 (AE000384) f535; This 535 aa | 155 | 1.30E-38 |
| EF023-2 | gi\|304925 | periplasmic oligopeptide binding protein [*Escherichia coli*] | 130 | 9.00E-37 |
| EF023-2 | gi\|147014 | oligopeptide binding protein precursor [*Escherichia coli*] | 130 | 3.70E-34 |
| EF026-2 | gi\|2352482 | (AF005097) unknown [*Lactococcus lactis*] | 141 | 1.10E-23 |
| EF027-2 | gi\|309662 | pheromone binding protein [Plasmid pCF 10] > pir\|B53309\|B53309 | 198 | 6.20E-71 |
| EF027-2 | gnl\|PID\|d100655 | TraC [*Enterococcus faecalis*] | 202 | 1.50E-68 |
| EF027-2 | gnl\|PID\|d101185 | TRAC [*Enterococcus faecalis*] | 202 | 1.50E-68 |
| EF027-2 | gi\|388269 | traC [Plasmid pAD1] > pir\|A53310\|A53310 pheromone cAD1 binding | 213 | 8.30E-68 |
| EF027-2 | gnl\|PID\|e118149 | (AJ002571) DppE [*Bacillus subtilis*] > gnl\|PID\|e1183316 | 222 | 3.70E-41 |
| EF027-2 | gi\|48808 | dciAE [*Bacillus subtilis*] | 222 | 4.90E-41 |
| EF027-2 | pir\|S16651\|S166 | dciAE protein - *Bacillus subtilis* | 222 | 1.10E-39 |
| EF027-2 | gi\|40005 | OppA gene product [*Bacillus subtilis*] | 251 | 4.10E-39 |
| EF027-2 | gi\|143603 | sporulation protein [*Bacillus subtilis*] > gnl\|PID\|e1183163 | 247 | 5.80E-39 |
| EF027-2 | gi\|312940 | threonine kinase [*Streptococcus equisimilis*] > pir\|S28153\|S28153 | 233 | 8.90E-33 |
| EF027-2 | gi\|2688227 | (AE001139) oligopeptide ABC transporter, periplasmic | 131 | 2.40E-24 |
| EF027-2 | gi\|2281458 | (AF000366) oligopeptide permease homolog AII [*Borrelia burgdorferi*] | 131 | 2.40E-24 |
| EF027-2 | gi\|2281468 | (AF000948) OppAIV [*Borrelia burgdorferi*] > gi\|2689891 (AB000792) | 117 | 3.00E-20 |
| EF027-2 | gi\|1574679 | oligopeptide binding protein (oppA) [*Haemophilus influenzae*] | 130 | 3.50E-20 |
| EF028-2 | gnl\|PID\|d102047 | B.subtilis alkaline phosphatase IIIA; P19405 secretory | 996 | 3.60E-131 |
| EF028-2 | pir\|B39096\|B390 | alkaline phosphatase (EC 3.1.3.1) III precursor - Bacillus | 982 | 2.90E-129 |
| EF028-2 | gi\|470383 | alkaline phosphatase A [*Bacillus subtilis*] > gnl\|PID\|e1182942 | 803 | 4.80E-119 |
| EF028-2 | gi\|143324 | APase I [*Bacillus licheniformis*] > pir\|A44828\|A44828 alkaline | 184 | 3.00E-54 |
| EF028-2 | gi\|147243 | alkaline phosphatase precursor (EC 3.1.3.1) [*Escherichia coli*] | 183 | 8.30E-54 |
| EF028-2 | gi\|147237 | alkaline phosphatase precursor (EC 3.1.3.1) [*Escherichia coli*] | 178 | 4.40E-53 |
| EF028-2 | gi\|147239 | alkaline phosphatase precursor (EC 3.1.3.1) [*Escherichia coli*] | 178 | 4.40E-53 |
| EF028-2 | gi\|147241 | alkaline phosphatase precursor (EC 3.1.3.1) [*Escherichia coli*] | 178 | 4.40E-53 |
| EF028-2 | gi\|1277127 | phoA gene product [Cloning vector pFW_phoAI] > gi\|1277130 phoA gene | 174 | 4.90E-53 |
| EF028-2 | gi\|147229 | alkaline phosphatase precursor (EC 3.1.3.1) [*Escherichia coli*] | 178 | 8.40B-53 |
| EF028-2 | gi\|818851 | alkaline phosphatase [synthetic construct] | 174 | 1.10E-52 |
| EF028-2 | gi\|147245 | alkaline phosphatase (phoA) (EC 3.1.3.1) [*Escherichia fergusonii*] | 177 | 1.20E-52 |
| EF028-2 | gi\|147231 | alkaline phosphatase precursor (EC 3.1.3.1) [*Escherichia coli*] | 174 | 1.60E-52 |
| EF028-2 | gi\|147235 | alkaline phosphatase precursor (EC 3.1.3.1) [*Escherichia coli*] | 174 | 1.60E-52 |

TABLE 2-continued

Closest matching sequences between the polypeptides of the present invention and sequences in GenBank and Derwent databases.

| | | | | |
|---|---|---|---|---|
| EF028-2 | gi\|1016010 | alkaline phosphatase with N-terminal PeiB-leader and C-terminal | 174 | 1.60E-52 |
| EF029-2 | gi\|1750126 | YncB [*Bacillus subtilis*] > gnl\|PID\|e1183421 similar to micrococcal | 257 | 3.50E-55 |
| EF029-2 | gnl\|PID\|e118360 | similar to hypothetical proteins [*Bacillus subtilis*] | 263 | 7.80E-53 |
| EF029-2 | gi\|673492 | nuclease [*Staphylococcus aureus*] > pir\|A00790\|NCSAF micrococcal | 320 | 2.20E-39 |
| EF029-2 | gi\|532653 | thermonuclease [*Staphylococcus hyicus*] | 155 | 9.10E-39 |
| EF029-2 | gi\|47146 | thermonuclease [*Staphylococcus intermedius*] > pir\|S26079\|S26079 | 145 | 4.90E-3 2 |
| EF030-2 | gi\|48808 | dciAE [*Bacillus subtilis*] | 149 | 1.10E-66 |
| EF030-2 | gnl\|PID\|e118149 | (AJ002571) DppE [*Bacillus subtilis*] > gnl\|PID\|e1183316 | 149 | 1.50E-66 |
| EF030-2 | pir\|S16651\|S166 | dciAE protein - *Bacillus subtilis* | 149 | 5.90E-66 |
| EF030-2 | gi\|309662 | pheromone binding protein [Plasmid pCF10] >pir\|B53309\|B53309 | 227 | 7.40E-52 |
| EF030-2 | gnl\|PID\|d101185 | TRAC [*Enterococcus faecalis*] | 237 | 7.40E-52 |
| EF030-2 | gnl\|PID d100655 | TraC [*Enterococcus faecalis*] | 233 | 9.70E-51 |
| EF030-2 | gi\|388269 | traC [Plasmid pAD1] > pir\|A53310\|A53310 pheromone cAD1 binding | 229 | 3.00E-48 |
| EF030-2 | gi\|312940 | threonine kinase [*Streptococcus equisimilis*] > pir\|S28153\|S28153 | 277 | 3.00E-45 |
| EF030-2 | gi\|47802 | Opp A (AA1-542) [*Salmonella typhimurium*] > gi\|47808 precursor | 125 | 8.50E-34 |
| EF030-2 | gi\|2688227 | (AE001139) oligopeptide ABC transporter, periplasmic | 211 | 4.80E-31 |
| EF030-2 | gi\|2281458 | (AF000366) oligopeptide permease homolog AII [*Borrelia burgdorferi*] | 211 | 4.80E-31 |
| EF030-2 | gi\|40005 | OppA gene product [*Bacillus subtilis*] | 148 | 1.20E-30 |
| EF030-2 | gi\|143603 | sporulation protein [*Bacillus subtilis*] > gnl\|PID\|e1183163 | 144 | 4.80E-30 |
| EF030-2 | gi\|2281468 | (AF000948) OppAIV [*Borrelia burgdorferi*] > gi\|2689891 (AE000792) | 210 | 2.10E-29 |
| EF030-2 | gi\|1574679 | oligopeptide binding protein (oppA) [*Haemophilus influenzae*] | 148 | 6.00E-29 |
| EF033-2 | gnl\|PID\|e118439 | similar to iron-binding protein [*Bacillus subtilis*] | 164 | 2.60E-14 |
| EF033-2 | pir\|S54437\|S544 | hemin binding protein - *Yersinia enterocolitica* | 108 | 1.40E-11 |
| EF033-2 | gi\|1619623 | hemin binding protein [*Yersinia enterocolitica*] | 108 | 2.00E-11 |
| EF036-2 | gnl\|PID\|d101022 | ORF108 [*Bacillus subtilis*] > gnl\|PID\|e1185766 alternate gene | 544 | 1.20E-96 |
| EF036-2 | gi\|2622858 | (AE000929) phosphate-binding protein PstS [Methanobacterium | 183 | 1.40E-45 |
| EF036-2 | gi\|2622859 | (AE000929) phosphate-binding protein PstS homolog [Methanobacterium | 158 | 2.40E-41 |
| EF036-2 | gi\|2688115 | (AE001132) phosphate ABC transporter, periplasmic phosphate-binding | 117 | 1.10E-12 |
| EF037-2 | gi\|2352482 | (AF005097) unknown [*Lactococcus lactis*] | 141 | 1.10E-23 |
| EF040-2 | gi\|1657516 | hypothetical protein [*Escherichia coli*] > gi\|1786511 (AE000139) | 208 | 1.90E-29 |
| EF040-2 | gi\|293265 | 2-5A-dependent RNase [*Mus musculus*] > pir\|B45771\|B45771 | 105 | 1.00E-17 |
| EF040-2 | gi\|287865 | G9a [*Homo sapiens*] > pir\|S30385\|S30385 G9a protein - human | 143 | 8.30E-14 |
| EF040-2 | gi\|311817 | erythroid ankyrin [*Mus musculus*] > pir\|S37771\|S37771 ankyrin, | 119 | 4.80E-13 |
| EF040-2 | gi\|191940 | ankyrin [*Mus musculus*] > pir\|I49502\|I49502 ankyrin - mouse | 119 | 4.90E-13 |
| EF040-2 | gi\|747710 | alt. ankyrin (variant 2.2) [*Homo sapiens*] | 120 | 1.50E-12 |
| EF040-2 | gi\|178646 | ankyrin [*Homo sapiens*] | 120 | 1.80E-12 |
| EF040-2 | gi\|1845265 | ankyrin [*Homo sapiens*] | 120 | 1.80E-12 |
| EF040-2 | pir\|A35049\|A350 | ankyrin 1, erythrocyte splice form 2 - human | 120 | 1.80E-12 |
| EF040-2 | pir\|B35049\|B350 | ankyrin 1, erythrocyte splice form 3 - human | 120 | 1.80E-12 |
| EF040-2 | gi\|28702 | ankyrin (variant 2.1) [*Homo sapiens*] > pir\|S08275\|SJHUK ankyrin 1, | 120 | 1.80E-12 |
| EF041-2 | gi\|388269 | traC [Plasmid pAD1] > pir\|A53310\|A53310 pheromone cAD1 binding | 670 | 1.40E-87 |
| EF041-2 | gnl\|PID\|d100655 | TraC [*Enterococcus faecalis*] | 662 | 1.50E-85 |
| EF041-2 | gnl\|PID\|d101185 | TRAC [*Enterococcus faecalis*] | 662 | 1.50E-85 |
| EF041-2 | gi\|309662 | pheromone binding protein [Plasmid pCF10] > pir\|1B53309\|B53309 | 648 | 1.20E-83 |
| EF041-2 | gi\|48808 | dciAE [*Bacillus subtilis*] | 218 | 1.20E-57 |
| EF041-2 | gnl\|PID\|e118149 | (AJ002571) DppE [*Bacillus subtilis*] > gnl\|PID\|e1183316 | 218 | 1.40E-57 |
| EF041-2 | pir\|S16651\|S166 | dciAE protein - *Bacillus subtilis* | 218 | 2.10E-56 |
| EF041-2 | gi\|882550 | ORF_f535 [*Escherichia coli*] > gi\|1789397 (AE000384) f535; This 535 aa | 146 | 7.30E-40 |
| EF041-2 | gi\|143603 | sporulation protein [*Bacillus subtilis*] > gnl\|PID\|e1183163 | 278 | 1.00E-34 |
| EF041-2 | gi\|40005 | OppA gene product [*Bacillus subtilis*] | 279 | 1.00E-34 |
| EF041-2 | gi\|47802 | Opp A (AA1-542) [*Salmonella typhimurium*] > gi\|47808 precursor | 141 | 6.60E-30 |
| EF041-2 | gi\|304925 | periplasmic oligopeptide binding protein [*Escherichia coli*] | 160 | 1.90E-29 |
| EF041-2 | gi\|1574679 | oligopeptide binding protein (oppA) [*Haemophilus influenzae*] | 163 | 1.00E-28 |
| EF041-2 | gi\|147014 | oligopeptide binding protein precursor [*Escherichia coli*] | 160 | 1.50E-28 |
| EF041-2 | gi\|2253286 | (AF005657) plasminogen binding protein [*Borrelia burgdorferi*] | 134 | 5.00E-27 |
| EF045-2 | gi\|308854 | oligopeptide binding protein [*Lactococcus lactis*] > pir\|E53290\|E53290 | 437 | 3.20E-125 |
| EF045-2 | gi\|495181 | oligopeptide binding protein [*Lactococcus lactis*] | 426 | 9.70E-124 |
| EF045-2 | gi\|677945 | AppA [*Bacillus subtilis*] > gnl\|PID\|e1183158 oligopeptide ABC | 154 | 2.30E-31 |
| EF045-2 | gi\|293014 | peptide-binding protein [*Lactococcus lactis*] > pir\|B47098\|B47098 | 158 | 2.40E-14 |
| EF048-2 | gi\|1574060 | hypothetical [*Haemophilus influenzae*] > pir\|I64164\|I64164 | 250 | 2.30E-41 |
| EF048-2 | dbj\|AB001488_2 | (AB001488) SIMILAR TO C4-DICARBOXYLATE-BINDING PERIPLASMIC | 208 | 3.60E-34 |
| EF048-2 | gi\|466717 | No definition line found [*Escherichia coli*] > gi\|1790004 (AE000435) | 199 | 1.30E-30 |
| EF048-2 | gi\|46006 | periplasmic C4-dicarboxylate binding-protein [*Rhodobacter capsulatus*] | 162 | 1.40E-25 |
| EF048-2 | gi\|1573102 | hypothetical [*Haemophilus influenzae*] > pir\|H64143\|H64143 | 244 | 3.80E-25 |
| EF048-2 | gi\|2182530 | (AE000085) Y4mM [*Rhizobium sp.* NGR234] | 114 | 5.60E-18 |
| EF048-2 | gi\|1572999 | hypothetical [*Haemophilus influenzae*] > pir\|E64141\|E64141 | 116 | 5.90E-15 |
| EF049-2 | gi\|149581 | maturation protein [*Lactobacillus paracasei*] > pir\|A44858\|A44858 | 241 | 2.40E-55 |
| EF049-2 | gi\|47198 | ORE (AA 1 to 299) [*Lactococcus lactis* cremoris] > pir\|S08083\|S08083 | 239 | 1.00E-54 |
| EF049-2 | gi\|432402 | maturation protein [*Lactococcus lactis*] > gi\|623055 proteinase | 239 | 6.20E-54 |
| EF049-2 | gi\|472835 | ORF1 [*Lactococcus lactis* cremoris] | 241 | 1.50E-53 |
| EF049-2 | gi\|39782 | 33kDa lipoprotein [*Bacillus subtilis*] > gnl\|PID\|e325 181.33kDa | 128 | 8.90E-40 |
| EF051-2 | gnl\|PID\|d101142 | molybdate-binding periplasmic protein [*Synechocystis sp.*] | 173 | 3.20E-50 |
| EF051-2 | gnl\|PID\|e118602 | alternate gene name: yvsD; similar to molybdate-binding | 314 | 5.90E-50 |
| EF051-2 | gi\|1574546 | lsg locus hypothetical [*Haemophilus influenzae*] > pir\|A64175\|A64175 | 161 | 2.20E-43 |
| EF051-2 | gi\|504498 | periplasmic molybdate-binding protein [*Escherichia coli*] > gi\|1147817 | 148 | 1.40E-30 |
| EF051-2 | gi\|148939 | ORE 8 [*Haemophilus influenzae*] > pir\|S27583\|S27583 hypothetical | 150 | 8.10E-28 |
| EF054-2 | gi\|150556 | surface protein [Plasmid pCF10] > pir\|A41826\|A41826 probable | 1490 | 1.80E-192 |

TABLE 2-continued

Closest matching sequences between the polypeptides of the present invention and sequences in GenBank and Derwent databases.

| | | | | |
|---|---|---|---|---|
| EF054-2 | gnl\|PID\|e236571 | cell wall anchoring signal [*Enterococcus faecalis*] | 515 | 8.10E-64 |
| EF054-2 | gi\|45738 | ORFC [*Enterococcus faecalis*] > pir\|JH0204\|JH0204 hypothetical 30.5K | 372 | 1.60E-58 |
| EF054-2 | gi\|496520 | orf iota [*Streptococcus pyogenes*] > pir\|S68125\|S45091 hypothetical | 362 | 1.30E-43 |
| EF054-2 | gi\|160693 | sporozoite surface protein [*Plasmodium yoelii*] > pir\|A45559\|A45559 | 286 | 4.30E-33 |
| EF054-2 | gi\|1813523 | PbTRAP [*Plasmodium berghei*] | 305 | 1.30E-32 |
| EF054-2 | gnl\|PID\|e225687 | zinc finger protein [*Mus musculus*] > gnl\|PID\|e225688 zinc | 246 | 3.60E-26 |
| EF054-2 | gi\|2290394 | IgG and IgE immunoreactive antigen recognized by sera from patients | 242 | 1.40E-25 |
| EF054-2 | gi\|2290392 | IgG and IgE immunoreactive antigen recognized by sera from patients | 237 | 7.80E-25 |
| EF054-2 | gi\|46523 | B antigen [*Streptococcus agalactiae*] | 232 | 2.80E-23 |
| EF054-2 | pir\|S15330\|FCSO | IgA Fc receptor precursor - *Streptococcus agalactiac* | 228 | 1.00E-22 |
| EF054-2 | gi\|1620100 | Pro- and Glu-rich, PENPEV (10x); similar to *Streptococcus B* | 210 | 3.10E-21 |
| EF054-2 | gi\|63686 | NF-M c-terminus [*Gallus gallus*] | 222 | 6.90E-21 |
| EF054-2 | gi\|63689 | NF-M protein [*Gallus gallus*] > pir\|S15762\|S15762 neurofilament triplet | 222 | 8.50E-21 |
| EF054-2 | gi\|757867 | TATA-box like sequence (Us11) [Human herpesvirus 1] > gi\|291493 18 | 194 | 4.10E-19 |
| EF059-2 | gnl\|PID\|e236571 | cell wall anchoring signal [*Enterococcus faecalis*] | 418 | 5.60E-95 |
| EF059-2 | gi\|150556 | surface protein [Plasmid pCF10] > pir\|A41826\|A41826 probable | 606 | 3.70E-87 |
| EF059-2 | gi\|45738 | ORFC [*Enterococcus faecalis*] > pir\|JH0204\|JH0204 hypothetical 30.5K | 366 | 9.30E-50 |
| EF059-2 | gi\|496520 | orf iota [*Streptococcus pyogenes*] > pir\|S68125\|S45091 hypothetical | 367 | 5.90E-44 |
| EF059-2 | gi\|160693 | sporozoite surface protein [*Plasmodium yoelii*] > pir\|A45559\|A45559 | 344 | 1.10E-38 |
| EF059-2 | gi\|1813523 | PbTRAP [*Plasmodium berghei*] | 295 | 2.50E-32 |
| EF059-2 | gi\|2290394 | IgG and IgE immunoreactive antigen recognized by sera from patients | 251 | 3.00E-29 |
| EF059-2 | gi\|2290392 | IgG and IgE immunoreactive antigen recognized by sera from patients | 251 | 3.40E-29 |
| EF059-2 | gi\|1620100 | Pro- and Glu-rich, PENPEV (10x); similar to *Streptococcus B* | 253 | 6.40E-27 |
| EF059-2 | gi\|46521 | Fc receptor [*Streptococcus agalactiae*] > pir\|A60234\|A60234 IgA Fc | 197 | 2.70E-26 |
| EF059-2 | gi\|46523 | B antigen [*Streptococcus agalactiae*] | 232 | 9.30E-26 |
| EF059-2 | pirlS\|15330\|FCSO | IgA Fc receptor precursor - *Streptococcus agalactiae* | 232 | 9.30E-26 |
| EF059-2 | gnl\|PID\|e225687 | zinc finger protein [*Mus musculus*] > gnl\|PID\|e225688 zinc | 234 | 1.40E-22 |
| EF059-2 | gi\|425356 | zona pellucida protein [*Pseudopleuronectes americanus*] | 229 | 1.00E-21 |
| EF059-2 | gi\|457769 | Collagen [*Bombyx mori*] > pir\|S42886\|S42886 collagen - silkworm | 209 | 7.60E-19 |
| EF061-2 | gnl\|PID\|e236571 | cell wall anchoring signal [*Enterococcus faecalis*] | 925 | 8.10E-118 |
| EF061-2 | gi\|150556 | surface protein [Plasmid pCF10] > pir\|A41826\|A41826 probable | 350 | 1.50E-107 |
| EF061-2 | gi\|496520 | orf iota [*Streptococcus pyogenes*] > pir\|S68125\|S45091 hypothetical | 308 | 1.40E-58 |
| EF061-2 | gi\|45738 | ORFC [*Enterococcus faecalis*] > pir\|JH0204\|JH0204 hypothetical 30.5K | 322 | 6.40E-50 |
| EF061-2 | gi\|1813523 | PbTRAP [*Plasmodium berghei*] | 263 | 1.00E-26 |
| EF061-2 | gi\|160693 | sporozoite surface protein [*Plasmodium yoelii*] > pir\|A45559\|A45559 | 241 | 9.00E-25 |
| EF061-2 | gi\|63686 | NF-M c-terminus [*Gallus gallus*] | 232 | 2.10E-22 |
| EF061-2 | gi\|63689 | NF-M protein [*Gallus gallus*] > pir\|S15762\|S15762 neurofilament triplet | 232 | 2.60E-22 |
| EF06l-2 | gi\|2290392 | IgG and IgE immunoreactive antigen recognized by sera from patients | 176 | 2.40E-21 |
| EF061-2 | gi\|1620100 | Pro- and Glu-rich, PENPEV (10x); similar to *Streptococcus B* | 165 | 2.70E-20 |
| EF061-2 | gnl\|PID\|e225687 | zinc finger protein [*Mus musculus*] > gnl\|PID\|e225688 zinc | 197 | 7.80E-19 |
| EF061-2 | gi\|160355 | interspersed repeat antigen [*Plasmodium falciparum*] | 199 | 8.20E-18 |
| EF061-2 | gi\|410750 | interspersed repeat antigen [*Plasmodium falciparum*] | 199 | 8.90E-18 |
| EF061-2 | gi\|2290388 | IgG and IgE immunoreactive antigen recognized by sera from patients | 182 | 1.40E- 17 |
| EF061-2 | gi\|2290394 | IgG and IgE immunoreactive antigen recognized by sera from patients | 180 | 2.80E-17 |
| EF062-2 | gi\|47049 | asal gene product (AA1-1296) [*Enterococcus faecalis*] | 3716 | 0 |
| EF062-2 | gi\|43324 | aggregation substance (ASP1) [*Enterococcus faecalis*] | 4003 | 0 |
| EF062-2 | gi\|2109266 | aggregation substance [*Enterococcus faecium*] | 5523 | 0 |
| EF062-2 | gi\|150555 | aggregation substance [*Plasmid pCF10*] > pir\|H41662\|H41662 150K mating | 6338 | 0 |
| EF062-2 | gi\|1100973 | SspB precursor [*Streptococcus gordonii*] | 110 | 9.90E-39 |
| EF062-2 | gi\|47248 | PAc protein precursor (AA-38 to 1527) [*Streptococcus mutans*] | 107 | 1.70E-38 |
| EF062-2 | gnl\|PID\|d101507 | surface protein antigen precursor [*Streptococcus sobrinus*] | 132 | 5.00E-36 |
| EF062-2 | gi\|47267 | cell surface antigen I/II [*Streptococcus mutans*] > pir\|S06839\|S06839 | 107 | 6.50E-36 |
| EF062-2 | bbs\|148453 | SpaA = endocarditis immunodominant antigen [*Streptococcus sobrinus*, | 132 | 1.20E-35 |
| EF062-2 | gi\|47620 | antigen I/II [*Streptococcus sobrinus*] > pir\|A60338\|A60338 surface | 132 | 2.90E-35 |
| EF062-2 | pir\|A35186\|A351 | salivary agglutinin receptor precursor - *Streptococcus* | 109 | 2.10E-34 |
| EF062-2 | gi\|1100971 | SspA [*Streptococcus gordonii*] | 110 | 3.80E-32 |
| EF062-2 | gi\|1100975 | SspA [*Streptococcus gordonii*] | 110 | 2.30E-21 |
| EF063-2 | gi\|47049 | asal gene product (AA 1-1296) [*Enterococcus faecalis*] | 3716 | 0 |
| EF063-2 | gi\|43324 | aggregation substance (ASP1) [*Enterococcus faecalis*] | 4003 | 0 |
| EF063-2 | gi\|2109266 | aggregation substance [*Enterococcus faecium*] | 5523 | 0 |
| EF063-2 | gi\|150555 | aggregation substance [*Plasmid pCF10*] > pir\|H41662\|H41662 150K mating | 6338 | 0 |
| EF063-2 | gi\|1100973 | SspB precursor [*Streptococcus gordonii*] | 110 | 9.90E-39 |
| EF063-2 | gi\|47248 | PAc protein precursor (AA-38 to 1527) [*Streptococcus mutans*] | 107 | 1.70E-38 |
| EF063-2 | gnl\|PID\|d101507 | surface protein antigen precursor [*Streptococcus sobrinus*] | 132 | 5.00E-36 |
| EF063-2 | gi\|47267 | cell surface antigen I/II [*Streptococcus mutans*] > pir\|S06839\|S06839 | 107 | 6.50E-36 |
| EF063-2 | bbs\|148453 | SpaA= endocarditis immunodominant antigen [*Streptococcus sobrinus*, | 132 | 1.20E-35 |
| EF063-2 | gi\|47620 | antigen I/II [*Streptococcus sobrinus*] > pir\|A60338\|A60338 surface | 132 | 2.90E-35 |
| EF062-2 | pir\|A35186\|A351 | salivary agglutinin receptor precursor - *Streptococcus* | 109 | 2.10E-34 |
| EF063-2 | gi\|1100971 | SspA [*Streptococcus gordonii*] | 110 | 3.80E-32 |
| EF063-2 | gi\|1100975 | SspA [*Streptococcus gordonii*] | 110 | 2.30E-21 |
| EF064-2 | gi\|47049 | asal gene product (AA 1-1296) [*Enterococcus faecalis*] | 3716 | 0 |
| EF064-2 | gi\|43324 | aggregation substance (ASP1) [*Enterococcus faecalis*] | 4003 | 0 |
| EF064-2 | gi\|2109266 | aggregation substance [*Enterococcus faecium*] | 5523 | 0 |
| EF064-2 | gi\|150555 | aggregation substance [*Plasmid pCF10*] > pir\|H41662\|H41662 150K mating | 6338 | 0 |
| EF064-2 | gi\|1100973 | SspB precursor [*Streptococcus gordonii*] | 110 | 9.90E-39 |
| EF064-2 | gi\|47248 | PAc protein precursor (AA -38 to 1527) [*Streptococcus mutans*] | 107 | 1.70E-38 |
| EF064-2 | gnl\|PID\|d101507 | surface protein antigen precursor [*Streptococcus sobrinus*] | 132 | 5.00E-36 |

TABLE 2-continued

Closest matching sequences between the polypeptides of the present invention and sequences in GenBank and Derwent databases.

| | | | | |
|---|---|---|---|---|
| EF064-2 | gi\|47267 | cell surface antigen I/II [*Streptococcus mutans*] > pir\|S06839\|S06839 | 107 | 6.50E-36 |
| EF064-2 | bbs\|148453 | SpaA= endocarditis immunodominant antigen [*Streptococcus sobrinus*, | 132 | 1.20E-35 |
| EF064-2 | gi\|47620 | antigen I/II [*Streptococcus sobrinus*] > pir\|A60338\|A60338 surface | 132 | 2.90E-35 |
| EF064-2 | pir\|A35186\|A351 | salivary agglutinin receptor precursor - *Streptococcus* | 109 | 2.10E-34 |
| EF064-2 | gi\|1100971 | SspA [*Streptococcus gordonii*] | 110 | 3.80E-32 |
| EF064-2 | gi\|1100975 | SspA [*Streptococcus gordonii*] | 110 | 2.30E-21 |
| EF068-2 | gi\|790398 | T06D8.1 [*Caenorhabditis elegans*] | 137 | 8.50E-17 |
| EF068-2 | gnl\|PID\|d102084 | membrane glycoprotein [*Equine herpesvirus 1*] | 210 | 5.80E-16 |
| EF068-2 | gi\|2286204 | (AF011339) unknown [*Acinetobacter calcoaceticus*] | 121 | 8.40E-16 |
| EF068-2 | gi\|330862 | membrane glycoprotein [*Equine herpesvirus 1*] > pir\|H36802\|VGBEX1 | 208 | 1.10E-15 |
| EF068-2 | gi\|1707247 | partial CDS [*Caenorhabditis elegans*] | 131 | 3.70E-15 |
| EF068-2 | gnl\|PID\|d102084 | membrane glycoprotein [*Equine herpesvirus 1*] | 203 | 6.20E-15 |
| EF068-2 | gi\|213392 | antifreeze glycoprotein [*Notothenia coriiceps*] > pir\|A38420\|A38420 | 102 | 4.60E-13 |
| EF068-2 | gnl\|PID\|e125464 | (AL022022) PGRS-family protein [*Mycobacterium tuberculosis*] | 145 | 1.50E-12 |
| EF068-2 | gi\|951460 | FIM-C.1 gene product [*Xenopus laevis*] > pir\|A45155\|A45155 mucin | 109 | 2.70E-12 |
| EF069-2 | gi\|790398 | T06D8.1 [*Caenorhabditis elegans*] | 137 | 8.50E-17 |
| EF069-2 | gnl\|PID\|d102084 | membrane glycoprotein [*Equine herpesvirus 1*] | 210 | 5.80E-16 |
| EF069-2 | gi\|2286204 | (AF011339) unknown [*Acinetobacter calcoaceticus*] | 121 | 8.40E-16 |
| EF069-2 | gi\|330862 | membrane glycoprotein [*Equine herpesvirus 1*] > pir\|H36802\|VGBEX1 | 208 | 1.10E-15 |
| EF069-2 | gi\|1707247 | partial CDS [*Caenorhabditis elegans*] | 131 | 3.70E-15 |
| EF069-2 | gnl\|PID\|d102084 | membrane glycoprotein [*Equine herpesvirus 1*] | 203 | 6.20E-15 |
| EF069-2 | gi\|213392 | antifreeze glycoprotein [*Notothenia coriiceps*] > pir\|A38420\|A38420 | 102 | 4.60E-13 |
| EF069-2 | gnl\|PID\|e125464 | (AL022022) PGRS-family protein [*Mycobacterium tuberculosis*] | 145 | 1.50E-12 |
| EF069-2 | gi\|951460 | FIM-C.1 gene product [*Xenopus laevis*] > pir\|A45155\|A45155 mucin | 109 | 2.70E-12 |
| EF070-2 | gi\|790398 | T06D8.1 [*Caenorhabditis elegans*] | 137 | 8.50E-17 |
| EF070-2 | gnl\|PID\|d102084 | membrane glycoprotein [*Equine herpesvirus 1*] | 210 | 5.80E-16 |
| EF070-2 | gi\|2286204 | (AF011339) unknown [*Acinetobacter calcoaceticus*] | 121 | 8.40E-16 |
| EF070-2 | gi\|330862 | membrane glycoprotein [*Equine herpesvirus 1*] > pir\|H36802\|VGBEX1 | 208 | 1.10E-15 |
| EF070-2 | gi\|1707247 | partial CDS [*Caenorhabditis elegans*] | 131 | 3.70E-15 |
| EF070-2 | gnl\|PID\|d102084 | membrane glycoprotein [*Equine herpesvirus 1*] | 203 | 6.20E-15 |
| EF070-2 | gi\|213392 | antifreeze glycoprotein [*Notothenia coriiceps*] > pir\|A38420\|A38420 | 102 | 4.60E-13 |
| EF070-2 | gnl\|PID\|e125464 | (AL022022) PGRS-family protein [*Mycobacterium tuberculosis*] | 145 | 1.50E-12 |
| EF070-2 | gi\|951460 | FIM-C.1 gene product [*Xenopus laevis*] > pir\|A45155\|A45155 mucin | 109 | 2.70E-12 |
| EF071-2 | gnl\|PID\|e306428 | unnamed protein product [Bacteriophage rlt] > gi\|1353566 Lysin | 127 | 2.00E-37 |
| EF071-2 | gi\|853751 | N-acetylmuramoyl-L-alanine amidase [Bacteriophage A511] | 273 | 2.60E-36 |
| EF073-2 | gi\|143830 | xpaC [*Bacillus subtilis*] > gnl\|PID\|d1005803 hydrolysis of | 173 | 7.10E-16 |
| EF074-2 | gi\|1256698 | chitinase [*Serratia marcescens*] > gi\|1256698 chitinase [*Serratia* | 618 | 2.60E-104 |
| EF074-2 | gi\|763985 | chitinase A [*Vibrio harveyi*] | 526 | 2.80E-84 |
| EF075-2 | gi\|143156 | membrane bound protein [*Bacillus subtilis*] > gnl\|PID\|e1184471 | 593 | 1.70E-91 |
| EF075-2 | pir\|D70070\|D700 | transcriptional regulator homolog ywtF - *Bacillus subtilis* | 118 | 1.90E-59 |
| EF075-2 | gi\|762327 | putative transcriptional regulator [*Bacillus subtilis*] | 148 | 9.60E-53 |
| EF075-2 | gi\|1276874 | EpsA [*Streptococcus thermophilus*] | 239 | 2.20E-33 |
| EF075-2 | gnl\|PID\|e289126 | unknown [*Streptococcus pneumoniae*] | 150 | 1.20E-27 |
| EF075-2 | gi\|485275 | putative regulatory protein [*Streptococcus pneumoniae*] | 150 | 2.50E-27 |
| EF075-2 | gi\|2804735 | (AF030367) putative regulatory protein [*Streptococcus pneumoniae*] | 150 | 2.50E-27 |
| EF075-2 | gi\|2804747 | (AF030369) putative regulatory protein [*Streptococcus pneumoniae*] | 150 | 2.50E-27 |
| EF075-2 | gnl\|PID\|e116988 | capsular polysaccharide synthesis protein [*Streptococcus* | 148 | 5.30E-27 |
| EF075-2 | gi\|2804769 | (AF030373) putative regulatory protein [*Streptococcus pneumoniae*] | 148 | 5.30E-27 |
| EF075-2 | gi\|1147744 | PSR [*Enterococcus hirae*] | 109 | 2.10E-23 |
| EF075-2 | gi\|790435 | PSR [*Enterococcus faecium*] > pir\|S54177\|S54177 PSR protein | 102 | 4.40E-19 |
| EF075-2 | gi\|12267239 | ORF1 [*Staphylococcus epidermidis*] | 109 | 8.50E-19 |
| EF075-2 | gnl\|PID\|d101895 | membrane bound protein LytR [*Synechocystis sp.*] | 121 | 8.50E-16 |
| EF077-2 | gnl\|PID\|d101135 | cadmium-transporting ATPase [*Synechocystis sp.*] | 396 | 2.30E-113 |
| EF077-2 | gi\|150719 | cadmium resistance protein [Plasmid pI258] > pir\|A3256\|A32561 | 373 | 8.60E-112 |
| EF077-2 | gi\|143753 | cadmium-efflux ATPase [*Bacillus firmus*] > pir\|D42707\|D42707 probable | 361 | 8.10E-111 |
| EF077-2 | gi\|152978 | E1-E2 cadmium efflux adenosine triphosphatase [*Staphylococcus* | 381 | 4.30E-110 |
| EF077-2 | gnl\|PID\|e248808 | unknown [*Mycobacterium tuberculosis*] | 298 | 3.50E-107 |
| EF077-2 | gi\|495646 | ATPase [Transposon Tn5422] | 361 | 2.10E-106 |
| EF077-2 | gnl\|PID\|e118497 | similar to heavy metal-transporting ATPase [*Bacillus* | 286 | 3.50E-104 |
| EF077-2 | gi\|1699049 | cadmium resistance protein [*Lactococcus lactis*] | 352 | 3.60E-100 |
| EF077-2 | gnl\|PID\|e118603 | similar to heavy metal-transporting ATPase [*Bacillus* | 254 | 9.90E-100 |
| EF077-2 | gnl\|PID\|e306540 | unknown [*Mycobacterium tuberculosis*] | 352 | 5.20E-88 |
| EF077-2 | gnl\|PID\|e263525 | P-type ATPase [*Mycobacterium tuberculosis*] > gnl\|PID\|e249413 | 199 | 5.50E-86 |
| EF077-2 | gnl\|PID\|e264090 | unknown [*Mycobacterium tuberculosis*] | 250 | 3.00E-84 |
| EF077-2 | gnl\|PID\|d101135 | cadmium-transporting ATPase [*Synechocystis sp.*] | 260 | 1.00E-81 |
| EF077-2 | gi\|1773166 | probable copper-transporting atpase [*Escherichia coli*] > gi\|1786691 | 212 | 4.70E-80 |
| EF077-2 | gi\|1354935 | probable copper-transporting atpase [*Escherichia coli*] | 212 | 8.50E-79 |
| EF078-2 | gi\|143331 | alkaline phosphatase regulatory protein [*Bacillus subtilis*] | 257 | 5.50E-58 |
| EF078-2 | gi\|410142 | ORFX18 [*Bacillus subtilis*] > gnl\|PID\|e1185580 two-component sensor | 235 | 8.20E-51 |
| EF078-2 | gnl\|PID\|d101196 | homologous to sp:PHOR_BACSU [*Bacillus subtilis*] | 219 | 4.20E-44 |
| EF078-2 | gi\|1575578 | histidine protein kinase [*Thermotoga maritima*] | 191 | 7.10E-44 |
| EF078-2 | gi\|2182990 | histidine kinase [*Lactococcus lactis cremoris*] | 169 | 6.40E-40 |
| EF078-2 | gi\|2182992 | histidine kinase [*Lactococcus lactis cremoris*] | 152 | 1.10E-39 |
| EF078-2 | gnl\|PID\|d101134 | sensory transduction histidine kinase [*Synechocystis sp.*] | 259 | 3.90E-38 |
| EF078-2 | gi\|149296 | phosphate regulatory protein phoR (gtg start codon) [*Klebsiella* | 228 | 7.60E-33 |
| EF078-2 | gi\|581188 | phoR gene product (AA 1–431) [*Escherichia coli*] > gi\|1657596 | 226 | 1.60E-32 |
| EF078-2 | gnl\|PID\|d101087 | sensory transduction histidine kinase [*Synechocystis sp.*] | 138 | 3.70E-32 |

TABLE 2-continued

Closest matching sequences between the polypeptides of the present invention and sequences in GenBank and Derwent databases.

| | | | | |
|---|---|---|---|---|
| EF078-2 | gnl\|PID\|e266592 | unknown [*Mycobacterium tuberculosis*] | 232 | 1.10E-31 |
| EF078-2 | gi\|2 182996 | histidine kinase [*Lactococcus lactis cremoris*] | 206 | 1.30E-31 |
| EF078-2 | gnl\|PID\|d101135 | sensory transduction histidine kinase [*Synechocystis sp.*] | 256 | 1.30E-31 |
| EF078-2 | gi\|294893 | phosphate regulatory protein phoR (gtg start codon) [*Shigella* | 225 | 1.60E-31 |
| EF078-2 | gi\|288420 | drug sensory protein A [Synechocystis PCC6803] > gnl\|PID\|d1017420 | 106 | 2.50E-31 |
| EF079-2 | gi\|2098719 | putative fimbrial-associated protein [*Actinomyces naeslundii*] | 183 | 8.60E-26 |
| EF081-2 | gi\|467806 | penicillin-binding protein [*Enterococcus faecalis*] | 1356 | 2.10E-178 |
| EF081-2 | gi\|790429 | low affinity penicillin-binding protein 5 (PBP5) [*Enterococcus* | 607 | 1.00E-78 |
| EF081-2 | gnl\|PID\|e208365 | penicillin-binding protein 5 [*Enterococcus faecium*] | 604 | 1.10E-78 |
| EF081-2 | gi\|790433 | low affinity penicillin-binding protein 5 (PBP5) [*Enterococcus* | 604 | 2.70E-78 |
| EF081-2 | gi\|790437 | low affinity penicillin-binding protein 5 (PBP5) [*Enterococcus* | 602 | 5.10E-78 |
| EF081-2 | gi\|790431 | low affinity penicillin-binding protein 5 (PBP5) [*Enterococcus* | 591 | 2.60E-77 |
| EF081-2 | gi\|43342 | D-alanyl-D-alanine carboxypeptidase [*Enterococcus hirae*] | 587 | 9.30E-77 |
| EF081-2 | gi\|49000 | D-alanyl-D-alanine carboxypeptidase [*Enterococcus hirae*] | 572 | 5.20E-74 |
| EF081-2 | gnl\|PID\|d100794 | penicillin-binding protein 2 [*Bacillus subtilis*] | 149 | 7.40E-24 |
| EF081-2 | gnl\|PID\|e315088 | MecAl [*Staphylococcus sciuri*] | 111 | 4.40E-19 |
| EF081-2 | gnl\|PID\|e286651 | MecA protein [*Staphylococcus sciuri*] | 106 | 2.90E-18 |
| EF081-2 | gnl\|PID\|e316581 | MecA protein [*Staphylococcus sciuri*] | 111 | 2.90E-18 |
| EF081-2 | gnl\|PID\|e316607 | MecA2 protein [*Staphylococcus sciuri*] | 101 | 3.70E-14 |
| EF081-2 | gnl\|PID\|e316613 | MecA protein [*Staphylococcus sciuri*] > gi\|46613 mecA gene | 101 | 3.70E-14 |
| EF083-2 | gi\|496283 | lysin [Bacteriophage Tuc2009] | 436 | 6.20E-176 |
| EF083-2 | gi\|530798 | LysB [Bacteriophage phi-LC3] | 421 | 3.00E-175 |
| EF083-2 | gi\|66183 | muramidase [Bacteriophage CP-7] | 186 | 1.20E-21 |
| EF083-2 | gi\|166188 | muramidase [Bacteriophage CP-9] > pir\|JQ0438\|MUBPC9 | 188 | 5.00E-21 |
| EF083-2 | gi\|623084 | muramidase; muramidase [Bacteriophage LL-H] | 193 | 8.40E-20 |
| EF083-2 | gi\|166175 | muramidase [Bacteriophage CP-1] | 175 | 3.40E-19 |
| EF083-2 | gnl\|PID\|e221272 | lysozyme [Bacteriophage CP-1] > pir\|A31086\|MUBPCP | 175 | 3.40E-19 |
| EF083-2 | pir\|JQ0437\|MUBP | N-acetylmuramoyl-L-alanine amidase (EC 3.5.1.28) - phage | 171 | 9.50E-19 |
| EF083-2 | gi\|410502 | LysA [Bacteriophage mv4] > pir\|S38477\|S38477 lytic enzyme lysA | 187 | 8.90E-17 |
| EF083-2 | gi\|793850 | lysin [Lactobacillus bacteriophage phi adh] > gnl\|PID\|e1217314 lysin | 117 | 5.60E-15 |
| EF084-2 | gi\|2293312 | (AF008220) YttP [*Bacillus subtilis*] > gnl\|PID\|e1185879 similar to | 438 | 1.70E-140 |
| EF084-2 | gi\|2367234 | (AE000425) hypothetical 43.8 kD protein in rhsB-pit intergenic | 167 | 2.20E-51 |
| EF084-2 | gi\|912464 | No definition line found [*Escherichia coli*] | 167 | 6.00E-51 |
| EF084-2 | gnl\|PID\|d101127 | hypothetical protein [*Synechocystis sp.*] > pir\|S76678\|S76678 | 151 | 6.10E-42 |
| EF084-2 | gi\|1573954 | hypothetical [*Haemophilus influenzae*] > pir\|G64161\|G64161 | 142 | 2.90E-40 |
| EF085-2 | gi\|1209527 | protein histidine kinase [*Enterococcus faecalis*] | 2023 | 8.00E-279 |
| EF085-2 | gi\|467057 | phoR; B2168_C3_247 [*Mycobacterium leprae*] > pir\|S72905\|S72905 | 226 | 8.80E-23 |
| EF085-2 | gnl\|PID\|e119229 | SenX3 [*Mycobacterium bovis* BCG] | 222 | 3.10E-22 |
| EF085-2 | gnl\|PID\|e255152 | unknown [*Mycobacterium tuberculosis*] > gnl\|PID\|e321546 SenX3 | 222 | 3.10E-22 |
| EF085-2 | gi\|1778485 | PcoS homolog [*Escherichia coli*] > gi\|1786783 (AE000162) f480; This | 111 | 3.80E-16 |
| EF085-2 | gi\|149296 | phosphate regulatory protein phoR (gtg start codon) [*Klebsiella* | 110 | 1.40E-14 |
| EF085-2 | gi\|581188 | phoR gene product (AA 1–431) [*Escherichia coli*] > gi\|1657596 | 103 | 5.30E-14 |
| EF085-2 | gi\|143331 | alkaline phosphatase regulatory protein [*Bacillus subtilis*] | 118 | 4.90E-13 |
| EF085-2 | gi\|537239 | alternate gene name phoM; CG Site No. 395 [*Escherichia coli*] | 126 | 9.50E-13 |
| EF085-2 | gi\|147251 | phoM [*Escherichia coli*] > gi\|809670 phoM protein (1 is 3rd base in | 126 | 9.50E-13 |
| EF085-2 | gi\|2182992 | histidine kinase [*Lactococcus lactis cremoris*] | 109 | 5.90E-12 |
| EF086-2 | gi\|437706 | alternative truncated translation product from E. coli [*Streptococcus* | 221 | 3.00E-54 |
| EF086-2 | gi\|437705 | hyaluronidase [*Streptococcus pneumoniae*] | 221 | 1.60E-53 |
| EF086-2 | gi\|595847 | hyaluronate lyase [*Streptococcus agalactiae*] > pir\|A55137\|A55137 | 203 | 3.30E-44 |
| EF086-2 | gi\|705406 | hyaluronate lyase [*Staphylococcus aureus*] | 191 | 3.40E-42 |
| EF086-2 | gi\|562086 | hyaluronidase [*Propionibacterium acnes*] | 198 | 6.00E-27 |
| EF087-2 | gi\|437706 | alternative truncated translation product from E. coli [*Streptococcus* | 221 | 3.00E-54 |
| EF087-2 | gi\|437705 | hyaluronidase [*Streptococcus pneumoniae*] | 221 | 1.60E-53 |
| EF087-2 | gi\|595847 | hyaluronate lyase [*Streptococcus agalactiae*] > pir\|A55137\|A55137 | 203 | 3.30E-44 |
| EF087-2 | gi\|705406 | hyaluronate lyase [*Staphylococcus aureus*] | 191 | 3.40E-42 |
| EF087-2 | gi\|562086 | hyaluronidase [*Propionibacterium acnes*] | 198 | 6.00E-27 |
| EF088-2 | gi\|437706 | alternative truncated translation product from E. coli [*Streptococcus* | 221 | 3.00E-54 |
| EF088-2 | gi\|437705 | hyaluronidase [*Streptococcus pneumoniae*] | 221 | 1.60E-53 |
| EF088-2 | gi\|595847 | hyaluronate lyase [*Streptococcus agalactiae*] > pir\|A55137\|A55137 | 203 | 3.30E-44 |
| EF088-2 | gi\|705406 | hyaluronate lyase [*Staphylococcus aureus*] | 191 | 3.40E-42 |
| EF088-2 | gi\|562086 | hyaluronidase [*Propionibacterium acnes*] | 198 | 6.00E-27 |
| EF091-2 | gi\|556016 | similar to plant water stress proteins; ORF2 [*Bacillus subtilis*] | 198 | 5.50E-21 |
| EF091-2 | gi\|2353333 | (AF016513) Ce-LEA [*Caenorhabditis elegans*] | 189 | 2.40E-17 |
| EF091-2 | gnl\|PID\|e353216 | seed maturation protein homolog [*Arabidopsis thaliana*] | 146 | 3.60E-11 |
| EF091-2 | gi\|1161171 | late embryogenesis abundant protein [*Picea glauca*] | 132 | 5.70E-11 |
| EF091-2 | pir\|S04909\|S049 | embryonic protein DC8 (clone 8/10) - carrot | 127 | 6.50E-11 |
| EF092-2 | gi\|2689898 | (AE000792) PTS system, cellobiose-specific IIB component (celA) | 145 | 4.00E-27 |
| EF092-2 | gnl\|PID\|d102048 | B. subtilis, cellobiose phosphotransferase system, celA; | 116 | 1.40E-26 |
| EF096-2 | gi\|147329 | transport protein [*Escherichia coli*] > gnl\|PID\|d1015409 | 532 | 2.10E-91 |
| EF096-2 | gi\|1573475 | spermidine/putrescine-binding periplasmic protein precursor (potD) | 527 | 1.10E-79 |
| EF096-2 | gi\|1574803 | spermidine/putrescine-binding periplasmic protein precursor (potD) | 468 | 1.60E-75 |
| EF096-2 | gi\|142681 | Lpp38 [*Pasteurella haemolytica*] | 446 | 4.40E-72 |
| EF096-2 | gnl\|PID\|d101526 | Putrescine transport protein PotF [*Escherichia coli*] | 216 | 1.50E-54 |
| EF096-2 | gi\|147334 | periplasmic putrescine binding protein [*Escherichia coli*] | 216 | 2.10E-53 |
| EF096-2 | gi\|2688565 | (AE001165) spermidine/putrescine ABC transporter, | 240 | 2.00E-48 |
| EF096-2 | gi\|1881733 | PotD [*Salmonella typhimurium*] | 253 | 2.70E-28 |
| EF096-2 | gnl\|PID\|d101926 | spermidine/putrescine-binding periplasmic protein | 243 | 4.20E-26 |

TABLE 2-continued

Closest matching sequences between the polypeptides of the present invention and sequences in GenBank and Derwent databases.

| | | | | |
|---|---|---|---|---|
| EF096-2 | gnl\|PID\|e152543 | potF gene product [*Clostridium perfringens*] | 204 | 3.30E-21 |
| EF097-2 | gi\|622991 | mannitol transport protein [*Bacillus stearothermophilus*] | 547 | 4.90E-93 |
| EF097-2 | gi\|42034 | mannitol permease [*Escherichia coli*] > gi\|466737 mannitol-specific | 535 | 5.50E-85 |
| EF097-2 | gi\|633650 | enzyme II(mannitol) [*Staphylococcus camosus*] > pir\|S68193\|S22385 | 516 | 2.10E-82 |
| EF097-2 | gi\|882462 | protein-N(pi)-phosphohistidine-sugar phosphotransferase [*Escherichia* | 509 | 3.00E-76 |
| EF097-2 | gi\|312763 | protein-N(pi)-phosphohistidine-sugar phosphotransferase [*Escherichia* | 357 | 7.50E-70 |
| EF097-2 | gnl\|PID\|d100966 | homologue of mannitol transport protein of B. | 492 | 3.10E-62 |
| EF097-2 | gnl\|PID\|d100792 | mannitol-specific phophotransferase enzyme II [*Bacillus* | 484 | 5.20E-61 |
| EF097-2 | gi\|1673855 | (AE000020) Mycoplasma pneumoniae, PTS system mannitol-specific | 232 | 3.50E-59 |
| EF097-2 | gnl\|PID\|d100651 | phosphotransferase enzymeII, mannitol-specific [*Mycoplasma* | 158 | 8.20E-18 |
| EF097-2 | pir\|S77757\|S777 | phosphotransferase system enzyme II (EC 2.7.1.69), | 103 | 2.00E-13 |
| EF100-2 | gi\|2058546 | ComYC [*Streptococcus gordonii*] | 193 | 7.30E-27 |
| EF100-2 | gi\|2058546 | ComYC [*Streptococcus gordonii*] | 193 | 7.30E-27 |
| EF100-2 | gi\|142708 | comG3 gene product [*Bacillus subtilis*] > gnl\|PPI\|e1185739 comGC | 150 | 2.90E-22 |
| EF100-2 | gi\|142708 | comG3 gene product [*Bacillus subtilis*] > gnl\|PID\|e1185739 comGC | 150 | 2.90E-22 |
| EF100-2 | gi\|148437 | secretory component [*Erwinia chrysanthemi*] > pir\|E47021\|E47021 pectic | 134 | 4.40E-15 |
| EF100-2 | gi\|148437 | secretory component [*Erwinia chrysanthemi*] > pir\|E47021\|E47021 pectic | 134 | 4.40E-15 |
| EF100-2 | gi\|606262 | ORE__o145 [*Escherichia coli*] > gi\|693706 HopG [*Escherichia coli*] | 136 | 9.10E-13 |
| EF100-2 | gi\|606262 | ORE__o145 [*Escherichia coli*] > gi\|693706 HopG [*Eseherichia coli*] | 136 | 9.10E-13 |
| EF100-2 | gi\|38828 | ExeG gene product [*Aeromonas hydrophila*] > pir\|S22910\|I49905 protein | 132 | 3.50E-12 |
| EF100-2 | gi\|38828 | ExeG gene product [*Aeromonas hydrophila*] > pir\|S22910\|I49905 protein | 132 | 3.50E-12 |
| EF100-2 | gnl\|PID\|e117259 | etpG [*Escherichia coli*] | 131 | 5.10E-12 |
| EF100-2 | gnl\|PID\|e117259 | etpG [*Escherichia coli*] | 131 | 5.10E-12 |
| EF100-2 | gi\|42189 | outG gene product [*Erwinia carotovora*] > pir\|S32861\|S32861 outG | 130 | 9.90E-12 |
| EF100-2 | gi\|42189 | outG gene product [*Erwinia carotovora*] > pir\|S32861\|S32861 outG | 130 | 9.90E-12 |
| EF100-2 | gi\|609628 | putative [*Vibrio cholerae*] | 128 | 1.60E-11 |
| EF100-2 | gi\|609628 | putative [*Vibrio cholerae*] | 128 | 1.60E-11 |
| EF101-2 | gnl\|PID\|d102573 | bacG [*Enterococcus faecalis*] | 106 | 3.60E-17 |
| EF101-2 | gnl\|PID\|e321943 | hypothetical protein [*Enterococcus faecalis*] > gnl\|PID\|e321943 | 105 | 1.80E-16 |
| EF101-2 | gnl\|PID\|e118502 | similar to hypothetical proteins from B.subtilis [*Bacillus* | 113 | 1.80E-15 |
| EF110-2 | gi\|43338 | Staphylococcal serine proteinase homologue [*Enterococcus faecalis*] | 1462 | 2.30E-195 |
| EF110-2 | gnl\|PID\|d100108 | glutamic acid specific protease prepropeptide [*Staphylococcus* | 106 | 3.70E-14 |
| EF110-2 | gi\|46687 | preproenzyme (AA -68 to 268) [*Staphylococcus aureus*] | 106 | 6.70E-14 |
| EF111-2 | gi\|606018 | ORF__0783 [*Escherichia coli*] > gi\|1789462 (AE000390) hypothetical 88.3 | 477 | 8.10E-80 |
| EF121-2 | gi\|2626826 | YfkN [*Bacillus subtilis*] > gnl\|PTD\|e1182774 similar to | 143 | 1.30E-96 |
| EF121-2 | gi\|2313187 | (AE000532) 2',3'-cyclic-nucleotide 2'-phosphodiesterase (cpdB) | 413 | 2.60E-82 |
| EF121-2 | gi\|48453 | 5'-nucleotidase [*Vibrio parahaemolyticus*] > gnl\|PID\|d1001218 | 279 | 8.50E-47 |
| EF121-2 | gi\|757842 | UDP-sugar hydrolase [*Escherichia coli*] | 239 | 1.60E-44 |
| EF121-2 | gi\|1773162 | UDP-sugar hydrolase precursor [*Escherichia coli*] > gi\|1786687 | 239 | 1.60E-44 |
| EF121-2 | gi\|47950 | precursor polypeptide (AA -25 to 525) [*Salmonella typhimurium*] | 229 | 2.10E-41 |
| EF121-2 | gi\|747913 | 2',3 '-cyclic-nucleotide 2'-phosphodiesterase [*Yersinia* | 115 | 4.70E-36 |
| EF121-2 | gi\|62772 | 5'-nucleotidase [*Discopyge ommata*] > pir\|S19564\|S19564 5'-nucleotidase | 137 | 5.80E-35 |
| EF121-2 | gi\|1573573 | 2',3'-cyclic-nucleotide 2'-phosphodiesterase (cpdB) [*Haemophilus* | 114 | 8.90E-34 |
| EF121-2 | gi\|537054 | 2=,3'-cyclic-nucleotide 2'-phosphodiesterase [*Escherichia coli*] | 110 | 1.10E-31 |
| EF121-2 | bbs\|135915 | 5'-nucleotidase= glycosylphosphatidylinositol-anchored protein {EC | 128 | 7.70E-29 |
| EF121-2 | gi\|1737443 | 5'-nucleotidase [*Boophilus microplus*] | 104 | 1.60E-28 |
| EF121-2 | gi\|202551 | 5'-nucleotidase precursor (EC 3.1.3.5) [*Rattus norvegicus*] | 138 | 6.10E-28 |
| EF121-2 | gi\|349783 | ecto-5'-nucleotidase [*Mus musculus*] > pir\|JC2001\|JC2001 | 136 | 1.10E-27 |
| EF121-2 | gi\|23897 | 5'-nucleotidase [*Homo sapiens*] > pir\|S11032\|S11032 5'-nucleotidase (EC | 133 | 1.60E-27 |
| EF122-2 | gi\|2626826 | YfkN [*Bacillus subtilis*] > gnl\|PID\|e1182774 similar to | 143 | 1.30E-96 |
| EF122-2 | gi\|2313187 | (AE000532) 2',3'-cyclic-nucleotide 2'-phosphodiesterase (cpdB) | 413 | 2.60E-82 |
| EF122-2 | gi\|48453 | 5'-nucleotidase [*Vibrio parahaemolyticus*] > gnl\|PID\|d1001218 | 279 | 8.50E-47 |
| EF122-2 | gi\|757842 | UDP-sugar hydrolase [*Escherichia coli*] | 239 | 1.60E-44 |
| EF122-2 | gi\|1773162 | UDP-sugar hydrolase precursor [*Escherichia coli*] > gi\|1786687 | 239 | 1.60E-44 |
| EF122-2 | gi\|47950 | precursor polypeptide (AA -25 to 525) [*Salmonella typhimurium*] | 229 | 2.10E-41 |
| EF122-2 | gi\|747913 | 2',3'-cyclic-nucleotide 2'-phosphodiesterase [*Yersinia* | 115 | 4.70E-36 |
| EF122-2 | gi\|62772 | 5'-nucleotidase [*Discopyge ommata*] > pir\|S19564\|S19564 5'-nucleotidase | 137 | 5.80E-35 |
| EF122-2 | gi\|1573573 | 2',3'-cyclic-nucleotide 2'-phosphodiesterase (cpdB) [*Haemophilus* | 114 | 8.90E-34 |
| EF122-2 | gi\|537054 | 2',3'-cyclic-nucleotide 2'-phosphodiesterase [*Escherichia coli*] | 110 | 1.10E-31 |
| EF122-2 | bbs\|135915 | 5'-nucleotidase=glycosylphosphatidylinositol-anchored protein {EC | 128 | 7.70E-29 |
| EF122-2 | gi\|1737443 | 5'-nucleotidase [*Boophilus microplus*] | 104 | 1.60E-28 |
| EF122-2 | gi\|202551 | 5'-nucleotidase precursor (EC 3.1.3.5) [*Rattus norvegicus*] | 138 | 6.10E-28 |
| EF122-2 | gi\|349783 | ecto-5'-nucleotidase [*Mus musculus*] > pir\|JC2001\|JC2001 | 136 | 1.10E-27 |
| EF122-2 | gi\|23897 | 5'-nucleotidase [*Homo sapiens*] > pir\|S11032\|S11032 5'-nucleotidase (EC | 133 | 1.60E-27 |
| EF129-2 | gi\|43334 | P54 protein [*Enterococcus faecium*] > pir\|S05542\|S05542 hypothetical | 630 | 9.40E-79 |
| EF129-2 | gi\|512521 | usp 45 gene product [*Lactococcus lactis*] > pir\|JN0097\|JN0097 secreted | 374 | 1.30E-42 |
| EF129-2 | gi\|149525 | secreted protein [*Lactococcus lactis*] | 371 | 3.60E-42 |
| EF129-2 | gnl\|PID\|e313022 | hypothetical protein [*Bacillus subtilis*] > gnl\|PID\|e1186168 | 317 | 2.30E-33 |
| EF130-2 | gi\|488339 | alpha-amylase [unidentified cloning vector] | 621 | 6.70E-81 |
| EF130-2 | gi\|488336 | ORF [unidentified cloning vector] | 242 | 8.00E-27 |
| EF130-2 | bbs\|112518 | alpha-amylase {N-terminal region} [Artificial sequence, Peptide | 237 | 4.80E-26 |
| EF130-2 | gnl\|PID\|e289144 | ywpE [*Bacillus subtilis*] > gnl\|PID\|e1184540 ywpE [*Bacillus* | 129 | 5.401E-11 |
| EF131-2 | gnl\|PID\|e118528 | penicillin-binding protein [*Bacillus subtilis*] | 277 | 7.40E-43 |
| EF131-2 | gi\|488330 | alpha-amylase [unidentified cloning vector] | 280 | 1.30E-31 |
| EF131-2 | gi\|509249 | No definition line found [*Lactobacillus plantarum*] | 274 | 1.10E-30 |
| EF131-2 | gnl\|PID\|d102491 | (AB009635) Fmt [*Staphylococcus aureus*] | 170 | 5.60E-20 |
| EF131-2 | gi\|515050 | DD-peptidase precursor [*Streptomyces lividans*] > pir\|S48220\|S48220 | 131 | 2.30E-14 |

TABLE 2-continued

Closest matching sequences between the polypeptides of the present invention and sequences in GenBank and Derwent databases.

| Query | | | BLAST Score | BLAST P-Value |
|---|---|---|---|---|
| EF131-2 | gi|153448 | serine DD-peptidase [*Streptomyces lividans*] | 131 | 1.20E-12 |
| EF132-2 | gi|153826 | adhesin B [*Streptococcus sanguis*] > pir|A43583|A43583 adhesin B | 1257 | 2.30E-166 |
| EF132-2 | gi|1184932 | ScbA [*Streptococcus crista*] | 1248 | 3.70E-165 |
| EF132-2 | gi|310633 | adhesin [*Streptococcus gordonii*] | 1247 | 5.10E-165 |
| EF132-2 | gi|393269 | adhesion protein [*Streptococcus pneumoniae*] | 1204 | 3.40E-163 |
| EF132-2 | gi|1575030 | surface adhesin A precursor [*Streptococcus pneumoniae*] | 1220 | 2.40E-161 |
| EF132-2 | gi|153834 | adhesin specific for salivary pellicle of dental surfaces | 1203 | 4.80E-159 |
| EF132-2 | gi|117994 | surface antigen A variant precursor [*Streptococcus pneumoniae*] | 1191 | 2.00E-157 |
| EF132-2 | gi|493017 | endocarditis specific antigen [*Enterococcus faecalis*] | 931 | 3.70E-122 |
| EF132-2 | gnl|PID|e255529 | lipoprotein [*Staphylococcus epidermidis*] | 453 | 3.20E-92 |
| EF132-2 | gi|1245464 | YfeA [*Yersinia pestis*] > gi|1245464 YfeA [*Yersinia pestis*] | 364 | 3.60E-64 |
| EF132-2 | gi|1573330 | adhesin B precursor (fimA) [*Haemophilus influenzae*] | 349 | 3.50E-63 |
| EF132-2 | gi|755075 | periplasmic-binding protein [*Synechocystis sp.*] > gnl|PID|d1018652 Mn | 326 | 6.80E-62 |
| EF132-2 | gn|PID|e118595 | similar to ABC transporter (membrane protein) [*Bacillus*] | 174 | 3.10E-32 |
| EF132-2 | gi|1777933 | TroA [*Treponema pallidum*] | 171 | 3.40E-32 |
| EF132-2 | gi|790546 | Tromp1 [*Treponema pallidum*] | 171 | 5.10E-32 |

| Query | Derwent Access. No. | Derwent Gene Description | BLAST Score | BLAST P-Value |
|---|---|---|---|---|
| EF003-2 | W20909 | *H. pylori* outer membrane protein 14ge10705orf5. | 268 | 4.20E-39 |
| EF003-2 | W20166 | *Helicobacter pylori* outer membrane protein, 16225006.aa. | 241 | 3.00E-27 |
| EF006-2 | W20909 | *H. pylori* outer membrane protein 14ge10705orf5. | 283 | 1.20E-48 |
| EF006-2 | W20166 | *Helicobacter pylori* outer membrane protein, 16225006.aa. | 266 | 1.10E-30 |
| EF008-2 | R37495 | Pneumococcal fimbrial protein A. | 967 | 1.20E-127 |
| EF008-2 | W26367 | *Staphylococcus aureus* saliva binding protein. | 467 | 7.50E-100 |
| EF008-2 | R79957 | ROM precursor TROMP 1. | 181 | 8.00E-36 |
| EF008-2 | W22134 | Treponema pallidum rare outer membrane protein (TROMP-1). | 181 | 8.00E-36 |
| EF009-2 | W20909 | *H. pylori* outer membrane protein 14ge10705orf5. | 319 | 1.40E-53 |
| EF009-2 | W20166 | Helicobacter pylori outer membrane protein, 16225006.aa. | 278 | 2.50E-32 |
| EF012-2 | R48035 | Hyaluronic acid synthase of *Streptococcus equisimilis*. | 227 | 3.20E-69 |
| EF014-2 | W14070 | S.thermophilus exopolysaccharide biosynthesis protein EpsR. | 103 | 5.90E-19 |
| EF014-2 | W22169 | S.thermophilus exopolysaccharide synthesis operon epsA gene product. | 103 | 7.30E-18 |
| EF016-2 | W15799 | Adherence factor 104R of *Lactobacillus fermentum*. | 157 | 9.60E-22 |
| EF016-2 | W15793 | Adherence factor consensus sequence. | 103 | 1.00E-l1 |
| EF017-2 | R48035 | Hyaluronic acid synthase of *Streptococcus equisimilis*. | 241 | 8.90E-71 |
| EF021-2 | R31013 | P39-alpha. | 141 | 1.60E-19 |
| EF021-2 | R33280 | P39-beta. | 134 | 7.00E-14 |
| EF022-2 | R48035 | Hyaluronic acid synthase of *Streptococcus equisimilis*. | 324 | 2.20E-65 |
| EF023-2 | R48035 | Hyaluronic acid synthase of *Streptococcus equisimilis*. | 155 | 9.90E-33 |
| EF023-2 | R70152 | *Streptococcus pneumoniae* strain SPRU98 PlpA. | 125 | 5.90E-17 |
| EF027-2 | R48035 | Hyaluronic acid synthase of *Streptococcus equisimilis*. | 233 | 2.20E-34 |
| EF028-2 | W17830 | Thermophilic alkaline phosphatase. | 202 | 7.70E-59 |
| EF028-2 | W11568 | *E. coli* alkaline phosphatase mutant D153H1Q329A. | 182 | 7.90E-56 |
| EF028-2 | W11570 | *E. coli* alkaline phosphatase mutant D153H/K328H/Q329A. | 182 | 7.90E-56 |
| EF028-2 | W26300 | *E. coli* alkaline phosphatase mutant D153H1K328H1Q329A/D330H. | 182 | 1.10E-55 |
| EF028-2 | W11565 | *E. coli* alkaline phosphatase mutant D153H1K328H/D330A. | 182 | 3.10E-55 |
| EF028-2 | W11557 | *E. coli* alkaline phosphatase mutant D153H/D330N. | 182 | 4.30E-55 |
| EF028-2 | W11561 | *E. coli* alkaline phosphatase mutant D15311/D330A. | 182 | 4.30E-55 |
| EF028-2 | W11555 | *E. coli* alkaline phosphatase mutant D153H1K328H1D330N. | 182 | 4.70E-55 |
| EF028-2 | W11566 | *E. coli* alkaline phosphatase mutant D153H/K328H1D330L. | 182 | 1.20E-54 |
| EF028-2 | W11569 | *E. coli* alkaline phosphatase mutant K328H/Q329A. | 180 | 1.70E-54 |
| EF028-2 | W11562 | *E. coli* alkaline phosphatase mutant D153HfD330L. | 182 | 1.70E-54 |
| EF028-2 | R26980 | Fv(FRP5)-phoA recombinant antibody. | 174 | 1.90E-54 |
| EF028-2 | W11567 | *E. coli* alkaline phosphatase mutant Q329A. | 179 | 2.30E-54 |
| EF028-2 | W11558 | *E. coli* alkaline phosphatase mutant K328H/D330N. | 176 | 6.40E-54 |
| EF028-2 | W11563 | *E. coli* alkaline phosphatase mutant K328H/D330A. | 176 | 6.40E-54 |
| EF029-2 | R10044 | Plasmid pOW360 encoded Human Growth Hormone (HGH) - nuclease A | 320 | 3.50E-40 |
| EF029-2 | R10041 | Plasmid pOW350 nuclease A product. | 320 | 4.30E-40 |
| EF029-2 | R73997 | *Staphylococcus aureus* (Foggi) nuclease signal and mature sequences. | 320 | 5.60E-40 |
| EF029-2 | R10043 | Plasmid pOW360 encoding Human Growth Hormone (HGH) - nuclease | 320 | 2.90E-38 |
| EF030-2 | R48035 | Hyaluronic acid synthase of *Streptococcus equisimilis*. | 277 | 6.10E-47 |
| EF040-2 | R59077 | 2-5A-dependent RNA-ase. | 105 | 1.90E-18 |
| EF040-2 | W12703 | Mouse 2-5A-dependent RNase. | 105 | 1.90E-18 |
| EF040-2 | R82661 | Partial murine 2-5A-dependent RNase. | 105 | 1.90E-18 |
| EF041-2 | R48035 | Hyaluronic acid synthase of *Streptococcus equisimilis*. | 225 | 6.30E-26 |
| EF054-2 | R26042 | P.yoelii 55P2 antigen. | 286 | 8.00E-34 |
| EF054-2 | R85782 | Group B Streptococcal mutant beta antigen without IgA binding domain. | 232 | 3.30E-24 |
| EF054-2 | R85781 | Group B Streptococcal wild-type beta antigen. | 232 | 5.20E-24 |
| EF054-2 | P91941 | Sequence of preprospasmolysin. | 204 | 3.10E-19 |
| EF054-2 | W32519 | Collagen-like polypeptide SEQ ID NO:2. | 180 | 7.50E-18 |
| EF054-2 | W12324 | Silver halide emulsion protein monomeric repeat unit #2. | 180 | 7.50E-18 |
| EF054-2 | W32522 | Collagen-like polypeptide SEQ ID NO:5. | 192 | 1.60E-17 |
| EF054-2 | W12327 | Silver halide emulsion protein monomeric repeat unit #5. | 192 | 1.60E-17 |
| EF054-2 | W32520 | Collagen-like polypeptide SEQ ID NO:3. | 189 | 2.40E-17 |
| EF054-2 | W32532 | Collagen-like polypeptide SEQ ID NO:15. | 189 | 2.40E-17 |
| EF054-2 | W12325 | Silver halide emulsion protein monomeric repeat unit #3. | 189 | 2.40E-17 |

TABLE 2-continued

Closest matching sequences between the polypeptides of the present invention and sequences in GenBank and Derwent databases.

| | | | | |
|---|---|---|---|---|
| EF054-2 | W12337 | Silver halide emulsion protein monomeric repeat unit #15. | 189 | 2.40E-17 |
| EF054-2 | W12341 | Silver halide emulsion FLAG(RTM)-tagged protein #2. | 189 | 2.60E-17 |
| EF054-2 | W02098 | S. mutans antigen I/II. | 161 | 5.40E-15 |
| EF054-2 | W02096 | S. mutans antigen I/II fragment (aa803-1114). | 161 | 1.90E-13 |
| EF059-2 | R26042 | P. yoelii SSP2 antigen. | 344 | 1.90E-39 |
| EF059-2 | R85782 | Group B Streptococcal mutant beta antigen without IgA binding domain. | 232 | 1.10E-26 |
| EF059-2 | R85781 | Group B Streptococcal wild-type beta antigen. | 232 | 1.70E-26 |
| EF05 9-2 | P91941 | Sequence of preprospasmolysin. | 200 | 1.50E-18 |
| EF059-2 | P60570 | Sequence of the Falciparum Interspersed Repeat Antigen | 186 | 4.60E-18 |
| EF059-2 | W02096 | S. mutans antigen I/II fragment (aa803-1 114). | 167 | 8.20E-16 |
| EF059-2 | W02098 | S. mutans antigen I/II. | 167 | 4.90E-15 |
| EF059-2 | R79625 | Endocarditis specific antigen region. | 147 | 4.40E-12 |
| EF059-2 | R26049 | MSF precursor. | 143 | 1.30E-11 |
| EF059-2 | R28150 | Sugar beet chitinase 1. | 148 | 1.70E-11 |
| EF059-2 | R26842 | Protease from S. Aureus ATCC12600. | 147 | 2.10E-11 |
| EF059-2 | R79643 | Immunodominant antigen of Streptococcus sobrinus. | 151 | 2.10E-11 |
| EF059-2 | W07539 | Collagen like protein (CLP). | 146 | 3.00E-11 |
| EF061-2 | R26042 | P.yoelii SSP2 antigen. | 241 | 1.70E-25 |
| EF061-2 | P60570 | Sequence of the Falciparum Interspersed Repeat Antigen | 199 | 1.60E-18 |
| EF061-2 | R85782 | Group B Streptococcal mutant beta antigen without IgA binding domain. | 153 | 2.40E-14 |
| EF061-2 | R85781 | Group B Streptococcal wild-type beta antigen. | 153 | 3.60E-14 |
| EF061-2 | P91941 | Sequence of preprospasmolysin. | 163 | 9.70E-14 |
| EF061-2 | P83194 | Sequence of a bioadhesive precursor protein encoded by cDNA clone | 156 | 7.90E-13 |
| EF061-2 | R28150 | Sugar beet chitinase 1. | 156 | 9.10E-13 |
| EF061-2 | W02096 | S. mutans antigen I/II fragment (aa803-1114). | 148 | 1.20E-12 |
| EF061-2 | P82971 | Bioadhesive precursor protein from cDNA 52. | 148 | 9.70E-12 |
| EF061-2 | W02098 | S. mutans antigen I/II. | 148 | 1.50E-11 |
| EF062-2 | W02098 | S. mutans antigen I/II. | 107 | 1.20E-36 |
| EF062-2 | R79643 | Immunodominant antigen of Streptococcus sobrinus. | 132 | 3.00E-36 |
| EF063-2 | W02098 | S. mutans antigen I/II. | 107 | 1.20E-36 |
| EF063-2 | R79643 | Immunodominant antigen of Streptococcus sobrinus. | 132 | 3.00E-36 |
| EF064-2 | W02098 | S. mutans antigen I/II. | 107 | 1.20E-36 |
| EF064-2 | R79643 | Immunodominant antigen of Streptococcus sobrinus. | 132 | 3.00E-36 |
| EF071-2 | R85294 | Phage R1-t LytR lysin. | 127 | 3.70E-38 |
| EF071-2 | R91515 | Listeria phage lysin PLY511. | 273 | 4.70E-37 |
| EF075-2 | W14070 | S. thermophilus exopolysaccharide biosynthesis protein EpsR. | 239 | 4.20E-36 |
| EF075-2 | W22169 | S. thermophilus exopolysaccharide synthesis operon epsA gene product. | 239 | 4.00E-34 |
| EF077-2 | R97280 | Helicobacter-specific ATPase 439. | 258 | 4.10E-74 |
| EF077-2 | R48036 | Mycobacterium BCG immunogen. | 192 | 2.20E-67 |
| EF077-2 | W06712 | Helicobacter-specific ATPase 948 (ORF-4). | 220 | 2.50E-67 |
| EF077-2 | R70419 | Rat homologue of human Wilson disease gene ATP7B. | 186 | 9.80E-54 |
| EF077-2 | R72343 | Wilson disease protein ATP7B. | 176 | 6.70E-40 |
| EF077-2 | R06376 | Product of the sscl gene. | 166 | 3.10E-28 |
| EF077-2 | R75396 | Flea sodium pump alpha subunit. | 146 | 2.40E-25 |
| EF077-2 | W20891 | H. pylori transporter protein, 14ce20219orf1. | 156 | 8.60E-14 |
| EF078-2 | R56667 | Bacteroides fragilis RprX regulatory response protein. | 148 | 8.30E-18 |
| EF078-2 | R74630 | Tomato TGETR1 ethylene response protein. | 130 | 7.80E-13 |
| EF078-2 | R69849 | Ethylene response (ETR) gene product. | 128 | 1.70E-11 |
| EF078-2 | R69850 | Ethylene response (ETR) mutant protein etrl-1. | 128 | 1.70E-11 |
| EF078-2 | R69851 | Ethylene response (ETR) mutant protein etrl-2. | 128 | 1.70E-11 |
| EF078-2 | R69852 | Ethylene response (ETR) mutant protein etrl-3. | 128 | 1.70E-11 |
| EF078-2 | R69853 | Ethylene response (ETR) mutant protein etrl-4. | 128 | 1.70E-11 |
| EF078-2 | R24296 | Regulatory protein VanS involved in glycopeptide resistance. | 142 | 2.70E-11 |
| EF081-2 | R27253 | Penicillin binding protein PBP2A-epi. | 101 | 4.70E-16 |
| EF081-2 | R27256 | Penicillin binding protein PBP2A-27R. | 101 | 6.00E-15 |
| EF081-2 | R27257 | Penicillin binding protein derivative #1. | 101 | 6.20E-15 |
| EF081-2 | R27258 | Penicillin binding protein derivative #2. | 101 | 6.20E-15 |
| EF081-2 | R27259 | Penicillin binding protein derivative #3. | 101 | 6.20E-15 |
| EF081-2 | R27260 | Penicillin binding protein derivative #4. | 101 | 6.20E-15 |
| EF081-2 | R27261 | Penicillin binding protein derivative #5. | 101 | 6.20E-15 |
| EF081-2 | R27263 | Penicillin binding protein derivative #7. | 101 | 6.20E-15 |
| EF081-2 | R27264 | Penicillin binding protein derivative #8. | 101 | 6.20E-15 |
| EF081-2 | R27262 | Penicillin binding protein derivative #6. | 101 | 6.50E-15 |
| EF081-2 | R30845 | Sequence encoded by the mec A gene. | 101 | 6.90E-15 |
| EF081-2 | R27255 | Penicillin binding protein PBP2A-27R. | 101 | 6.90E-15 |
| EF081-2 | R31216 | Penicillin binding protein PBP2A-27R.- | 101 | 7.00E-15 |
| EE110-2 | R91042 | VS mature protease (aal-213). | 106 | 6.60E-16 |
| EF110-2 | R91043 | VS mature protease (aal-214). | 106 | 7.20E-16 |
| EE110-2 | R91044 | VS mature protease (aal-215). | 106 | 7.80E-16 |
| EF110-2 | R26842 | Protease from S. Aureus ATCC12600. | 106 | 6.70E-15 |
| EF110-2 | R29644 | Protease from S. Aureus. | 106 | 1.20E-14 |
| EF110-2 | W22218 | Protein encoded by pV8RPT(-) construct. | 106 | 7.60E-14 |
| EF110-2 | R91033 | Beta-galactosidase-V8 protease fusion protein. | 106 | 7.60E-14 |
| EF110-2 | R91034 | Beta-galactosidase-V8 protease fusion protein. | 106 | 1.70E-13 |
| EF110-2 | W22219 | Protein encoded by pV8D construct. | 106 | 7.60E-13 |
| EE110-2 | R91035 | Recombinant V8 protease V8D fusion protein. | 106 | 7.60E-13 |
| EF110-2 | W22220 | Protein encoded by pV8F construct. | 106 | 7.90E-13 |

TABLE 2-continued

Closest matching sequences between the polypeptides of the present invention and sequences in GenBank and Derwent databases.

| | | | | |
|---|---|---|---|---|
| EF129-2 | R14530 | Usp45 protein. | 374 | 2.40E-43 |
| EF129-2 | R14150 | MSP encoded by pUCRS (DSM 5803). | 372 | 4.70E-43 |
| EF131-2 | R37495 | Pneumococcal fimbrial protein A. | 1185 | 6.80E-163 |
| EF131-2 | W26367 | *Staphylococcus aureus* saliva binding protein. | 418 | 3.70E-85 |
| EF131-2 | R79722 | ROM precursor TROMP 1. | 171 | 9.00E-31 |
| EF131-2 | W22134 | Treponema pallidum rare outer membrane protein (TROMP-1). | 171 | 9.00E-31 |

TABLE 3

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

TABLE 4

Residues Comprising Antigenic Epitope-Bearing Portion.

| | |
|---|---|
| EF001-2 | from about Asp-150 to about Lys-152, from about Ser-256 to about Tyr-259, from about Lys-360 to about Lys-363, from about Asn-406 to about Asp-408. |
| EF002-2 | from about Asp-80 to about Asp-83, from about Asp-281 to about Gly-283. |
| EF003-2 | from about Asn-263 to about Gly-266. |
| EF004-2 | from about Asn-23 to about Asn-26, from about Lys-83 to about Ser-87, from about Tyr-154 to about Asp-159. |
| EF005-2 | from about Lys-249 to about Glu-252. |
| EF006-2 | from about Gly-23 to about Asp-28. |
| EF008-2 | from about Thr-92 to about Gly-94, from about Pro-161 to about Asp-165, from about Gly-287 to about Thr-289. |
| EF010-2 | from about Pro-129 to about Asn-131. |
| EF012-2 | from about Asp-77 to about Asp-79, from about Asp-94 to about Lys-98, from about Asp-256 to about Thr-258, from about Glu-461 to about Asn-468. |
| EF013-2 | from about Thr-30 to about Asp-32, from about Glu-73 to about Ala-75, from about Gln-164 to about Asn-166, from about Lys-193 to about Gly-195. |
| EF014-2 | from about Ser-203 to about Asp-206, from about Gln-314 to about Gly-316 |
| EF015-2 | from about Pro-66 to about Gly-69. |
| EF016-2 | from about Lys-236 to about Asn-239. |
| EF017-2 | from about Ser-90 to about Gly-93, from about Thr-197 to about Lys-199, from about Lys-230 to about Asn-233, from about Ser-428 to about Gly-431. |
| EF018-2 | from about Lys-159 to about Tyr-161, from about Asn-165 to about Ser-167, from about Asn-250 to about Arg-256, from about Asn-392 to about Gly-395, from about Lys-416 to about Tyr-418, from about Asn-428 to about Arg-430. |
| EF019-2 | from about Arg-209 to about Ser-211, from about Lys-287 to about Ser-290. |
| EF020-2 | from about Lys-57 to about Asn-62. |
| EF021-2 | from about Ser-33 to about Gly-35, from about Glu-77 to about Gly-81, from about Asp-139 to about Lys-141, from about Glu-255 to about Ser-258, from about Gln-271 to about Tyr-277. |

TABLE 4-continued

Residues Comprising Antigenic Epitope-Bearing Portion.

| | |
|---|---|
| EF023-2 | from about Lys-232 to about Asp-234, from about Arg-304 to about Gly-306, from about Thr-453 to about Arg-456, from about Ser-478 to about Thr-480. |
| EF025-2 | from about Arg-183 to about Asp-185. |
| EF026-2 | from about Ser-25 to about Asp-30, from about Asp-90 to about Asp-94, from about Gln-107 to about Asn-110. |
| EF027-2 | from about Gln-72 to about Lys-74, from about Lys-229 to about Asp-231. |
| EF028-2 | from about Asp-186 to about Gln-188. |
| EF029-2 | from about Asp-118 to about Lys-122, from about Asp-124 to about Tyr-126. |
| EF031-2 | from about Glu-30 to about Gly-33. |
| EF034-2 | from about Glu-25 to about Gly-27, from about Glu-75 to about Thr-77. |
| EF36-2 | from about Gln-177 to about Ser-179. |
| EF037-2 | from about Ser-25 to about Asp-30, from about Asp-90 to about Asp-94, from about Gln-107 to about Asn-110. |
| EF038-2 | from about Asn-77 to about Lys-79, from about Tyr-88 to about Asn-92. |
| EF040-2 | from about Lys-167 to about Gly-172, from about Lys-240 to about Asn-242. |
| EF044-2 | from about Arg-192 to about Gly-194, from about Asn-200 to about Asn-203. |
| EF045-2 | from about Asp-159 to about Asn-161, from about His-172 to about Gly-174, from about Tyr-261 to about Gly-264, from about Lys-305 to about Glu-308. |
| EF046-2 | from about Ser-18 to about Gly-23, from about Gln-41 to about Ser-47, from about Thr-76 to about Asp-78. |
| EF047-2 | from about Asn-28 to about Asp-30, from about Asp-273 to about Asn-277. |
| EF048-2 | from about Asp-138 to about Lys-141, from about Asp-152 to about Gly-154. |
| EF051-2 | from about Asp-73 to about Gly-76. |
| EF053-2 | from about Ser-79 to about Gly-82. |
| EF055-2 | from about Asp-26 to about Gly-28, from about Gln-67 to about Asp-69, from about Arg-71 to about Gly-74, from about Arg-87 to about Gly-89. |
| EF056-2 | from about Arg-71 to about Gly-74, from about Arg-87 to about Gly-89. |
| EF058-2 | from about Lys-129 to about Gly-133, from about Gln-571 to about Tyr-573, from about Pro-586 to about Gly-591. |
| EF065-2 | from about Ser-236 to about Tyr-239, from about Asp-350 to about Gly-352, from about Lys-415 to about Asn-418, from about Arg-446 to about Asp-448, from about Asn-489 to about Lys-491, from about Ser-516 to about Asp-518, from about Glu-639 to about Lys-642. |
| EF066-2 | from about Ser-236 to about Tyr-239, from about Asp-350 to about Gly-352, from about Lys-415 to about Asn-418, from about Arg-446 to about Asp-448, from about Asn-489 to about Lys-491, from about Ser-516 to about Asp-518, from about Glu-639 to about Lys-642. |
| EF067-2 | from about Ser-236 to about Tyr-239, from about Asp-350 to about Gly-352, from about Lys-415 to about Asn-418, from about Arg-446 to about Asp-448, from about Asn-489 to about Lys-491, from about Ser-516 to about Asp-518, from about Glu-639 to about Lys-642. |
| EF073-2 | from about Met-98 to about Arg-100, from about Arg-110 to about Asp-112. |
| EF074-2 | from about Ser-53 to about Tyr-59, from about Ser-86 to about Gly-88, from about Pro-97 to about Gln-100, from about Gln-230 to about Gly-232. |

TABLE 4-continued

Residues Comprising Antigenic Epitope-Bearing Portion.

| | |
|---|---|
| EF076-2 | from about Asn-38 to about Tyr-40, from about Asp-48 to about Asn-53, from about Lys-79 to about Gly-81. |
| EF077-2 | from about Arg-411 to about Gly-413. |
| EF078-2 | from about Thr-294 to about Gly-296, from about Asp-366 to about Gln-368, from about Glu-524 to about Gly-526. |
| EF080-2 | from about Glu-164 to about Gly-166, from about Ser-206 to about Tyr-208, from about Lys-239 to about Gly-243. |
| EF081-2 | from about Asn-7 to about Ser-11, from about Lys-77 to about Tyr-80, from about Lys-112 to about Asn-114, from about Gly-162 to about Asp-164, from about Arg-181 to about Gly-183. |
| EF083-2 | from about Gln-38 to about Arg-40. |
| EF084-2 | from about Lys-140 to about Asp-142, from about Gly-164 to about Arg-166, from about Arg-262 to about Gly-264. |
| EF085-2 | from about Asn-95 to about Asp-97, from about Arg-112 to about Asp-114, from about Asp-258 to about Ser-260, from about Arg-401 to about Ser-403. |
| EF086-2 | from about Pro-112 to about Gly-115, from about Ser-222 to about Ser-224, from about Asn-296 to about Gly-299, from about Thr-346 to about Lys-348, from about Asp-428 to about Ser-432. |
| EF087-2 | from about Pro-112 to about Gly-115, from about Ser-222 to about Ser-224, from about Asn-296 to about Gly-299, from about Thr-346 to about Lys-348, from about Asp-428 to about Ser-432. |
| EF088-2 | from about Pro-112 to about Gly-115, from about Ser-222 to about Ser-224, from about Asn-296 to about Gly-299, from about Thr-346 to about Lys-348, from about Asp-428 to about Ser-432. |
| EF090-2 | from about Arg-2 to about Arg-5. |
| EF091-2 | from about Gln-40 to about Asp-43. |
| EF093-2 | from about Lys-95 to about Gly-97. |
| EF094-2 | from about Asp-314 to about Asp-316. |
| EF095-2 | from about Ser-328 to about Thr-330, from about Asp-359 to about Asp-363, from about Glu-637 to about Gly-639, from about Asn-744 to about Gly-746. |
| EF096-2 | from about Pro-128 to about Asn-130, from about Ser-193 to about Asp-196. |
| EF097-2 | from about Val-357 to about Gly-359. |
| EF099-2 | from about Glu-44 to about Asp-47, from about Lys-154 to about Gly-156, from about Asn-286 to about Asp-289. |
| EF101-2 | from about Lys-40 to about Asp-42, from about Pro-255 to about Asn-258, from about Lys-288 to about Gly-290. |
| EF102-2 | from about Asp-314 to about Asp-316. |
| EF103-2 | from about Asn-46 to about Gly-48. |
| EF104-2 | from about Pro-232 to about Lys-237, from about Ala-362 to about Asn-366, from about Ser-421 to about Gly-423, from about Lys-488 to about Ser-490, from about Asp-550 to about Asn-552, from about Pro-637 to about Lys-640, from about Asp-727 to about Gly-729, from about Asn-751 to about Ser-754, from about Lys-771 to about Asn-774, from about Ile-835 to about Asn-837, from about Pro-851 to about Gly-853. |
| EF105-2 | from about Ser-40 to about Gly-43, from about Asn-94 to about Gln-97, from about Gln-220 to about Gly-222, from about Asn-263 to about Gly-265. |
| EF106-2 | from about Asp-72 to about Gly-75, from about Thr-274 to about Asp-277, from about Asn-310 to about Arg-313. |
| EF107-2 | from about Thr-155 to about Asn-157, from about Thr-189 to about Asp-191, from about Arg-270 to about Gly-272, from about Thr-330 to about Lys-335, from about Asp-365 to about Asp-368, from about Pro-451 to about Asp-453, from about Gly-485 to about Thr-488. |
| EF108-2 | from about Lys-142 to about Trp-145, from about Thr-147 to about Tyr-150, from about Arg-212 to about Gly-214, from about Ser-248 to about Asp-251, from about Asp-384 to about Asp-387, from about Pro-481 to about Arg-483, from about Lys-491 to about Gly-494, from about Thr-619 to about Gly-624, from about Asp-656 to about Asp-659, from about Lys-717 to about Asn-721, from about Ser-822 to about Gly-824, from about Tyr-1137 to about Thr-1141. |
| EF110-2 | from about Pro-123 to about Gly-127, from about Thr-223 to about Gly-225. |
| EF111-2 | from about Lys-207 to about Asn-209, from about Asp-245 to about Asn-248, from about Lys-396 to about Asp-398, from about Glu-429 to about Ser-432, from about Thr-470 to about His-474. |
| EF119-2 | from about Asp-90 to about Asn-92, from about Gln-142 to about Gly-144. |
| EF121-2 | from about Asn-159 to about Asp-161, from about Asn-351 to about Lys-353, from about Pro-658 to about Gly-660, from about Lys-786 to about Ser-789. |
| EF122-2 | from about Asn-159 to about Asp-161, from about Asn-351 to about Lys-353, from about Pro-658 to about Gly-660, from about Lys-786 to about Ser-789. |
| EF123-2 | from about Asn-331 to about Arg-336, from about Asp-634 to about Gly-636, from about Glu-780 to about Ser-782, from about Tyr-909 to about Asn-911, from about Lys-939 to about Glu-942, from about Asp-1074 to about Gly-1076, from about Asp-1367 to about Gly-1369, from about Pro-1433 to about Lys-1435, from about Gly-1516 to about Asp-1518, from about Lys-1656 to about Asp-1660, from about Lys-1860 to about Gln-1863, from about Ser-1916 to about Gln-1919, from about Pro-1940 to about Gly-1942. |
| EF124-2 | from about Asn-331 to about Arg-336, from about Asp-634 to about Gly-636, from about Glu-780 to about Ser-782, from about Tyr-909 to about Asn-911, from about Lys-939 to about Glu-942, from about Asp-1074 to about Gly-1076, from about Asp-1367 to about Gly-1369, from about Pro-1433 to about Lys-1435, from about Gly-1516 to about Asp-1518, from about Lys-1656 to about Asp-1660, from about Lys-1860 to about Gln-1863, from about Ser-1916 to about Gln-1919, from about Pro-1940 to about Gly-1942. |
| EF125-2 | from about Asn-331 to about Arg-336, from about Asp-634 to about Gly-636, from about Glu-780 to about Ser-782, from about Tyr-909 to about Asn-911, from about Lys-939 to about Glu-942, from about Asp-1074 to about Gly-1076, from about Asp-1367 to about Gly-1369, from about Pro-1433 to about Lys-1435, from about Gly-1516 to about Asp-1518, from about Lys-1656 to about Asp-1660, from about Lys-1860 to about Gln-1863, from about Ser-1916 to about Gln-1919, from about Pro-1940 to about Gly-1942. |
| EF126-2 | from about Ser-236 to about Tyr-239, from about Asp-350 to about Gly-352, from about Lys-415 to about Asn-418, from about Arg-446 to about Asp-448, from about Asn-489 to about Lys-491, from about Ser-516 to about Asp-518, from about Glu-639 to about Lys-642. |
| EF127-2 | from about Ser-236 to about Tyr-239, from about Asp-350 to about Gly-352, from about Lys-415 to about Asn-418, from about Arg-446 to about Asp-448, from about Asn-489 to about Lys-491, from about Ser-516 to about Asp-518, from about Glu-639 to about Lys-642. |
| EF128-2 | from about Ser-236 to about Tyr-239, from about Asp-350 to about Gly-352, from about Lys-415 to about Asn-418, from about Arg-446 to about Asp-448, from about Asn-489 to about Lys-491, from about Ser-516 to about Asp-518, from about Glu-639 to about Lys-642. |
| EF129-2 | from about Asn-300 to about Gly-302, from about Ser-316 to about Gly-319, from about Asn-385 to about His-387 |
| EF131-2 | from about Lys-201 to about Tyr-204, from about Glu-263 to about Ser-266. |
| EF132-2 | from about Thr-26 to about Ser-28. |

What is claimed is:

1. An isolated polynucleotide of comprising a nucleic acid sequence encoding the full length acid sequence in SEQ ID NO:222.

2. The isolated polynucleotide of claim 1, wherein said heterologous polynucleotide sequence.

3. The isolated polynucleotide of claim 1, wherein said heterologous polynucleotide sequence encodes a heterologous polypeptide.

4. An isolated polynucleotide which is fully complementary to the polynucleotide of claim 1.

5. A method for making a recombinant vector comprising inserting the isolated polynucleotide of claim 1 into a vector.

6. A recombinant vector comprising the isolated polynucleotide of claim 1.

7. The recombinant vector of claim 6, wherein said isolated polynucleotide is operably associated with a heterologous regulatory sequence that controls gene expression.

8. An isolated recombinant host cell comprising the isolated polynucleotide of claim 1.

9. The isolated recombinant host cell of claim 8, wherein said polynucleotide is operably associated with a heterologous regulatory sequence that controls gene expression.

10. A method for producing a polypeptide, comprising culturing the host cell of claims under conditions suitable to produce the polypeptide encoded by said polynucleotide.

11. An isolated polynucleotide consisting of a nucleic acid sequence encoding a fragment of SEQ ID NO:222, wherein said fragment is at least 15 contiguous amino acid residues in length.

12. An isolated polynucleotide which is fully complementary to the polynucleotide of claim 11.

13. The isolated polynucleotide of claim 11, wherein said fragment is at least 30 contiguous amino acid residues in length.

14. A isolated polynucleotide which is fully complementary to the polynucleotide of claim 13.

15. An isolated polynucleotide consisting of a fragment of SEQ ID NO:221, wherein said fragment is at least 50 contiguous nucleotides in length.

16. An isolated polynucleotide which is fully complementary to the polynucleotide of claim 15.

17. The isolated polynucleotide of claim 15, wherein said fragment is at least 100 contiguous nucleotides in length.

18. An isolated polynucleotide which is fully complementary to the polynucleotide of claim 17.

19. An isolated polynucleotide consisting of a nucleic acid sequence encoding the full length amino acid sequence in SEQ ID NO:224.

20. The isolated polynucleotide of claim 19, which is fused to a heterologous polynucleotide sequence.

21. The isolated polynucleotide of claim 20, wherein said heterologous polynucleotide sequence encodes a heterologous polypeptide.

22. A method for making a recombinant vector comprising inserting the isolated polynucleotide of claim 19 into a vector.

23. An isolated polynucleotide which is fully complementary to the polynucleotide of claim 14.

24. A recombinant vector comprising the isolated polynucleotide of claim 19.

25. The recombinant vector of claim 24, wherein said polynucleotide is operably associated with a heterologous regulatory sequence that controls gene expression.

26. A recombinant host cell comprising the isolated polynucleotide of claim 19.

27. The recombinant host cell of claim 26, wherein said polynucleotide is operably associated with a heterologous regulatory sequence that controls gene expression.

28. A method for producing a polypeptide, comprising culturing the recombinant host cell of claim 26, under conditions suitable to produce the polypeptide encoded by said polynucleotide.

29. An isolated polynucleotide consisting of a nucleic acid sequence encoding a fragment of SEQ ID NO:224, wherein said fragment is at least 15 contiguous amino acid residues in length.

30. An isolated polynucleotide which is fully complementary to the polynucleotide fragment of claim 29.

31. The isolated polynucleotide of claim 29 wherein said fragment is at least 30 contiguous amino acid residues in length.

32. An isolated polynucleotide which is fully complementary to the polynucleotide of claim 31.

33. An isolated polynucleotide consisting of a fragment of SEQ ID NQ:223, wherein said fragment is at least 50 contiguous nucleotides in length.

34. An isolated polynucleotide which is fully complementary to the polynucleotide of claim 33.

35. The isolated polynucleotide of claim 33, wherein said fragment is at least 100 contiguous nucleotides in length.

36. An isolated polynucleotide which is fully complementary to the polynucleotide of claim 35.

37. The isolated polynucleotide of claim 1 consisting of the nucleotide sequence of SEQ ID NO:221, or the complement thereof.

38. The isolated polynucleotide of claim 19 consisting of the nucleotide sequence of SEQ ID NQ:223, or the complement thereof.

* * * * *